(12) United States Patent
Pauls et al.

(10) Patent No.: US 8,980,934 B2
(45) Date of Patent: Mar. 17, 2015

(54) KINASE INHIBITORS AND METHOD OF TREATING CANCER WITH SAME

(71) Applicants: Heinz W. Pauls, Oakville (CA); Radoslaw Laufer, Oakville (CA); Sze-Wan Li, Toronto (CA); Grace Ng, Richmond Hill (CA)

(72) Inventors: Heinz W. Pauls, Oakville (CA); Radoslaw Laufer, Oakville (CA); Sze-Wan Li, Toronto (CA); Grace Ng, Richmond Hill (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 13/923,982

(22) Filed: Jun. 21, 2013

(65) Prior Publication Data

US 2014/0005167 A1    Jan. 2, 2014

Related U.S. Application Data

(60) Provisional application No. 61/663,375, filed on Jun. 22, 2012.

(51) Int. Cl.
*A61K 31/416* (2006.01)
*C07D 231/56* (2006.01)
*C07D 491/107* (2006.01)
*C07D 403/10* (2006.01)
*C07D 401/14* (2006.01)
*C07D 487/10* (2006.01)
*C07D 409/14* (2006.01)

(52) U.S. Cl.
CPC .......... *C07D 491/107* (2013.01); *C07D 403/10* (2013.01); *C07D 401/14* (2013.01); *C07D 487/10* (2013.01); *C07D 409/14* (2013.01)
USPC ........................................ 514/406; 548/361.1

(58) Field of Classification Search
CPC .. C07D 401/10; C07D 401/14; C07D 403/10; C07D 403/14; C07D 405/14; C07D 409/14

USPC .......................................... 548/361.1; 514/406
See application file for complete search history.

(56) References Cited

FOREIGN PATENT DOCUMENTS

| CA | 2440842 A1 | 10/2002 |
| CA | 2473986 A1 | 8/2003 |
| WO | 2011/123937 A1 | 10/2011 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

* cited by examiner

*Primary Examiner* — Shawquia Jackson
(74) *Attorney, Agent, or Firm* — McCarter & English, LLP; Steven G. Davis; Wei Song

(57) ABSTRACT

The present teachings provide a compound represented by structural formula (I):

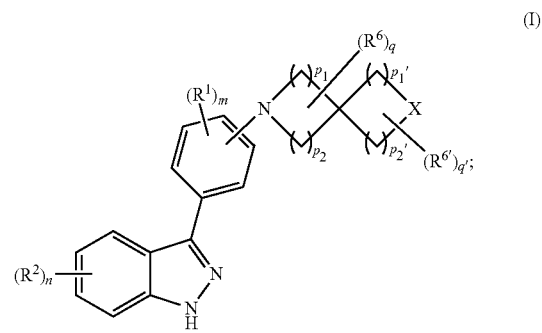

or a pharmaceutically acceptable salt thereof. Also described are pharmaceutical compositions and methods of use thereof.

21 Claims, No Drawings

KINASE INHIBITORS AND METHOD OF TREATING CANCER WITH SAME

RELATED APPLICATIONS

This application claims priority to U.S Provisional Application Ser. No. 61/663,375, filed Jun. 22, 2012. The entire contents of this application are incorporated herein by reference.

BACKGROUND OF THE INVENTION

Protein kinases have been the subject of extensive study in the search for new therapeutic agents in various diseases, for example, cancer. Protein kinases are known to mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell.

Human TTK protein kinase (TTK), also known as tyrosine threonine kinase, dual specificity protein kinase TTK, Monopolar Spindle 1 (Mpsl) and Phosphotyrosine-Picked Threonine Kinase (PYT), is a conserved multispecific kinase that is capable of phosphorylating serine, threonine and tyrosine residues when expressed in *E. coli* (Mills et al., *J. Biol. Chem.* 22(5): 16000-16006 (1992)). TTK mRNA is not expressed in the majority of physiologically normal tissues in human (Id.). TTK mRNA is expressed in some rapidly proliferating tissues, such as testis and thymus, as well as in some tumors (for example, TTK mRNA was not expressed in renal cell carcinoma, was expressed in 50% of breast cancer samples, was expressed in testicular tumors and ovarian cancer samples) (Id.). TTK is expressed in some cancer cell lines and tumors relative to normal counterparts (Id.; see also WO 02/068444 A1).

Therefore, agents which inhibit a protein kinase, in particular TTK, have the potential to treat cancer. There is a need for additional agents which can act as protein kinase inhibitors, in particular TTK inhibitors.

In addition, cancer recurrence, drug resistance or metastasis is one of the major challenges in cancer therapies. Cancer patients who responded favorably to the initial anti-cancer therapy often develop drug resistance and secondary tumors that lead to the relapse of the disease. Recent research evidences suggest that the capability of a tumor to grow and propagate is dependent on a small subset of cells within the tumor. These cells are termed tumor-initiating cells (TICs) or cancer stem cells. It is thought that the TICs are responsible for drug resistance, cancer relapse and metastasis. Compounds that can inhibit the growth and survival of these tumor-initiating cells can be used to treat cancer, metastasis or prevent recurrence of cancer. Therefore, a need exists for new compounds that can inhibit the growth and survival of tumor-initiating cells.

SUMMARY OF THE INVENTION

Applicants have now discovered that certain indazole compounds are potent kinase inhibitors, such as TTK protein kinase. Applicants have also now discovered that these indazole compounds have potent anticancer activity against breast cancer cells, colon cancer cells, and ovarian cancer cells in cell culture study. Based on these discoveries, indazole compounds, pharmaceutical compositions thereof, and methods of treating cancer with the indazole compounds are disclosed herein.

The present teachings are directed, at least in part, to an indazole compound represented by the following structural formula:

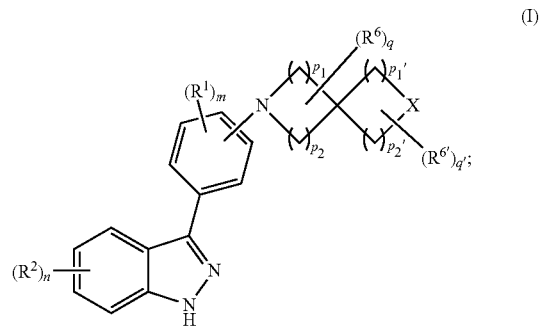

or a pharmaceutically acceptable salt thereof, wherein:

each $R^1$ is independently selected from —H, -halogen, —CN, —NO$_2$, OR$^c$, —NR$^a$R$^b$, —S(O)$_i$R$^c$, —NR$^d$S(O)$_i$R$^c$, —S(O)$_i$NR$^e$R$^f$, —C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, heterocycloalkyl, and alkyl, wherein the heterocycloalkyl or the alkyl is optionally substituted with 1 to 3 substituents independently selected from -halogen, —CN, —NO$_2$, OR$^c$, —NR$^a$R$^b$, —S(O)$_i$R$^c$, —NR$^d$S(O)$_i$R$^c$, —S(O)$_i$NR$^e$R$^f$, —C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, and —C(=O)R$^c$;

each $R^2$ is independently selected from —(CH$_2$)$_{0-2}$C(=O) NR$^4$(CH$_2$)$_{0-2}$Z—R$^5$, —(CH$_2$)$_{0-2}$NR$^4$C(=O)(CH$_2$)$_{0-2}$Z—R$^5$, and —(CH$_2$)$_{0-2}$NR$^4$C(=O)NR$^4$(CH$_2$)$_{0-2}$Z—R$^5$;

X is —O—, —CR$^8$R$^9$—, —NR$^{11}$—, or —S(O)$_i$—;

$R^4$ is —H or an alkyl group optionally substituted with 1 to 3 substituents independently selected from halogen, hydroxy, and (C$_1$-C$_3$)alkoxy;

$R^5$ is alkyl, cycloalkyl, heterocycloalkyl, aryl, or heteroaryl, each of which is optionally substituted with 1 to 3 groups individually represented by $R^{15}$ or $R^{16}$;

Z is a bond or —CR$^{13}$R$^{14}$—;

$R^6$ and $R^{6'}$ are each independently selected from halogen, hydroxy, (C$_1$-C$_3$)alkyl, (C$_1$-C$_3$)alkoxy, (C$_1$-C$_3$)alkyl-OR$^c$, and —NR$_a$R$_b$; or two instances of $R^6$ or $R^{6'}$ on the same carbon are taken together form =O;

$R^8$ and $R^9$ are each independently selected from —H, —OR$^c$, and (C$_1$-C$_6$)alkyl, wherein the (C$_1$-C$_6$)alkyl group is optionally substituted with 1 to 3 substituents independently selected from halogen, hydroxy, and (C$_1$-C$_3$)alkoxy;

$R^{11}$ is —H, (C$_1$-C$_6$)alkyl, cycloalkyl, cycloalkyl(C$_1$-C$_6$) alkyl, heterocycloalkyl, heterocycloalkyl(C$_1$-C$_6$)alkyl, —C(=O)R$^c$, or —C(=O)OR$^c$, wherein each of the (C$_1$-C$_6$) alkyl, cycloalkyl, cycloalkyl(C$_1$-C$_6$)alkyl, heterocycloalkyl and heterocycloalkyl(C$_1$-C$_6$)alkyl groups is optionally substituted with 1 to 3 substituents independently selected from halogen, hydroxy, (C$_1$-C$_3$)alkoxy, and —C(=O)NR$^e$R$^f$;

$R^{13}$ and $R^{14}$ are each independently selected from —H, alkyl, —OR$^c$, —NR$^a$R$^b$, —(C$_1$-C$_3$)alkylene-NR$^a$R$^b$, —(C$_1$-C$_3$)alkylene-OR$^c$, —(C$_1$-C$_3$)alkylene-OH, cycloalkyl, —O-cycloalkyl, and heterocycloalkyl, wherein each of the cycloalkyl or heterocycloalkyl, groups is optionally substituted with 1 to 3 substituents independently selected from (C$_1$-C$_3$)alkyl and (C$_1$-C$_3$)alkoxy, provided that $R^{13}$ and $R^{14}$ are not both selected from —OR$^c$ and —NR$^a$R$^b$;

$R^{15}$ and $R^{16}$ are each independently selected from halogen, —CN, —NO$_2$, =O, —OR$^c$, —NR$^a$R$^b$, —S(O)$_i$R$^c$, —NR$^d$S(O)$_i$R$^c$, —S(O)$_i$NR$^e$R$^f$, C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, (C$_1$-C$_6$)alkyl, aryl, aryl(C$_1$-C$_3$)alkyl, heterocycloalkyl and heteroaryl; wherein each (C$_1$-C$_6$)alkyl, aryl, aryl(C$_1$-C$_3$)alkyl, heterocycloalkyl and heteroaryl represented by $R^{15}$ is optionally substituted with 1 to 3 substituents independently selected from -halogen, —CN, —OR$^c$, (C$_1$-C$_6$)alkyl, halo(C$_1$-C$_6$)alkyl, (C$_1$-C$_3$)alkoxy, halo(C$_1$-C$_3$)alkoxy, (C$_1$-C$_3$)alkoxy(C$_1$-C$_6$)alkyl, 3 to 8 membered heterocycloalkyl and 3 to 8 membered heteroaryl;

R$^a$ and R$^b$ are each independently selected from —H and (C$_1$-C$_6$)alkyl, optionally substituted with 1 to 3 substituents independently selected from halogen, hydroxy, —NR$^g$R$^h$, and (C$_1$-C$_3$)alkoxy;

R$^c$ is —H or (C$_1$-C$_6$)alkyl, optionally substituted with 1 to 3 substituents independently selected from halogen, —NR$^g$R$^h$, hydroxy, and (C$_1$-C$_3$)alkoxy;

R$^d$ is —H or (C$_1$-C$_6$)alkyl, optionally substituted with 1 to 3 substituents independently selected from halogen, —NR$^g$R$^h$, hydroxy, and (C$_1$-C$_3$)alkoxy;

R$^e$ and R$^f$ are each independently selected from —H and (C$_1$-C$_6$)alkyl optionally substituted with 1 to 3 substituents independently selected from halogen, —NR$^g$R$^h$, hydroxy, and (C$_1$-C$_3$)alkoxy; or R$^e$ and R$^f$, together with the nitrogen to which they are attached, form a 3-8 membered ring optionally substituted with 1 to 3 substituents independently selected from halogen, —NR$^g$R$^h$, —CN, (C$_1$-C$_6$)alkyl, halo(C$_1$-C$_6$)alkyl, (C$_1$-C$_3$)alkoxy, halo(C$_1$-C$_3$)alkoxy, and (C$_1$-C$_3$)alkoxy(C$_1$-C$_6$)alkyl;

R$^g$ and R$^h$ are each independently selected from —H, (C$_1$-C$_6$)alkyl, halo(C$_1$-C$_6$)alkyl, hydroxy(C$_1$-C$_6$)alkyl, and (C$_1$-C$_3$)alkoxy(C$_1$-C$_6$)alkyl;

i is 0, 1, or 2;
n is an integer from 1 to 4;
m is an integer from 1 to 4;
each of $p_1$, $p_2$, $p_1'$, and $p_2'$, independently, is 0, 1, 2, 3, or 4, provided that $p_1+p_2$ is greater than 1, and $p_1'+p_2'$ is greater than 1;
q is 0, 1, or 2; and
q' is 0, 1, or 2.

In another embodiment, the present teachings include a pharmaceutical composition comprising a pharmaceutically acceptable carrier or diluent and a compound represented by structural formula (I) described above or a pharmaceutically acceptable salt thereof.

Another embodiment of the present teachings provides a method of treating a subject having cancer comprising administering to the subject an effective amount of a compound of structural formula (I) or a pharmaceutically acceptable salt thereof.

Another embodiment of the present teachings provides a method of inhibiting TTK activity in a subject in need of inhibition of TTK activity, comprising administering to the subject an effective amount of a compound represented by structural formula (I) or a pharmaceutically acceptable salt thereof.

Another embodiment of the present teachings includes a compound represented by structural formula (I) or a pharmaceutically acceptable salt thereof for use in therapy. In some embodiments, the therapy is for treating a subject with cancer. Alternatively, the therapy is for inhibiting TTK activity in a subject in need of inhibition of TTK activity.

Another embodiment of the present teachings includes the use of a compound represented by structural formula (I) or a pharmaceutically acceptable salt thereof for the manufacture of a medicament for treating a subject with cancer.

Another embodiment of the present teachings includes the use of a compound represented by structural Formulas (I) or a pharmaceutically acceptable salt thereof for the manufacture of a medicament for inhibiting TTK activity in a subject in need of inhibition of TTK activity.

DETAILED DESCRIPTION OF THE INVENTION

In one embodiment, the present teachings are directed to a compound represented by structural formula (I) or a pharmaceutically acceptable salt thereof; and values and alternative values for the variables in structural formula (I) are provided in the following paragraphs:

In a first embodiment, $R^5$ is cycloalkyl, heterocycloalkyl, aryl, or heteroaryl, each of which is optionally substituted with 1 to 3 groups individually represented by $R^{15}$ or $R^{16}$; and values and alternative values for the remainder of the variables are as described for structural formula (I).

In a second embodiment, the group represented by

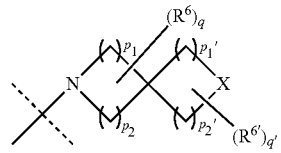

is meta or para to the indazole ring of structural formula (I); and values and alternative values for the remainder of the variables are as described for structural formula (I) or in the first embodiment.

In a third embodiment, the compound is represented by a structural formula selected from:

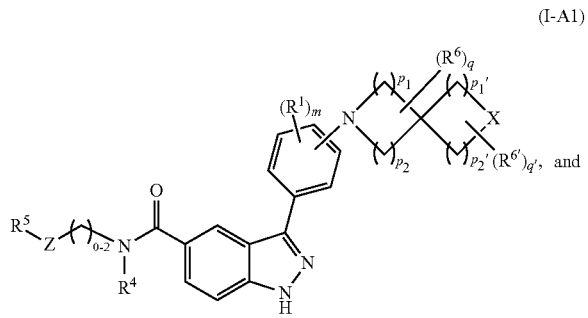

(I-A1)

and

-continued (I-A2)

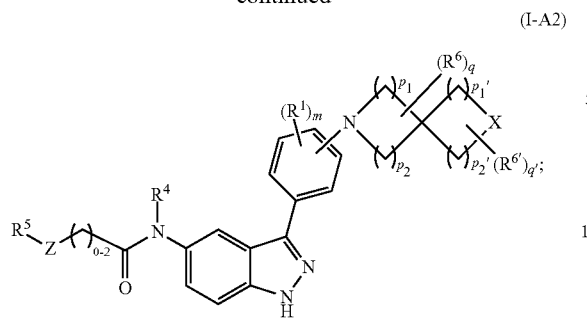

or a pharmaceutically acceptable salt thereof; and values and alternative values for the remainder of the variables are as described for structural formula (I) or in the first or second embodiment.

In a fourth embodiment, the compound is represented by a structural formula selected from:

(I-B1)

(I-B2)

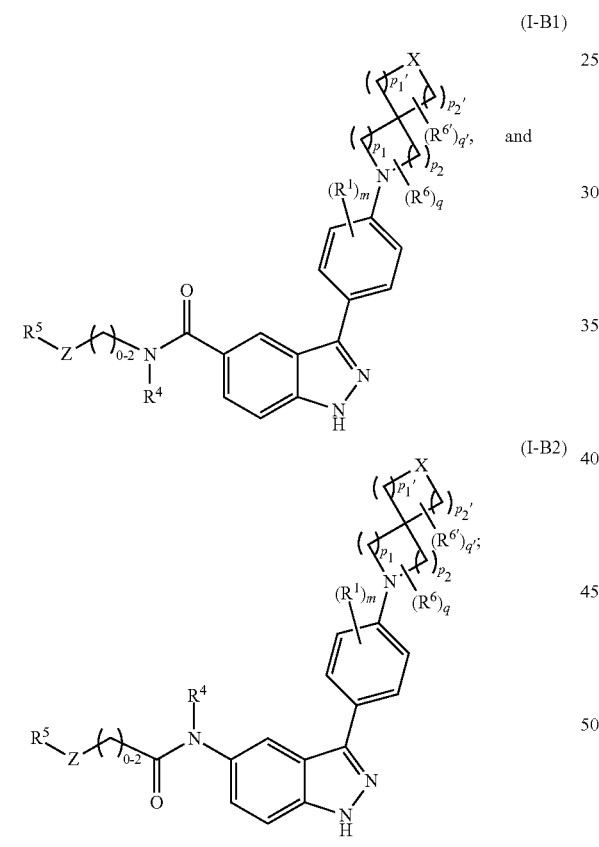

or a pharmaceutically acceptable salt thereof; and values and alternative values for the remainder of the variables are as described for structural formula (I) or in the first or second embodiment.

In one embodiment, for compounds described in structural formula (I) or in the first, second, third, or fourth embodiment, Z is a bond. In another embodiment, for compounds described in structural formula (I) or in the first, second, third, or fourth embodiment, Z is —$CR^{13}R^{14}$—.

In a fifth embodiment, the compound is represented by a structural formula selected from:

(I-C1)

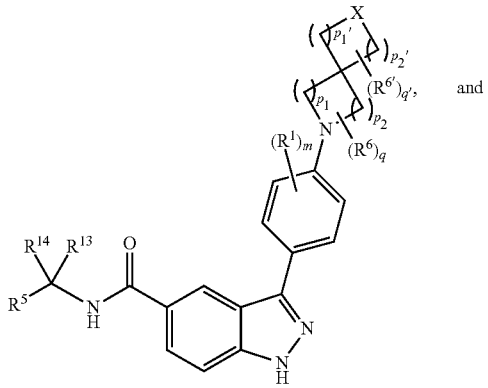

(I-C2)

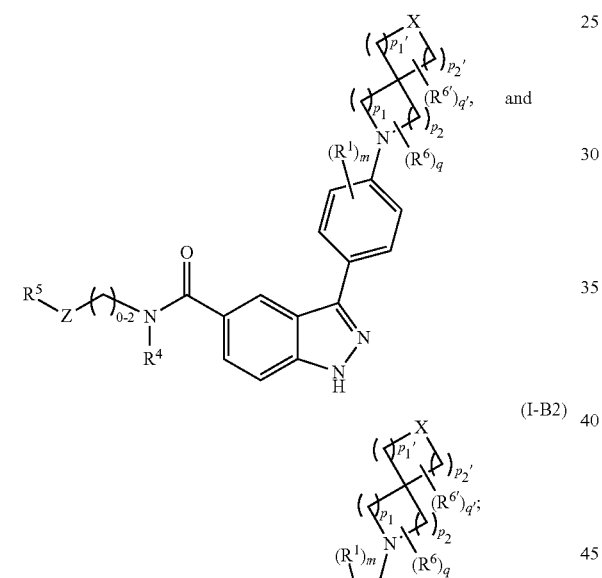

or a pharmaceutically acceptable salt thereof; and values and alternative values for the remainder of the variables are as described for structural formula (I) or in the first or second embodiment.

In a sixth embodiment, the compound is represented by a structural formula selected from:

(I-D1)

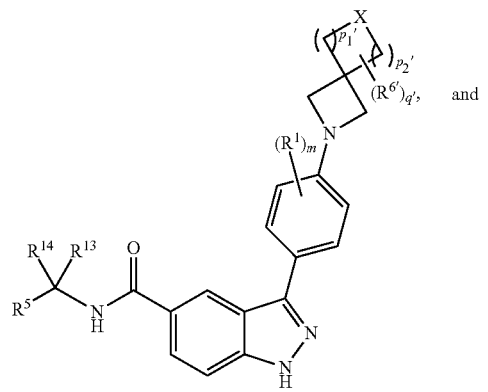

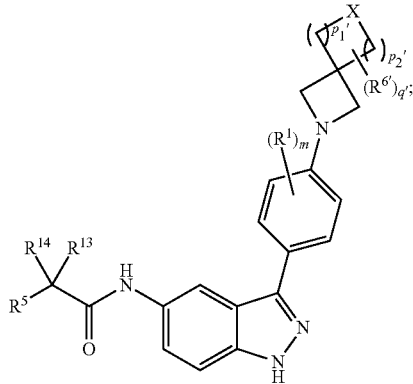

(I-D2)

or a pharmaceutically acceptable salt thereof; and values and alternative values for the remainder of the variables are as described for structural formula (I) or in the first or second embodiment.

In a seventh embodiment, the compound is represented by a structural formula selected from:

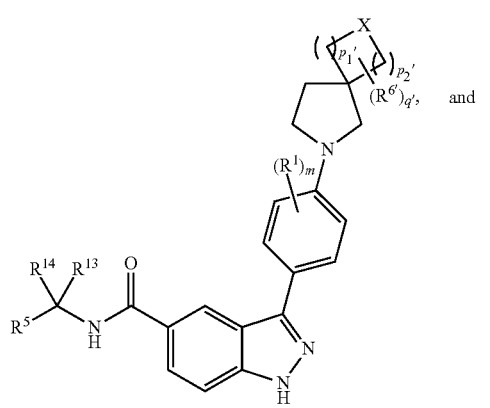

(I-E1)

(I-E2)

or a pharmaceutically acceptable salt thereof; and values and alternative values for the remainder of the variables are as described for structural formula (I) or in the first or second embodiment.

In an eighth embodiment, the compound is represented by a structural formula selected from:

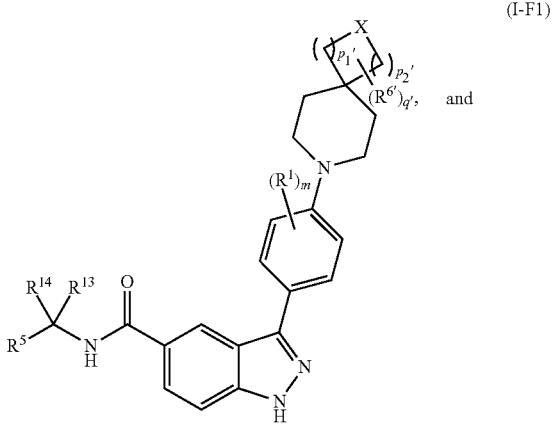

(I-F1)

(I-F2)

or a pharmaceutically acceptable salt thereof; and values and alternative values for the remainder of the variables are as described for structural formula (I) or in the first or second embodiment.

In a ninth embodiment, the compound is represented by a structural formula selected from:

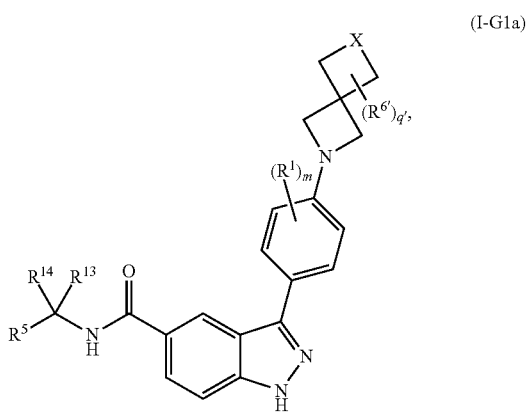

(I-G1a)

-continued
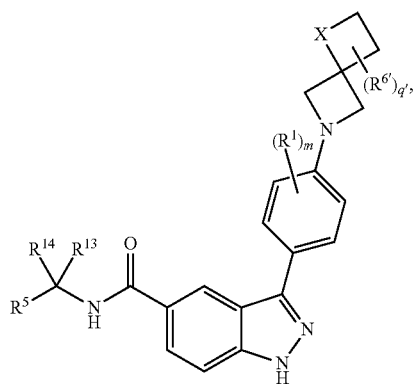
(I-G1b)
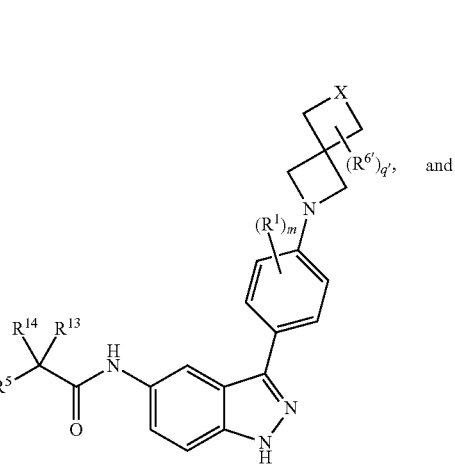
(I-G2a) and
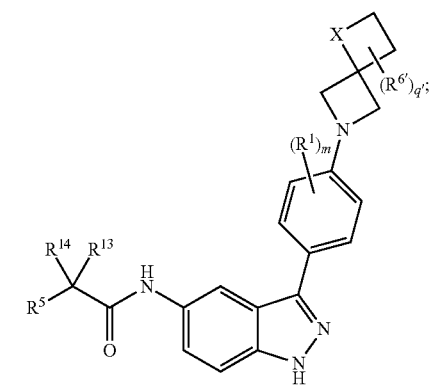
(I-G2b)
or a pharmaceutically acceptable salt thereof; and values and alternative values for the remainder of the variables are as described for structural formula (I) or in the first or second embodiment.
In a tenth embodiment, the compound is represented by a structural formula selected from:
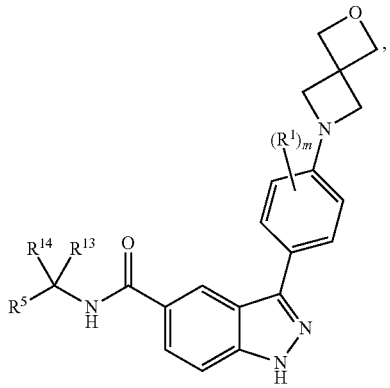
(I-H1a)
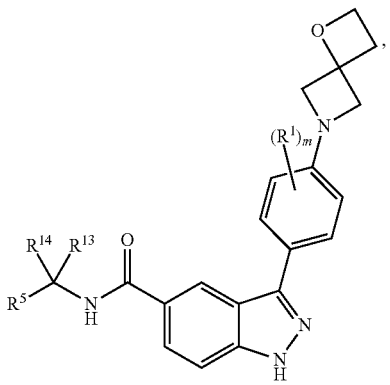
(I-H1b)
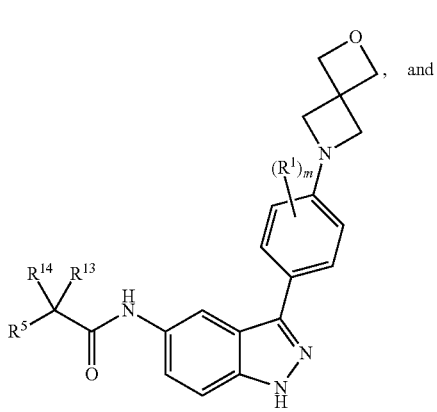
(I-H2a) and (I-H2b)

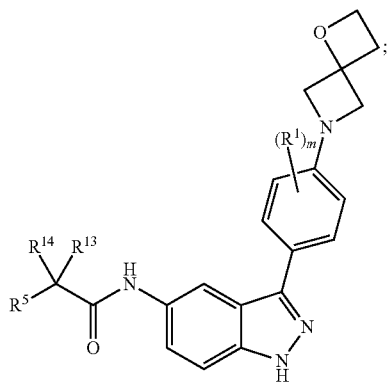

or a pharmaceutically acceptable salt thereof; and values and alternative values for the remainder of the variables are as described for structural formula (I) or in the first or second embodiment.

In an eleventh embodiment, the compound is represented by a structural formula selected from:

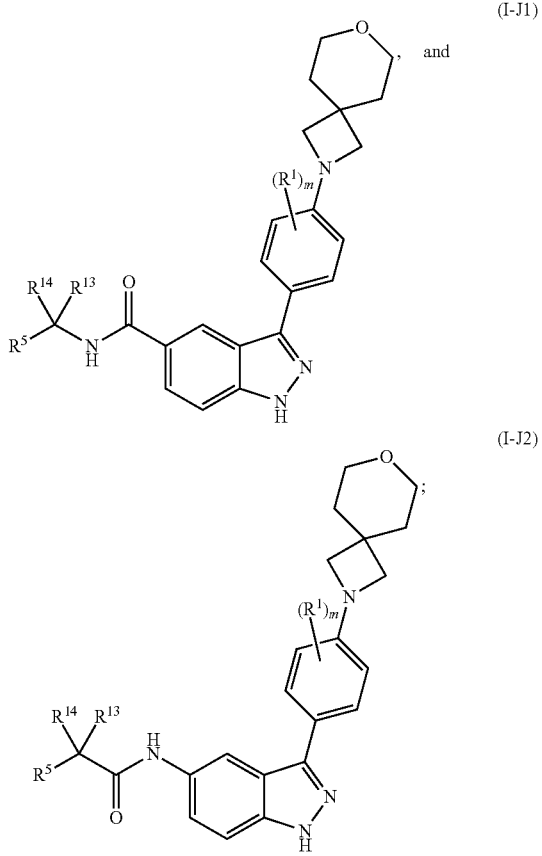

or a pharmaceutically acceptable salt thereof; and values and alternative values for the remainder of the variables are as described for structural formula (I) or in the first or second embodiment.

In a twelfth embodiment, for compound represented by any one of structural formulae (I), (I-A1)-(I-F2), (I-G1a)-(I-H2b), or (I-J1)-(I-J2), the group represented by X is —O—, —CR$^8$R$^9$—, or —NR$^{11}$—;

R$^4$ is —H;

R$^6$ and R$^{6'}$ are each independently (C$_1$-C$_3$)alkyl;

R$^8$ and R$^9$ are each independently selected from —H, —OR$^c$, and (C$_1$-C$_6$)alkyl, wherein the (C$_1$-C$_6$)alkyl group is optionally substituted with a substituent selected from halogen, hydroxy and (C$_1$-C$_3$)alkoxy;

R$^{11}$ is —H, (C$_1$-C$_6$)alkyl, heterocycloalkyl, or —C(=O)R$^c$, wherein the (C$_1$-C$_6$)alkyl is optionally substituted with a substituent selected from halogen, hydroxy, (C$_1$-C$_3$)alkoxy and —C(=O)NR$^e$R$^f$;

R$^{13}$ and R$^{14}$ are each independently selected from —H, alkyl, —OR$^c$, —(C$_1$-C$_3$)alkylene-OR$^c$, —(C$_1$-C$_3$)alkylene-OH, (C$_3$-C$_8$)cycloalklyl, —O—(C$_3$-C$_8$)cycloalkyl and 3 to 8 membered heterocycloalkyl, provided that R$^{13}$ and R$^{14}$ are not both —OR$^c$, wherein each of the cycloalkyl or heterocycloalkyl groups is optionally substituted with a (C$_1$-C$_3$)alkyl;

n is an integer from 1 to 2;

m is an integer from 1 to 2; and each of p$_1$, p$_2$, p$_1'$, and p$_2'$, independently, is 0, 1, or 2, provided that p$_1$+p$_2$ is greater than 1, and p$_1'$+p$_2'$ is greater than 1; and values and alternative values for the remainder of the variables are as described for structural formula (I) or in the first or second embodiment.

In a thirteenth embodiment, for compound represented by any one of structural formulae (I), (I-A1)-(I-F2), (I-G1a)-(I-H2b), or (I-J1)-(I-J2), each R$^1$ is independently selected from —H, -halogen, —CN, —NO$_2$, OR$^c$, —NR$^a$R$^b$, —S(O)$_r$R$^c$, —C(=O)OR$^c$, —OC(=O)OR$^c$, —C(=O)NR$^e$R$^f$, —NR$^d$C(=O)R$^c$, —C(=O)R$^c$ or alkyl, wherein the alkyl is optionally substituted with a substituent selected from -halogen, —OR$^c$, —NR$^a$R$^b$, and —S(O)$_r$R$^c$;

R$^5$ is (a) cyclopropyl, cyclobutyl, cyclopentyl, cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl or thienyl, each of which is optionally substituted with 1 to 3 groups represented by R$^{15}$ or (b) bicyclooctanyl, decahydronaphthyl, octahydroindenyl, dihydronaphthalenyl, tetrahydronaphthalenyl, dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydrobenzisoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, chromanyl, isochromanyl, chromenyl, isochromenyl, naphthyl, anthracenyl, fluorenyl, indanyl, indenyl, carbazolyl, benzimidazolyl, benzothienyl, benzofuranyl, isobenzofuranyl, indolyl, isoindolyl, benzotriazolyl, benzothiazolyl, benzoxazolyl, benzisoxazolyl, quinolinyl, isoquinolinyl, indazolyl or acridinyl, each of which is optionally substituted with 1 to 3 groups represented by R$^{16}$;

R$^{13}$ is H and R$^{14}$ is —H, (C$_1$-C$_6$)alkyl, OR$^c$, —(C$_1$-C$_3$)alkylene-OR$^c$, —(C$_1$-C$_3$)alkylene-OH, a cycloalkyl selected from cyclopropyl, cyclobutyl, cyclopentyl and cyclohexyl, a —O-cycloalkyl selected from —O-cyclopropyl, —O-cyclobutyl, and —O-cyclopentyl, —O-cyclohexyl, or a heterocycloalkyl selected from morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl and tetrahydrothiopyranyl, provided that $R^{13}$ and $R^{14}$ are not both —$OR^c$, wherein each of the —O-cycloalkyl, cycloalkyl or heterocycloalkyl groups is optionally substituted with a $(C_1-C_3)$alkyl; and $R^c$ is —H, or $(C_1-C_6)$alkyl;

each $R^{15}$ is independently selected from halogen, —CN, —$NO_2$, =O, —$OR^c$, —$NR^aR^b$, —C(=O)$OR^c$, —OC(=O)$OR^c$, —C(=O)$NR^eR^f$, —$NR^dC$(=O)$R^e$, —$NR^d$(C=O)$OR^c$, —O(C=O)$NR^eR^f$, —$NR^d$(C=O)$NR^eR^f$, —C(=O)$R^e$, $(C_1-C_6)$alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, benzyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; wherein the $(C_1-C_6)$alkyl represented by $R^{15}$ is optionally substituted with a substituent selected from -halogen, —$OR^c$, $(C_1-C_6)$alkyl, $(C_1-C_3)$ alkoxy, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; and each $R^{16}$ is independently selected from halogen, —$OR^c$, —$NR^aR^b$, —C(=O)$OR^c$, —C(=O)$NR^eR^f$, —$NR^dC$(=O)$R^e$, —C(=O)$R^e$, $(C_1-C_6)$alkyl, phenyl, phenyl$(C_1-C_3)$alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; and values and alternative values for the remainder of the variables are as described for structural formula (I) or in the first, second, or twelfth embodiment.

In a fourteenth embodiment, for compound represented by any one of structural formulae (I), (I-A1)-(I-F2), (I-G1a)-(I-H2b), or (I-J1)-(I-J2), $R^1$ is selected from —H, -halogen, —$OCH_3$, —$N(CH_3)_2$, —$S(O)_2CH_3$, or methyl.

$R^5$ is cyclopentyl, cyclohexyl, morpholinyl, pyrrolidinyl, piperidinyl, dihydropyridinyl, tetrahydropyridinyl, dihydropyrimidinyl, tetrahydropyrimidinyl, phenyl, furanyl, imidazolyl, pyrrolyl, pyridyl, pyrimidinyl, thiazolyl, or thienyl, each of which is optionally substituted with 1 to 3 groups represented by $R^{15}$ or (b) chromanyl, chromenyl, dihydroindolyl, dihydroisoindolyl, dihydrobenzothienyl, dihydrobenzofuranyl, dihydroisobenzofuranyl, dihydrobenzotriazolyl, dihydroquinolinyl, tetrahydroquinolinyl, dihydroisoquinolinyl, tetrahydroisoquinolinyl, dihydrobenzisoxazolyl, naphthyl, anthracenyl, fluorenyl, indanyl, indenyl, dihydronaphthalene, tetrahydronaphthalene, carbazolyl, benzimidazolyl, benzothienyl, benzofuranyl, isobenzofuranyl, indolyl, quinolinyl, isoquinolinyl or isoindolyl, each of which is optionally substituted with 1 to 3 groups represented by $R^{16}$;

$R^{13}$ is —H and $R^{14}$ is —H, $(C_1-C_6)$alkyl, cyclopropyl, cyclobutyl, cyclopentyl, cyclohexyl, —O-cyclopropyl, —O-cyclobutyl, —O-cyclopentyl, —O-cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl or tetrahydrothiopyranyl;

$R^{15}$ is independently selected from halogen, —$OR^c$, —$NR^aR^b$, and $(C_1-C_6)$alkyl;

each $R^{16}$ is independently selected from $(C_1-C_6)$alkyl; and m is 1; and values and alternative values for the remainder of the variables are as described for structural formula (I) or in the first, second, twelfth, or thirteen embodiment.

In a fifteenth embodiment, for compound represented by any one of structural formulae (I), (I-A1)-(I-F2), (I-G1a)-(I-H2b), or (I-J1)-(I-J2), $R^5$ is cyclohexyl, phenyl, pyridyl, pyrimidinyl, thiazolyl, or thienyl, each of which is optionally substituted with 1 to 3 groups selected from methyl, ethyl, propyl, halogen, hydroxymethyl, hydroxyethyl, methoxy, ethoxy, and —$(CH_2)_{0-2}$-morpholinyl; and values and alternative values for the remainder of the variables are as described for structural formula (I) or in the first, second, third, fourth, fifth, sixth, seventh, eighth, ninth, tenth, eleventh, twelfth, thirteenth, or fourteenth embodiment.

Alternatively, in a sixteenth embodiment, for compound represented by any one of structural formulae (I), (I-A1)-(I-F2), (I-G1a)-(I-H2b), or (I-J1)-(I-J2), $R^5$ is cyclohexyl, phenyl, pyridyl, pyrimidinyl, thiazolyl, or thienyl, each of which is optionally substituted with 1 to 3 groups selected from methyl, ethyl, propyl, halogen, and —$(CH_2)_{0-2}$-morpholinyl; and values and alternative values for the remainder of the variables are as described for structural formula (I) or in the first, second, third, fourth, fifth, sixth, seventh, eighth, ninth, tenth, eleventh, twelfth, thirteenth, or fourteenth embodiment.

In a seventeenth embodiment, for compound represented by any one of structural formulae (I), (I-A1)-(I-F2), (I-G1a)-(I-H2b), $R^{14}$ is —H, methyl, ethyl, propyl, butyl, isopropyl, isobutyl, hydroxymethyl, hydroxyethyl, hydroxypropyl, methoxy, ethoxy, propoxy, methoxymethyl, methoxyethyl, methoxypropyl, cyclopropyl, cyclobutyl, cyclopentyl, cyclohexyl, —O-cyclopropyl, —O-cyclobutyl, —O-cyclopentyl, —O-cyclohexyl, morpholinyl, oxetanyl, tetrahydrofuryl, tetrahydropyranyl, azetidinyl, pyrrolidinyl, piperidyl, wherein the morpholinyl, tetrahydrofuryl, tetrahydropyranyl, pyrrolidinyl, or piperidyl are optionally substituted with methyl; and values and alternative values for the remainder of the variables are as described for structural formula (I) or in the first, second, third, fourth, fifth, sixth, seventh, eighth, ninth, tenth, eleventh, twelfth, thirteenth, fourteenth, fifteenth, or sixteenth embodiment.

Alternatively, in a eighteenth embodiment, for compound represented by any one of structural formulae (I), (I-A1)-(I-F2), (I-G1a)-(I-H2b), or (I-J1)-(I-J2), $R^{14}$ is —H, butyl, isopropyl, isobutyl, cyclopropyl, cyclopentyl, or pyrrolidinyl;

and values and alternative values for the remainder of the variables are as described for structural formula (I) or in the first, second, third, fourth, fifth, sixth, seventh, eighth, ninth, tenth, eleventh, twelfth, thirteenth, fourteenth, fifteenth, or sixteenth embodiment.

In certain embodiments, the present teachings provide the compounds depicted and/or described by name in the Exemplification, as well as neutral forms and pharmaceutically acceptable salts thereof.

The term "alkyl" used alone or as part of a larger moiety, such as "alkoxy", "haloalkyl", "cycloalkylalkyl", "heterocycloalkylalkyl", "aralkyl", "heteroaralkyl" and the like, means saturated aliphatic straight-chain or branched monovalent hydrocarbon radical. Unless otherwise specified, an alkyl group typically has 1-6 carbon atoms, i.e., $(C_1-C_6)$alkyl. As used herein, a "$(C_1-C_6)$alkyl" group means a radical having from 1 to 6 carbon atoms in a linear or branched arrangement.

An "alkylene group" is a saturated aliphatic branched or straight-chain divalent hydrocarbon radical. Unless otherwise specified, an alkylene group typically has 1-6 carbon atoms, i.e., $(C_1-C_6)$alkylene.

"Alkenyl" means branched or straight-chain monovalent hydrocarbon radical containing at least one double bond. Alkenyl may be mono or polyunsaturated, and may exist in the E or Z configuration. Unless otherwise specified, an alkenyl group typically has 2-6 carbon atoms, i.e., $(C_2-C_6)$alkenyl. For example, "$(C_2-C_6)$alkenyl" means a radical having from 2-6 carbon atoms in a linear or branched arrangement.

"Alkynyl" means branched or straight-chain monovalent hydrocarbon radical containing at least one triple bond. Unless otherwise specified, an alkynyl group typically has 2-6 carbon atoms, i.e., $(C_2-C_6)$alkynyl. For example, "$(C_2-C_6)$alkynyl" means a radical having from 2-6 carbon atoms in a linear or branched arrangement.

"Alkoxy" means an alkyl radical attached through an oxygen linking atom, represented by —O-alkyl. For example, "$(C_1-C_4)$alkoxy" includes methoxy, ethoxy, propoxy, and butoxy.

The terms "haloalkyl" and "haloalkoxy" means alkyl or alkoxy, as the case may be, substituted with one or more halogen atoms. The term "halogen" means F, Cl, Br, or I. Preferably the halogen in a haloalkyl or haloalkoxy is F.

The term "aryl group" used alone or as part of a larger moiety as in "aralkyl", "aralkoxy", or "aryloxyalkyl", means an aromatic hydrocarbon ring system. The term "aryl" may be used interchangeably with the terms "aryl ring" "aromatic ring", "aryl group" and "aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

"Cycloalkyl" means an aliphatic non-aromatic cyclic hydrocarbon radical. It can be monocyclic, bicyclic, polycyclic (e.g., tricyclic), or fused. For example, monocyclic $(C_3-C_8)$cycloalkyl means a radical having from 3-8 carbon atoms arranged in a monocyclic ring. A $(C_3-C_8)$cycloalkyl includes, but is not limited to, cyclopropyl, cyclobutyl, cyclopentyl, cyclohexyl, cycloheptyl and cyclooctyl.

"Heterocycloalkyl" means a saturated or unsaturated non-aromatic 4-12 membered ring radical optionally containing one or more double bonds. It can be monocyclic, bicyclic, tricyclic, or fused. The heterocycloalkyl contains 1 to 4 heteroatoms, which may be the same or different, selected from N, O or S. The heterocycloalkyl ring optionally contains one or more double bonds and/or is optionally fused with one or more aromatic rings (e.g., phenyl ring). The term "heterocycloalkyl" is intended to include all the possible isomeric forms. Examples of heterocycloalkyl include, but are not limited to, morpholinyl, thiomorpholinyl, pyrrolidinonyl, pyrrolidinyl, piperidinyl, piperazinyl, hydantoinyl, valerolactamyl, oxiranyl, oxetanyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, and tetrahydrothiopyranyl. Examples of polycyclic heterocycloalkyl groups include dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, dihydrobenzisoxazolyl, chroman, chromene, isochroman and isochromene.

The term "heteroaryl", "heteroaromatic", "heteroaryl ring", "heteroaryl group", "heteroaromatic ring", and "heteroaromatic group", are used interchangeably herein.

"Heteroaryl" when used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), isothiazolyl, triazolyl (e.g., 2-triazolyl, 5-triazolyl), tetrazolyl (e.g., tetrazolyl), and thienyl (e.g., 2-thienyl, 3-thienyl). Examples of polycyclic aromatic heteroaryl groups include carbazolyl, benzimidazolyl, benzothienyl, benzofuranyl, isobenzofuranyl, indolyl, benzotriazolyl, benzothiazolyl, benzoxazolyl, quinolinyl, isoquinolinyl, indazolyl, isoindolyl, acridinyl, or benzisoxazolyl. A "substituted heteroaryl group" is substituted at any one or more substitutable ring atom, which is a ring carbon or ring nitrogen atom bonded to a hydrogen.

Unless otherwise indicated, suitable substituents for a substituted alkyl, cycloalkyl, heterocycloalkyl, aryl group and heteroaryl group include the groups represented by halogen, —$OR^c$, —$NR^aR^b$, —$S(O)_iR^c$, —$NR^dS(O)_iR^c$, —$S(O)_iNR^e R^f$, —$C(=O)OR^c$, —$OC(=O)OR^c$, —$C(=S)OR^c$, —$O(C=S)R^c$, —$C(=O)NR^eR^f$, —$NR^dC(=O)R^c$, —$C(=S)NR^eR^f$, —$NR^dC(=S)R^c$, —$NR^d(C=O)OR^c$, —$O(C=O)NR^eR^f$, —$NR^d(C=S)OR^c$, —$O(C=S)NR^eR^f$, —$NR^d(C=O)NR^eR^f$, —$NR^d(C=S)NR^eR^f$, —$C(=S)R^c$, —$C(=O)R^c$, $(C_1-C_6)$alkyl, cycloalkyl, cycloalkyl$(C_1-C_3)$alkyl, heterocycloalkyl, heterocycloalkyl$(C_1-C_3)$alkyl, aryl, aryl$(C_1-C_3)$alkyl, heteroaryl and heteroaryl$(C_1-C_3)$alkyl, wherein $R^a$, $R^b$, $R^c$, $R^d$, $R^e$ and $R^f$ are described above for structural formula (I). Each of the $(C_1-C_6)$alkyl, cycloalkyl, cycloalkyl(C$_1$-C$_3$)alkyl, heterocycloalkyl, heterocycloalkyl (C$_1$-C$_3$)alkyl, aryl, aryl(C$_1$-C$_3$)alkyl, heteroaryl and heteroaryl(C$_1$-C$_3$)alkyl substituents is optionally substituted with halogen, —NO$_2$, —CN, —NR$^d$C(=O)R$^c$, —NR$^g$R$^h$, (C$_1$-C$_3$)alkyl, halo(C$_1$-C$_3$)alkyl, (C$_1$-C$_3$)alkoxy(C$_1$-C$_3$)alkyl, (C$_1$-C$_3$)alkoxy and halo(C$_1$-C$_3$)alkoxy, wherein R$^g$ and R$^h$ are as described above for structural formula (I). Suitable substituents for a substituted alkyl, cycloalkyl, heterocycloalkyl can also include =O. In certain embodiments, suitable substituents include alkyl, haloalkyl, alkoxy, haloalkoxy, cyano, nitro and halogen.

Regarding connectivity, an "arylalkyl" moiety, for example, refers to an alkyl group substituted with an aryl group (e.g., phenylmethyl (i.e., benzyl)). Similarly, a "heteroarylalkyl" moiety refers to an alkyl group substituted with a heteroaryl group.

The present teachings also include various isomers and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers).

Certain of the compounds described herein may exist in various stereoisomeric or tautomeric forms. Stereoisomers are compounds which differ only in their spatial arrangement. The present teachings encompass all such forms, including compounds in the form of essentially pure enantiomers, racemic mixtures and tautomers, which includes forms not depicted structurally. When a disclosed compound is named or depicted by structure without indicating stereochemistry, it is understood that the name or structure encompasses all possible stereoisomers, tautomers, geometric isomers or a combination thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

In one embodiment, the compounds described herein are TTK inhibitors, and are useful for treating diseases associated with TTK, such as cancer.

Another aspect of the present teachings relates to a method of treating a subject with cancer comprising administering to the subject an effective amount of a compound described herein. In one embodiment, the compounds described herein inhibit the growth of a tumor. For example, the compounds described herein inhibit the growth of a tumor that overexpresses TTK.

Cancers that can be treated (including reduction in the likelihood of recurrence) by the methods of the present teachings include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer, and renal cancer. In one embodiment, the cancer is lung cancer, colon cancer, brain cancer, neuroblastoma, prostate cancer, melanoma, glioblastoma multiform or ovarian cancer. In another embodiment, the cancer is lung cancer, breast cancer, colon cancer, brain cancer, neuroblastoma, prostate cancer, melanoma, glioblastoma multiform or ovarian cancer. In yet another embodiment, the cancer is breast cancer, colon cancer, and ovarian cancer. In yet another embodiment, the cancer is colon cancer and ovarian cancer. In yet another embodiment, the cancer is a breast cancer. In yet another embodiment, the cancer is a basal sub-type breast cancer or a luminal B sub-type breast cancer. In yet another embodiment, the cancer is a basal sub-type breast cancer that overexpresses TTK. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyo sarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

In some embodiments, the present teachings provide methods of inhibiting the growth of tumor-initiating cells or reducing the likelihood of recurrence of a cancer in a subject who is undergoing an anti-cancer therapy. The method comprises the steps of:

a) assessing the subject to determine whether the cancer is in remission; and b) if the cancer is in remission; then administering to the subject an effective amount of a TTK inhibitor (e.g., a compound represented by structural formula (I)). If the cancer is not in remission, the method optionally further comprises the step of continuing the anti-cancer therapy until the cancer goes into remission and then the step b) of administering an effective amount of a TTK inhibitor (e.g., a compound represented by structural formula (I)).

As used herein, the term "tumor-initiating cells" or "TICs" refer to cells present within some tumors that possess the ability to self-renew and proliferate. These cells are sometimes called cancer stem cells (CSCs) and may be observed to share certain characteristics with normal stem cells, including a stem cell-like phenotype and function. In some embodiments, TICs are characterized by their ability to form tumors after xenotransplantation in immunodeficient mice.

In some embodiments, the present teachings provide methods of inhibiting the growth of tumor-initiating cells or reducing the likelihood of recurrence of a cancer in a subject whose cancer is in remission comprising administering to the subject an effective amount of a TTK inhibitor (e.g, a compound represented by structural formula (I)).

In some embodiments, e.g., where the subject is being treated to reduce the likelihood of recurrence of a cancer, the subject has already been treated with an anti-cancer therapy. Alternatively, the subject has already been treated with an anti-cancer therapy and the subject is in remission.

In some embodiments, the present teachings provide methods of treating a subject with a cancer comprising administering to the subject an effective amount of a compound represented by structural formula (I) in combination with an effective anti-cancer therapy. In one embodiment, the cancer is a metastatic cancer. A "metastatic cancer" is a cancer that has spread from its primary site to other parts of the body.

In another embodiment, the present teachings are directed to a method of treating a subject with a drug-resistant cancer. A "drug-resistant cancer" is a cancer that is not responsive to one, two, three, four, five or more drugs that are typically used for the treatment of the cancer. In one embodiment, the drug-resistant cancer is mediated by the growth of tumor-initiating cells.

The term "inhibiting the growth of tumor-initiating cells" refers to preventing or decreasing the rate of the proliferation and/or survival of the tumor-initiating cells.

As used herein, the term "reducing the likelihood of recurrence of a cancer" means partially or totally inhibiting, preventing or delaying the return of a cancer at or near a primary site and/or at a secondary site after a period of remission. It also means that the cancer is less likely to return with treatment described herein than in its absense.

As used herein, the term "remission" refers to a state of cancer, wherein the clinical symptoms or indicators associated with a cancer have disappeared or cannot be detected, typically after the subject has been successfully treated with an anti-cancer therapy.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

Suitable methods known in the art can be used for assessing a subject to determine whether the cancer is in remission. For example, the size of the tumor and/or tumor markers, usually proteins associated with tumors, can be monitored to determine the state of the cancer. Size of the tumor can be monitored with imaging devices, such as X-ray, MRI, CAT scans, ultrasound, mammography, PET and the like or via biopsy.

For methods described herein, e.g., coadministration methods, the anti-cancer therapy is selected from the group consisting of surgery, radiation therapy, immunotherapy, endocrine therapy, gene therapy and administration of an anti-cancer agent. Alternatively, the anti-cancer therapy is radiation therapy. In another alternative, the anti-cancer therapy is immunotherapy. In another alternative, the anti-cancer therapy is administration of an anti-cancer agent. In yet another alternative, the anti-cancer therapy is surgery.

Radiation therapy is the use of radiation to kill, destroy or treat the cancers. Exemplary radiation therapy includes, but is not limited to, gamma-radiation, neutron beam radiotherapy, electron beam radiotherapy, proton therapy, brachytherapy, and radioiosotope thereapy (i.e., systemic radioactive isotopes therapy), An endocrine therapy is a treatment that adds, blocks or removes hormones. For example, chemotherapeutic agents that can block the production or activity of estrogen have been used for treating breast cancer. In addition, hormonal stimulation of the immune system has been used to treat specific cancers, such as renal cell carcinoma and melanoma. In one embodiment, the endocrine therapy comprises administration of natural hormones, synthetic hormones or other synthetic molecules that may block or increase the production of the body's natural hormones. In another embodiment, the endocrine therapy includes removal of a gland that makes a certain hormone.

As use herein, a gene therapy is the insertion of genes into a subject's cell and biological tissues to treat diseases, such as cancer. Exemplary gene therapy includes, but is not limited to, a germ line gene therapy and a somatic gene therapy.

Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANORE™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXI™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXA™ which is a chimeric anti-CD20 IgG1 antibody (IDEC Pharm/Genentech, Roche/Zettyaku); LYMPHOCID™ which is a humanized anti-CD22 IgG antibody (Immunomedics); LYMPHOCID™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALI™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVAT™ is a humanized anti-CD40L IgG antibody (Biogen); ANTEGRE™ is a humanized anti-VLA-4 IgG antibody (Elan); and CAT-152 is a human anti-TGF-β$_2$ antibody (Cambridge Ab Tech).

Immunotherapies that can be used in the present teachings include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Alternatively, the anti-cancer therapy described herein includes administration of an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agent suitable for use in the methods described herein include any anti-cancer agents that have been approved for the treatment of cancer. In one embodiment, the anti-cancer agent includes, but is not limited to, a targeted antibody, an angiogenisis inhibitor, an alkylating agent, an antimetabolite, a vinca alkaloid, a taxane, a podophyllotoxin, a topoisomerase inhibitor, a hormonal antineoplastic agent and other antineoplastic agents.

Examples of alkylating agents useful in the methods of the present teachings include but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful in the methods of the present teachings include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of plant alkaloids and terpenoids or derivatives thereof include, but are not limited to, vinca alkaloids (e.g., vincristine, vinblastine, vinorelbine, vindesine), podophyllotoxin, and taxanes (e.g., paclitaxel, docetaxel). Examples of a topoisomerase inhibitor includes, but is not limited to, irinotecan, topotecan, amsacrine, etoposide, etoposide phosphate and teniposide. Examples of antineoplastic agents include, but are not limited to, actinomycin, anthracyclines (e.g., doxorubicin, daunorubicin, valrubicin, idarubicin, epirubicin), bleomycin, plicamycin and mitomycin.

In one embodiment, the anti-cancer agents that can be used in the present teachings include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anti-cancer agents/drugs that can be used in the present teachings include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex;

formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

In one embodiment, the anti-cancer agents that can be used in methods described herein are selected from the group consisting of paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan and a combination thereof.

In one embodiment, the anti-cancer agent and the compound represented by structural formula (I) are administered contemporaneously. When administered contemporaneously, the anti-cancer agent and the compound can be administered in the same formulation or in different formulations. Alternatively, the compound and the additional anti-cancer agent are administered separately.

In one embodiment, the subject in the methods described herein has not been previously treated with a TTK inhibitor (e.g., the compound represented by structural formula (I)).

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control. Specifically, "treating a subject with a cancer" includes achieving, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein (including treating a subject with a cancer or reducing the likelihood of recurrence of a cancer), a "treatment" or dosing regime of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

As used herein, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in H$_2$O suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

Compounds described herein may be prepared using the reaction routes and syntheses described below, employing the techniques available in the art using starting materials that are readily available.

In one general synthetic process, compounds described herein can be prepared according to the following reaction Scheme 1. Halogenation of an appropriately substituted indazole wherein the indazole is substituted as defined herein provides intermediate 1 that can be reacted with a suitable cross coupling partner, ArMet, in the presence of a metal catalyst (e.g., ArBpin/PdCl$_2$(dppf)/Na$_2$CO$_3$/EtOH/PhMe/mw/120° C.).

Scheme 1

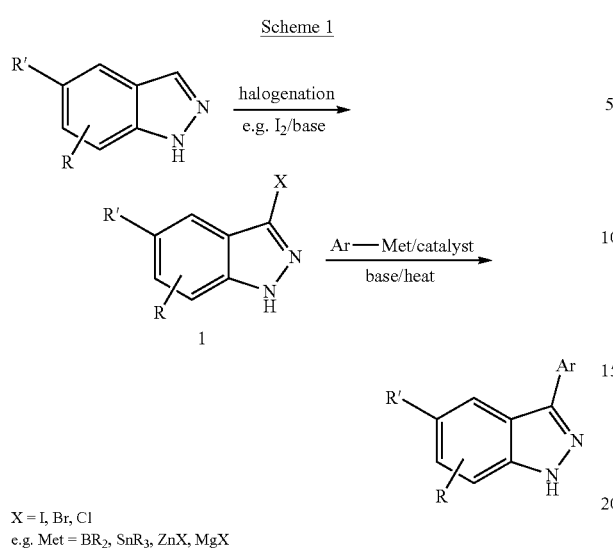

X = I, Br, Cl
e.g. Met = BR$_2$, SnR$_3$, ZnX, MgX
catalyst = Pd, Ni

Alternatively, haloindazole 2 can be converted into a 3-(trialkylstannyl)-1H-indazole that can be subjected to Stille-type cross-coupling reaction as shown in Scheme 2 (e.g., 1. Me$_6$Sn$_2$/Pd(PPh$_3$)$_4$/PhMe 2. ArI/Pd(PPh$_3$)$_4$/CuI/THF ref. WO200102369).

Scheme 2

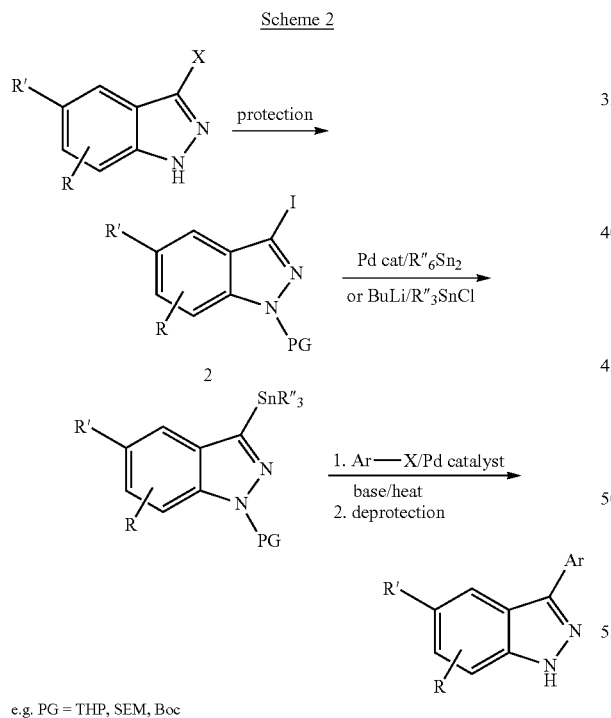

e.g. PG = THP, SEM, Boc

Compounds described herein can also be prepared according to the general procedure shown in Scheme 3. Aminoindazole 3 is protected by a suitable aniline protecting group such as a Boc group followed by iodination with I$_2$/K$_2$CO$_3$. A sequence of Suzuki-Miyaura cross coupling and removal of the protecting group yields aniline 4 that can be reacted with a variety of electrophilic reagents (e.g., R—NCO, R'R"NH/ phosgene or triphosgene, ROH/triphosgene, RNHSO$_2$NHC(=O)CH$_2$CH$_2$Cl, RSO$_2$Cl, RC(=O)R'/reducing agent, RCO$_2$Cl or RCO$_2$H/coupling reagent: TBTU, EDC, DCC, HATU, pyBOP) leading to preparation of substituted anilines, ureas, sulfonamides, sulfamides amides and carbamates.

Scheme 3

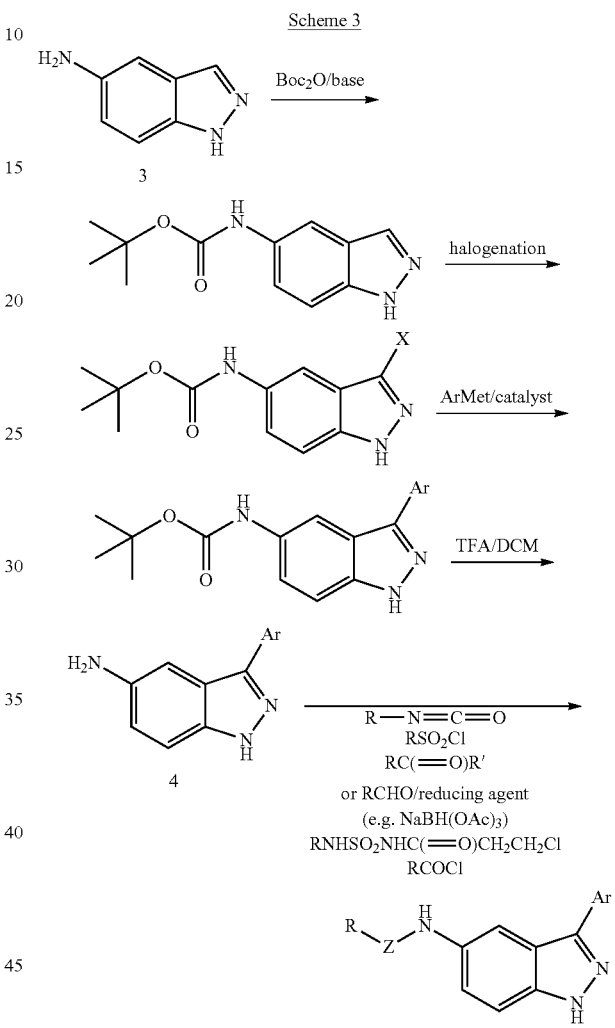

Alternatively, 5-nitro-1H-indazole can be halogenated and reduced to provide 3-halo-5-amino indazoles 5 that can be subjected to an amide formation followed by Pd-catalyzed cross-coupling (Scheme 4).

Scheme 4

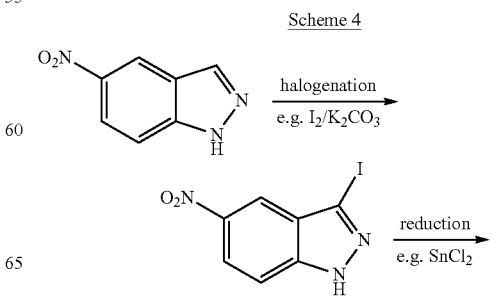

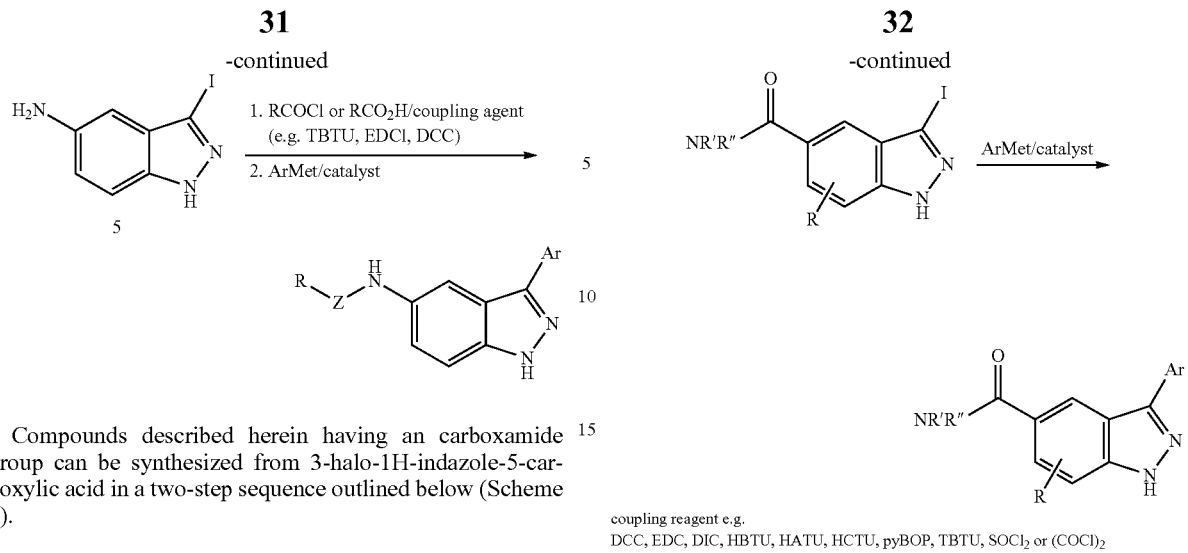

Compounds described herein having an carboxamide group can be synthesized from 3-halo-1H-indazole-5-carboxylic acid in a two-step sequence outlined below (Scheme 5).

Scheme 5

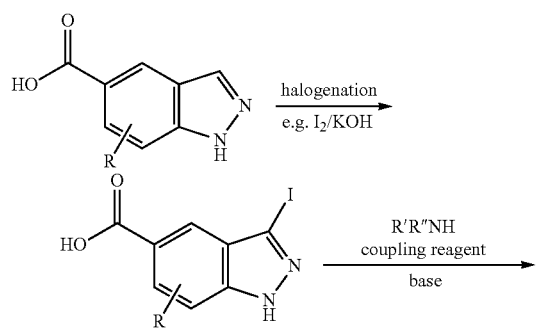

coupling reagent e.g.
DCC, EDC, DIC, HBTU, HATU, HCTU, pyBOP, TBTU, SOCl$_2$ or (COCl)$_2$ Compounds described herein can be prepared according to the general procedures shown in Scheme 6. 6-Tosyl-2-oxa-6-azaspiro[3.3]heptane 6 can be synthesized in one step using p-toluenesulfonamide and trihalopentaerythitol in the presence of strong base (ref: WO2011/59839). Removal of tosyl moiety resulted in the desired 2-oxa-6-azaspiro[3.3]heptane 7 (Scheme 6A). 2,6-diazaspiro[3.3]heptane analogues 8 can also be synthesized from intermediate 6. Oxetane opening of 6 with acid, followed by halogenation, displacement of primary amine, and deprotection of tosylate yields the desired diazaspiro[3.3]heptane analogue 8 (ref: *Org. Lett.* 2008, 10, 3525). Alternatively, di-Boc-protected diazaspiro[3.3]heptane 9 can be made in one step outlined in Scheme 6B (ref: WO2010/108268).

Scheme 6

A.

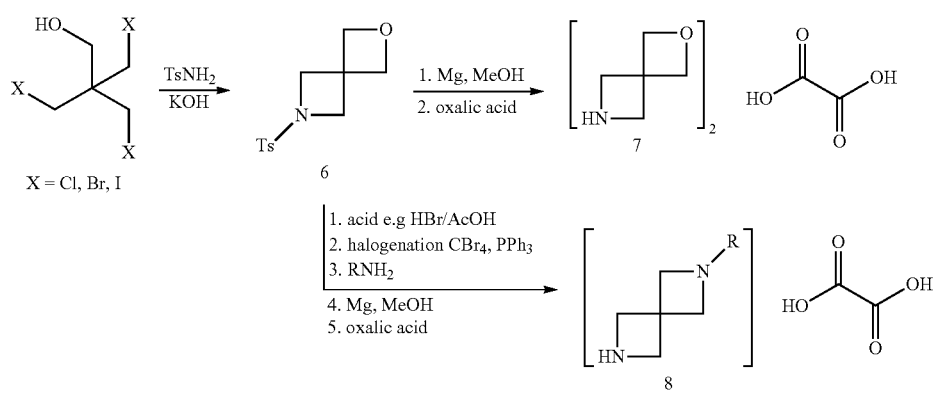

B.

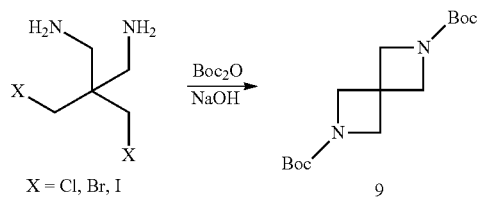

The intermediate boronic esters described herein can be prepared as outlined in Scheme 7. Aniline-based boronic ester can be prepared via Cu(I) catalyzed amination of an appropriately substituted dihalobenzene followed by borylation with a suitable borylating agent (HBpin or (Bpin)$_2$) in the presence of a Pd-catalyst (e.g. Cl$_2$Pd(CH$_3$CN)$_2$ or Cl$_2$Pddppf). Alternatively, aniline 10 can be synthesized using Pd-catalyzed amination (also known as the Buchwald-Hartwig cross coupling reaction, e.g. Pd(dba)$_2$, P(o-Tolyl)$_3$, and NaO$^t$Bu; ref: *Angew. Int. Ed.* 1995, 34(12), 1348-1350).

Scheme 7

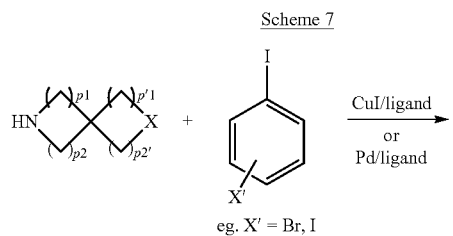

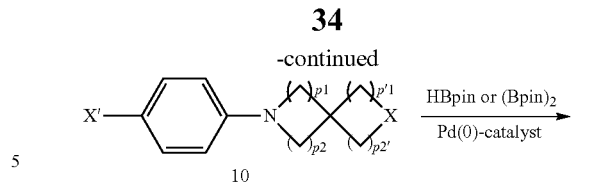

Enantiomerically pure (typically over 98% ee) 3-iodo-1H-indazole-5-carboxamides described herein can be prepared as outlined in Scheme 8 by separating racemic compounds using chiral preparative supercritical fluid chromatography (SFC).

Scheme 8

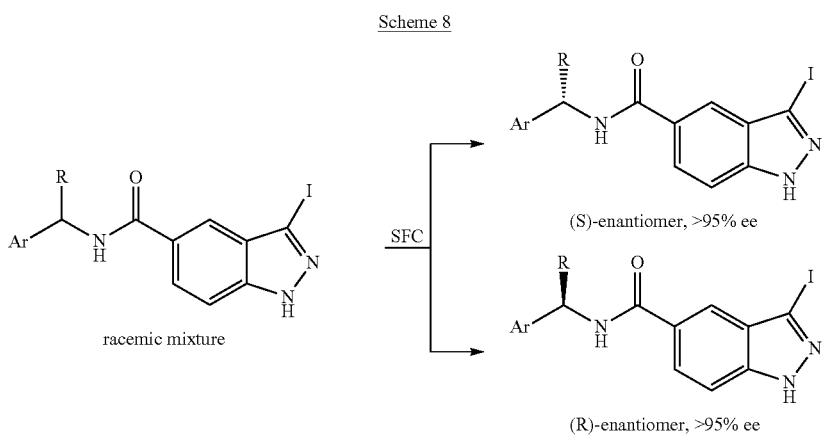

Alternatively, enantiomerically pure 3-iodo-1H-indazole-5-carboxamides can be prepared via an amide coupling using 3-halo-1H-indazole-5-carboxylic acid and enantiomerically pure amine. Such enantiomerically pure amine can be obtained by separating racemic amine using chiral preparative supercritical fluid chromatography (SFC) or recrystallization of salts with chiral acids such as tartaric acid, Mandelic acid and dibenzoyl-tartaric acid (Scheme 9).

Scheme 9

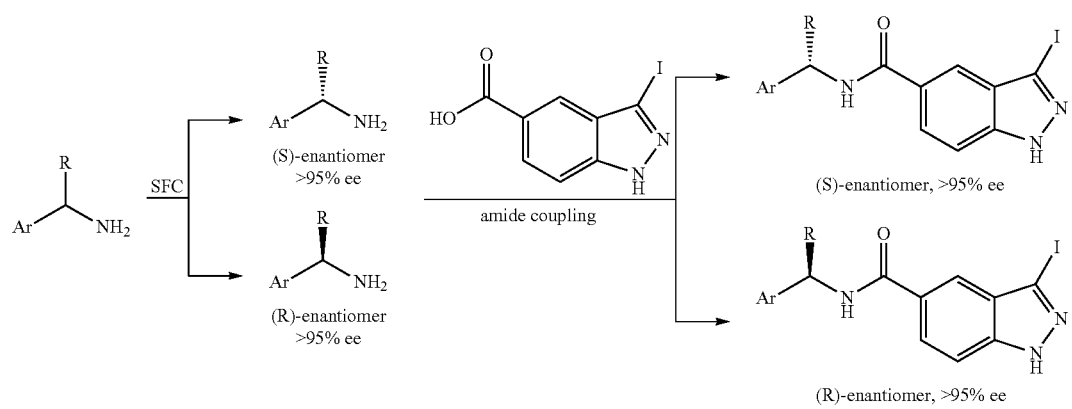

In addition, enantiomerically pure amines described herein can be synthesized using asymmetric nucleophilic addition to chiral imines (Scheme 10). In this approach, the desired chiral amine can be synthesized in two ways by switching the role of which fragment acts as a nucleophile and which acts as an electrohpile in the addition step. The chiral auxiliary serves as a chiral directing group to provide an addition product with high diastereoselectivity in general. Chiral auxiliary is then removed rendering the desired chiral amine in high enantiomeric excess. Enantiomeric excess of the amines described herein can be further improved by recrystallization.

Scheme 10

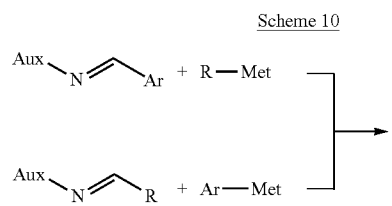

Aux = chiral auxilary
R = aliphatic group
Ar = aromatic group
Met = metal, eg. MgXr, Li, ZnX
X = halogens A variety of chiral auxiliary can be employed in the synthesis of chiral imine. A method developed by Ellman involved a condensation of tert-butylsulfinyl amide with aldehydes to provide tert-butanesulfinyl imines (Scheme 11A; ref: *Chem. Rev.* 2010, 110, 3600). Other chiral auxiliaries that are commonly employed in this approach are 1-amino-2-methoxymethyl pyrrolidine (Enders' method; ref: *Tetrahedron: Asymmetry* 1997, 8, 1895), and phenylglycinol (Pridgen's method; ref: *J. Org. Chem.* 1991, 56, 1340) (Scheme 11B).

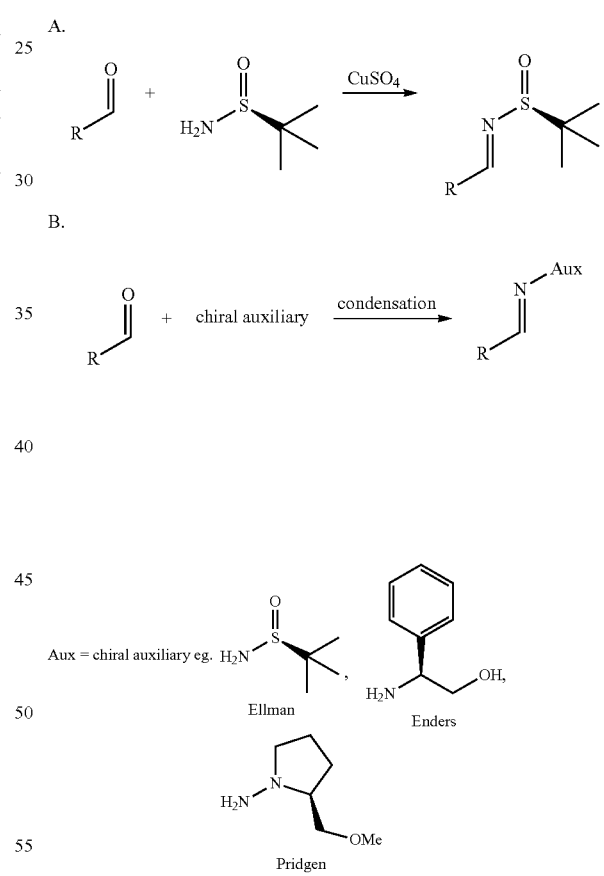

Racemic amines 11 described herein can be synthesized in three steps (Scheme 12A). Nucleophilic addition of aldehyde using organometallic reagents such as Grignard reagents, organolithiums, or organozincs resulted in secondary alcohol. Subsequent oxidation to the corresponding ketone followed by reductive amination resulted in the desired racemic amine 11. Alternatively, the desired racemic amine described herein can be obtained using a one-pot synthesis shown in Scheme 12B.

Scheme 12

A.

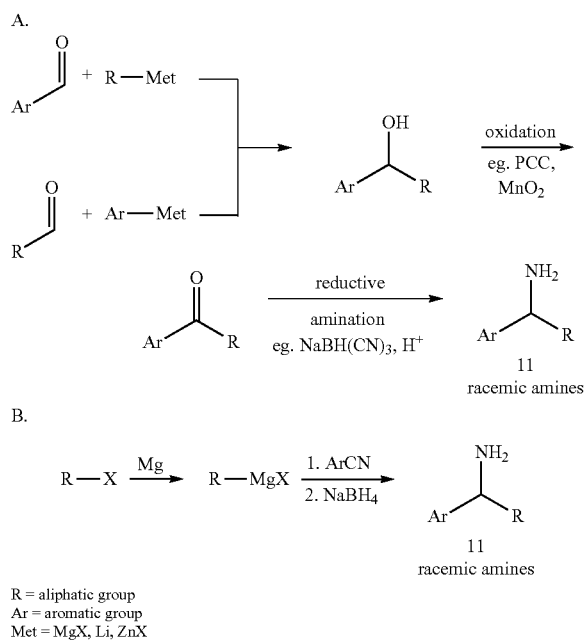

B.

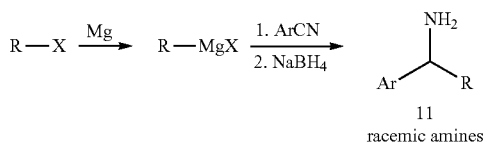

R = aliphatic group
Ar = aromatic group
Met = MgX, Li, ZnX

Compounds described herein can be prepared in a manner analogous to the general procedures described above or the detailed procedures described in the examples herein.

The invention is illustrated by the following examples which are not intended to be limiting in any way.

EXEMPLIFICATION

Example A

Synthesis

General Methods

Commercially available starting materials, reagents, and solvents were used as received. In general, anhydrous reactions were performed under an inert atmosphere such as nitrogen or Argon. PoraPak®Rxn CX refers to a commercial cation-exchange resin available from Waters.

Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000). Flash column chromatographic purification of intermediates or final products was performed using 230-400 mesh silica gel 60 from EMD chemicals or Silicycle, or purified using a Biotage Isolera with KP-SIL or HP-SIL silica cartridges, or KP-NH basic modified silica and corresponding samplets. RPReverse-phase RPHPLC purification was performed on a Varian PrepStar model SD-1 HPLC system with a Varian Monochrom 10u C-18 reverse-phase column using a of about 5-30% MeCN or MeOH/0.05% TFA—H2O to 70-90% MeCN or MeOH/0.05% TFA—H2O over a 20-40-min period at a flow rate of 30-50 mL/min. RPpurification was also performed using a Biotage Isolera equipped with a KP-C18-H column using a between 10-95% MeOH/0.1% TFA in $H_2O$. Proton NMRs were recorded on a Bruker 400 MHz spectrometer, and mass spectra were obtained using a Bruker Esquire 4000 spectrometer. Optical rotations were measured at the sodium D-line (589.44 nM) using an AA-55 polarimeter from Optical Activity Ltd with a 2.5×100 mm unjacketed stainless steel tube at given sample concentrations (c, units of g/100 mL).

Compound names were generated using the software built into ChemBioDraw Ultra version 11.0 or 12.0.

ABBREVIATIONS

Ac acetyl
aq aqueous
anh anhydrous
Ar Argon
br. Broad
BINOL 1,1'-binaphthalene-2,2'-diol
calcd calculated
d doublet (only when used within $^1$H NMR spectra)
d day
DBTA Dibenzoyl-L-tartaric acid monhyrate
DCE 1,2-dichloroethane
DCM dichloromethane
DIPEA diisopropylethylamine
DME 1,2-dimethoxyethane
DMF N,N-dimethylformamide
DMSO dimethylsulfoxide
dppf 1,1'-bis(diphenylphosphino) ferrocene
e.e. enantiomeric excess
h hour
HPLC high performance liquid chromatography
HATU 2-(1H-7-azabenzotriazol-1-yl)-1,1,3,3-tetramethyluronium hexafluorophosphate
IPA isopropyl alcohol
LC-MS liquid chromatography coupled to mass spectrometry
min minute
m multiplet
MS ESI mass spectra, electrospray ionization
NBS N-Bromosuccinimide
NMR nuclear magnetic resonance
O/N overnight
PCC pyridinium chlorochromate
pin pinacol
prep preparative
RBF round bottomed flask
rt room temperature
$R_t$ retention time
s singlet
satd saturated
SFC supercritical fluid chromatography
SPE solid phase extraction
S-Phos 2-dicyclohexylphosphino-2',6'-dimethoxybiphenyl
t triplet
TBTU O-(benzotriazol-1-yl)-N,N,N',N'-tetramethyluronium tetrafluoroborate
temp. temperature
TEA triethylamine
TFA trifluoroacetic acid
TLC thin layer chromatography
THF tetrahydrofuran
xs excess
Preparation of Starting Materials
Method A (Amide Coupling)

A DMF solution of 3-iodo-1H-indazol-5-amine 2,2,2-trifluoroacetate (1.0 equiv), DIPEA (3 equiv) and $RCO_2H$ (1.05 equiv) at 0° C. was treated with TBTU (1.05 equiv) added in one portion. The reaction was stirred allowing slowly to warm to rt. After several h or overnight stirring the crude reaction was subsequently diluted with $H_2O$. In the majority of examples a filtration and washing (H₂O) of the precipitate provided the desired material with the required purity or alternatively the material was purified directly by prepHPLC or/and flash chromatography.

Alternatively, a DMF solution of 3-iodo-1H-indazole-5-carboxylic acid (1.0 equiv), DIPEA (3 equiv) and RR'NH (1.05 equiv) at 0° C. or rt was treated with TBTU (1.05 equiv) added in one portion. The reaction was stirred allowing slowly to warm to rt. After several h or overnight stirring the crude reaction was subsequently diluted with H₂O. In the majority of examples a filtration and washing (H₂O) of the precipitate provided the desired material with the required purity or alternatively the material was purified directly by prepHPLC or/and flash chromatography.

Method B (Iodination)

To a cooled (0° C.) DMF solution indazole (1.0 equiv) and K₂CO₃ or KOH (~3 equiv) was added I₂ (2-4 equiv) in one portion. The reaction was stirred with cooling or rt for several h and then was treated with xs 10% aq NaHSO₃ and subsequently diluted with H₂O. In the majority of examples a filtration and washing (H₂O) of the precipitate provided the desired material with the required purity.

Method C1 (Suzuki-Miyaura Cross Coupling)

A mixture of 3-iodo-1H-indazole (1.0 equiv), aryl boronic acid or boronate ester (1-1.2 equiv), base and palladium catalyst (0.05-0.10 equiv e.g. Pd(PPh₃)₄ and PdCl₂dppf.DCM) in solvents was degassed with Ar and heated sealed in a Biotage microwave reactor. The product was partitioned between EtOAc and H₂O, dried (Na₂SO₄ or MgSO₄), filtered, and concentrated to dryness. The crude product was purified by flash chromatography (normal phase using Biotage HP-SIL column with hexanes and EtOAc as eluents and reverse phase using C18 column with H₂O and MeCN as eluents) to give the title compound. In the majority of examples, further purification by trituration with MeOH was required to provide the target material.

Method C2 (Suzuki-Miyaura Cross Coupling with Pd(PPh₃))

Aq Na₂CO₃ (2 M, 3-4 mmol) was added to a mixture of 5-substituted-3-iodo-1H-indazole (1.0 mmol), aryl boronic acid or boronate ester (1.0-1.4 mmol), and Pd(PPh₃)₄ (0.05-0.10 mmol) in PhMe:EtOH (1:1, 6 mL) was heated under Ar in a Biotage microwave reactor, an oil bath or an aluminum reaction block at temperatures 100-130° C. The product was partitioned between EtOAc and H₂O, dried (Na₂SO₄ or MgSO₄), filtered, and concentrated to dryness. The crude product was purified by flash chromatography (normal phase using Biotage HP-SIL column with hexanes and EtOAc as eluents and reverse phase using a C18 column with H₂O and MeCN or MeOH with or without 0.05% TFA as eluents) to give the title compound. In the majority of examples, further purification by trituration with MeOH was required to provide the target material.

Method D (Copper Catalyzed Amination of Aryl-Hal)

A microwave vial was charged with 1,4-diiodobenzene (1.0 equiv), dialkylamine (1-1.2 equiv), BINOL (20 mol %), K₃PO₄ (2-4 equiv) and DMF. The vial was purged with Ar for 10-15 min. CuI (20 mol %) was added and the vial was then capped. The resulting mixture was stirred at rt for 2 to 4 d. The mixture was diluted with EtOAc, filtered through a cake of Celite and the filtrate was concentrated to give the crude product. Crude product was purified by flash chromatography to give the title compound.

Method E (Borylation of Aryl Halides): Using B₂Pin₂/Pd

A mixture of aryliodide (1 equiv), bis(pinacolato)diboron (1.2 to 1.5 equiv.), KOAc (3 equiv.) and DMF or DMSO was purged with Ar for 10 min. [1,1'-PdCl₂dppf*CH₂Cl₂ (3-5 mol %) was added, the vial sealed and heated at 85° C. for 2 h. The product was partitioned between EtOAc and satd aq NaHCO₃ solution, washed with brine, dried (Na₂SO₄ or MgSO₄), filtered, and concentrated to dryness. The crude product was purified by flash chromatography to give the title compound.

Method F (Reductive Amination)

NaBH₃CN (4 equiv.) was added to a solution of aryl alkyl ketone (1 equiv.) and NH₄OAc (12 equiv. in MeOH under Ar, and the reaction mixture was heated at 60° C. for 14-48 h. Aq. NaOH (2 M) was added and the product was extracted into EtOAc (3×). The combined EtOAc layer was washed with H₂O and brine, dried (MgSO₄), filtered, concentrated to dryness and used crude or purified by chromatography.

Method G (One-Pot Synthesis of Cyploroylmethanamine Using Arylnitrile)

To a microwave vial charged with Mg powder (2 equiv.) and THF was added bromocyclopropane (2 equiv.). The resulting mixture was stirred for 30 min at rt before a solution of arylnitrile (1 equiv.) in THF was added. It was microwaved 10 min at 100° C., cooled to rt and added dropwise to a cold solution of NaBH₄ (2 equiv.) in MeO at 0° C. The resulting mixture was stirred for 15 min at rt, quenched with H₂O, extracted with DCM and purified by Biotage SiO₂ column (gradient: MeOH/DCM 0-30%) to give the desired product.

Method H (Synthesis of t-butylslfinylimines)

Aryl or alkylaldehyde (1.2 eq.) was added to a stirred suspension of (S)-t-butylsulfinylamide (1.0 eq.) and flame-dried CuSO₄ (2.2 eq.) in dry CH₂Cl₂. The resulting mixture was stirred at rt for 69 h. The reaction mixture was filtered through a pad of Celite and the pad was extracted with CH₂Cl₂. The combined organic extracts were concentrated under reduced pressure yielding the crude product. Purification by repeated flash chromatography (SiO₂) using EtOAc-cyclohexane as eluent gave the desired product.

Method I (Deprotection of Sulfinamides)

A solution of HCl (2.0 M in Et₂O, 2.0 eq.) was added carefully to a stirred 0° C. solution of sulfinamide (1.0 eq.) in MeOH. After the addition was complete the cooling bath was removed and the mixture was stirred at rt for 1 h. The reaction mixture was concentrated under reduced pressure and Et₂O was added and a white precipitation formed. The precipitation was filtered off and washed with Et₂O and dried under reduced pressure yielding the crude product.

Intermediates 1-oxa-6-azaspiro[3.3]heptane

A solution of tert-butyl 1-oxa-6-azaspiro[3.3]heptane-6-carboxylate (1.0 g, 5.0 mmol) and TFA (2 mL) in DCM (10 mL) was stirred at rt for 1 h. The solvent was removed in vacuo, and the product was isolated as a TFA salt and used without further purification.

(3-(Bromomethyl)-1-(p-toluenesulfonyl)azetidin-3-yl)methanol

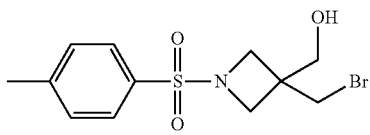 [SMILES: Cc1ccc(S(=O)(=O)N2CC(CO)(CBr)C2)cc1]

6-(p-Toluenesulfonyl)-2-oxa-6-azaspiro[3.3]heptane (7.99 g, 31.5 mmol) was suspended in Et$_2$O (300 mL) and cooled to 0° C. A solution of HBr (48% in AcOH; 10 mL) in Et$_2$O (20 mL) was added dropwise over 20 min. The resulting mixture was warmed to rt and stirred for 1 h. Reaction was monitored by LC-MS. NaHCO$_3$ (aq. satd., 200 mL) was added and the resulting phases were separated. The aq layer was extracted with Et$_2$O (100 mL) and then combined Et$_2$O layer was dried (MgSO$_4$), filtered, concentrated to dryness to give the title compound as a white solid (10.2 g, 97%). $^1$H NMR (400 MHz, CDCl$_3$) δ ppm 7.74 (d, J=8.3 Hz, 2H), 7.40 (d, J=8.0 Hz, 2H), 3.69 (d, J=4.8 Hz, 2H), 3.62 (d, J=8.5 Hz, 2H), 3.55 (d, J=8.5 Hz, 2H), 3.46 (s, 2H), 2.48 (s, 3H), 1.55 (t, J=5.0 Hz, 1H); MS ESI 333.9, 335.9 [M+H]$^+$, calcd for [C$_{12}$H$_{16}$BrNO$_3$S+H]+334.0, 336.0.

3,3-Bis(bromomethyl)-1-(p-toluenesulfonyl)azetidine

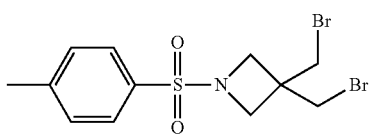 [SMILES: Cc1ccc(S(=O)(=O)N2CC(CBr)(CBr)C2)cc1]

(3-(Bromomethyl)-1-(p-toluenesulfonyl)azetidin-3-yl) methanol (10.2 g, 30.6 mmol) was dissolved in DCM (100 mL) and CBr$_4$ (16.9 g, 51 mmol) was added. The solution was cooled to 0° C. and then PPh$_3$ (13.4 g, 51 mmol) was added in one portion. The resulting mixture was stirred at 0° C. for 2 h, then warmed to rt and stirred for 4 h. Et$_2$O (100 mL) was added and the yellow precipitate was filtered. The filtrate was concentrated under reduced pressure and purification by flash chromatography (Biotage Isolera, 100 g KP-SIL, 0-30% EtOAc in hexanes) gave the title compound as colourless crystals (8.05 g, 67%). $^1$H NMR (400 MHz, CDCl$_3$) δ ppm 7.74 (d, J=8.3 Hz, 2H), 7.41 (d, J=8.0 Hz, 2H), 3.60 (s, 4H), 3.54 (s, 4H), 2.48 (s, 3H); MS ESI 398.1 [M+H]$^+$, calcd for [C$_{12}$H$_{15}$Br$_2$NO$_2$S+H]+397.9.

3,3-Bis(bromomethyl)-1-(p-toluenesulfonyl)azetidine

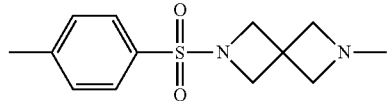

3,3-Bis(bromomethyl)-1-(p-toluenesulfonyl)azetidine (1.6 g, 4.0 mmol), 2 M methylamine in MeOH (8 mL, 4 mmol), DIPEA (3.5 mL, 20 mmol), and DMF (8 mL) were combined and sealed. The mixture was heated at 100° C. for 2 h in Biotage microwave reactor. Concentrated reaction mixture under reduced pressure and diluted with EtOAc (50 mL). Washed with NaHCO$_3$ (aq. satd. 50 mL) and brine (50 mL). The aq layer was extracted with EtOAc (50 mL). Combined the EtOAc layers, dried (MgSO$_4$), filtered, and concentrated to dryness to give the title compound as a beige solid (993 mg, 93%); $^1$H NMR (400 MHz, CDCl$_3$) δ ppm 7.71 (d, J=8.3 Hz, 2H), 7.37 (d, J=8.0 Hz, 2H), 3.83 (s, 4H), 3.14 (s, 4H), 2.46 (s, 3H), 2.22 (s, 3H); MS ESI 267.1 [M+H]$^+$, calcd for [C$_{13}$H$_{18}$N$_2$O$_2$S+H]+ 267.1.

2-Methyl-2,6-diazaspiro[3.3]heptane oxalate

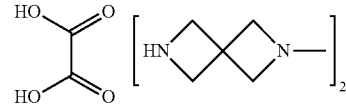

3,3-Bis(bromomethyl)-1-(p-toluenesulfonyl)azetidine (550 mg, 2 mmol) was dissolved in MeOH (20 mL) and then Mg powder (384 mg, 16 mmol) was added. The mixture was carefully sonicated for 1 h and then concentrated under reduced pressure. The mixture was suspended in Et$_2$O (100 mL) and Na$_2$SO$_4$.10H$_2$O (2 g) was added. The slurry was stirred for 1 h, then filtered, dried (Na$_2$SO$_4$), and filtered. Oxalic acid (90 mg, 1 mmol) in EtOH (0.5 mL) was added to the filtrate. The solid was filtered and dried to give the title compound as a white solid (207 mg, 66%); $^1$H NMR (400 MHz, CD$_3$OD) δ ppm 4.26 (s, 4H), 4.14 (s, 4H), 2.72 (s, 3H); MS ESI 113.1 [M+H]$^+$, calcd for [C$_6$H$_{12}$N$_2$+H]+113.1.

6-(4-Iodophenyl)-2-oxa-6-azaspiro[3.3]heptane

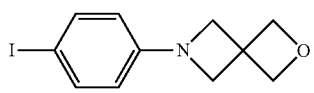

The title compound was synthesized according to General Method D, utilizing 1,4-diiodobenzene (2.5 g, 7.6 mmol), 2-oxa-6-azaspiro[3.3]heptane oxalic acid salt (1.0 g, 6.9 mmol), CuI (0.26 g, 1.4 mmol), BINOL (0.40 g, 1.4 mmol), and K$_3$PO$_4$ (4.4 g, 21 mmol) in DMF (15 mL). The mixture was diluted with EtOAc, filtered through Celite and the filtrate was concentrated. Purification by flash chromatography (Biotage Isolera, 100 g HP-SIL, 10-50% EtOAc in hexanes) gave the title compound as a yellow solid (0.78 g, 37%). $^1$H NMR (400 MHz, CDCl$_3$) δ ppm 7.47 (d, J=8.8 Hz, 2H), 6.22 (d, J=8.8 Hz, 2H), 4.82 (s, 4H), 3.98 (s, 4H); MS ESI 301.9 [M+H]$^+$, calcd for [C$_{11}$H$_{12}$INO+H]$^+$ 302.0.

The following intermediates were synthesized according to the synthesis of 6-(4-iodophenyl)-2-oxa-6-azaspiro[3.3]heptane using General Method D:

| IUPAC name | Structure | MS calculated | MS ESI [M + H]+ | Yield; Appearance; Salt form |
|---|---|---|---|---|
| 7-(4-Iodophenyl)-2-oxa-7-aza-spiro[3.5]nonane | 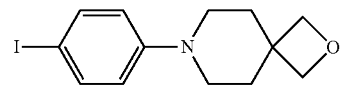 [SMILES: Ic1ccc(N2CCC3(CC2)COC3)cc1] | $[C_{13}H_{16}INO + H]^+$ 330.0 | 330.0 | 576 mg (53%); yellow solid; free base |

Starting materials: 1,4-diiodobenzene (1.1 g, 3.3 mmol), 2-oxa-7-azaspiro[3.5]nonane oxalate (0.50 g, 3.9 mmol)
$^1$H NMR (400 MHz, CDCl$_3$) δ ppm 7.51 (d, J = 8.0 Hz, 2H), 6.69 (d, J = 8.0 Hz, 2H), 4.48 (s, 4H), 3.09 (t, J = 5.5 Hz, 4H), 1.99 (t, J = 5.5 Hz, 4H)

| IUPAC name | Structure | MS calculated | MS ESI [M + H]+ | Yield; Appearance; Salt form |
|---|---|---|---|---|
| 6-(4-Iodophenyl)-2-oxa-6-aza-spiro[3.4]octane | | $[C_{12}H_{14}INO + H]^+$ 316.0 | 315.9 | 514 mg (44%); White solid; free base |

Starting materials: 1,4-diiodobenzene (1.2 g, 3.7 mmol), 2-oxa-6-azaspiro[3.4]octane oxalate (0.50 g, 4.4 mmol)
$^1$H NMR (400 MHz, CDCl$_3$) δ ppm 7.48 (d, J = 9.0 Hz, 2H), 6.34 (d, J = 9.0 Hz, 2H), 4.71 (d, J = 6.3 Hz, 2H), 4.66 (d, J = 6.3 Hz, 2H), 3.30 (t, J = 6.9 Hz, 2H), 2.32 (t, J = 6.9 Hz, 2H)

| IUPAC name | Structure | MS calculated | MS ESI [M + H]+ | Yield; Appearance; Salt form |
|---|---|---|---|---|
| 2-(4-Iodophenyl)-7-oxa-2-aza-spiro[3.5]nonane | | $[C_{13}H_{16}INO + H]^+$ 330.0 | 330.0 | 747 mg (36%); Yellow solid; free base |

Starting materials: 1,4-diiodobenzene (2.1 g, 6.2 mmol), 2-oxa-7-azaspiro[3.5]nonane oxalate (0.95 g, 7.5 mmol)
$^1$H NMR (400 MHz, CDCl$_3$) δ ppm 7.47 (d, J = 8.8 Hz, 2H), 6.23 (d, J = 8.8 Hz, 2H), 3.67 (t, J = 5.0 Hz, 4H), 3.63 (s, 4H), 1.83 (t, J = 5.3 Hz, 4H)

| IUPAC name | Structure | MS calculated | MS ESI [M + H]+ | Yield; Appearance; Salt form |
|---|---|---|---|---|
| 6-(4-Iodophenyl)-1-oxa-6-aza-spiro[3.3]heptane | | $[C_{11}H_{12}INO + H]^+$ 302.0 | 302.0 | 641 mg (42%); white solid; free base |

Starting materials: 1,4-diiodobenzene (1.8 g, 5.5 mmol), 1-oxa-6-azaspiro[3.3]heptane trifluoracetic (1.2 g, 5.5 mmol)
$^1$H NMR (400 MHz, CDCl$_3$) δ ppm 7.46 (d, J = 9.0 Hz, 2H), 6.24 (d, J = 8.8 Hz, 2H), 4.58 (t, J = 7.5 Hz, 2H), 4.09 (d, J = 9.5 Hz, 2H), 3.97 (d, J = 9.8 Hz, 2H), 2.93 (t, J = 7.5 Hz, 2H)

| IUPAC name | Structure | MS calculated | MS ESI [M + H]+ | Yield; Appearance; Salt form |
|---|---|---|---|---|
| 2-(4-Iodophenyl)-6-methyl-2,6-diaza-spiro[3.3]heptane | | $[C_{12}H_{15}IN_2 + H]^+$ 315.0 | 315.1 | 192 mg (16%); beige solid; free base |

Starting materials: 4-diiodobenzene (1.29 g, 3.9 mmol), 2-Methyl-2,6-diazaspiro[3.3]heptane oxalate (0.62 g, 3.9 mmol)
$^1$H NMR (400 MHz, CD$_3$OD) δ ppm 7.42 (d, J = 8.5 Hz, 2H), 6.26 (d, J = 8.5 Hz, 2H), 3.87 (s, 4H), 3.42 (s, 4H), 2.32 (s, 3H)

| IUPAC name | Structure | MS calculated | MS ESI [M + H]+ | Yield; Appearance; Salt form |
|---|---|---|---|---|
| tert-butyl 6-(4-iodophenyl)-2,6-diazaspiro[3.3]heptane-2-carboxylate | | $[C_{16}H_{21}IN_2O + H]^+$ 401.1 | 401.2 | 2.14 g (52%); white solid free base |

Starting materials: 4-diiodobenzene (3.40 g, 10.3 mmol), tert-butyl 2,6-diazaspiro[3.3]heptane-2-carboxylate oxalate (2.5 g, 10.3 mmol)
$^1$H NMR (400 MHz, CDCl$_3$) δ ppm 7.46 (d, J = 8.8 Hz, 2H), 6.22 (d, J = 8.8 Hz, 2H), 4.08 (s, 4H), 3.94 (s, 4H), 1.44 (s, 9H)

| IUPAC name | Structure | MS calculated | MS ESI [M + H]+ | Yield; Appearance; Salt form |
|---|---|---|---|---|
| 2-(4-iodophenyl)-2-azaspiro[3.3]heptan-6-ol | | $[C_{12}H_{14}INO + H]^+$ 316.0 | 315.9 | 1.01 g (34%); white solid free base |

Starting materials: 4-diiodobenzene (3.10 g, 9.4 mmol), 2-azaspiro[3.3]heptan-6-ol (2.13 g, 9.4 mmol)
$^1$H NMR (400 MHz, CDCl$_3$) δ ppm 7.44 (d, J = 8.0 Hz, 2H), 6.19 (d, J = 8.3 Hz, 2H), 4.21-4.31 (m, 1H), 3.81 (d, J = 4.5 Hz, 4H), 2.55-2.65 (m, 2H), 2.09-2.19 (m, 2H), 1.70 (br. d, J = 6.0 Hz, 1H)

| IUPAC name | Structure | MS calculated | MS ESI [M + H]+ | Yield; Appearance; Salt form |
|---|---|---|---|---|
| 1-(4-Iodophenyl)-6-oxa-1-azaspiro[3.3]heptane | 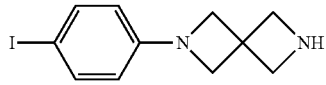 [SMILES: Ic1ccc(N2CC3(CNC3)C2)cc1] | [C$_{11}$H$_{12}$INO + H]+ 302.0 | 302.0 | 1.16 g (55%); light yellow solid; free base |

Starting materials: 1,4-diiodobenzene (2.3 g, 6.9 mmol), 6-Oxa-1-azaspiro[3.3]heptane oxalate
$^1$H NMR (400 MHz, CDCl$_3$) δ ppm 7.53 (d, J = 4.5 Hz, 2H), 6.56 (d, J = 4.5 Hz, 2H), 5.24 (d, J = 8.8 Hz, 2H), 4.76 (d, J = 8.3 Hz, 2H), 3.67 (t, J = 6.9 Hz, 2H), 2.54 (t, J = 6.9 Hz, 2H)

2-(4-Iodophenyl)-2,6-diazaspiro[3.3]heptane

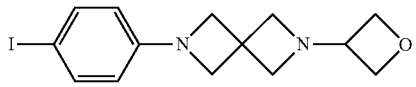 [SMILES: Ic1ccc(N2CC3(C2)CN(C2COC2)C3)cc1]

tert-Butyl 6-(4-iodophenyl)-2,6-diazaspiro[3.3]heptane-2-carboxylate (2.14 g, 5.35 mmol) was dissolved in DCM (10 mL) and cooled to 0° C. TFA (5 mL) was added and then reaction was stirred at 0° C. for 30 min, warmed up to rt and stirred for 1 h. The mixture was concentrated under reduced pressure and purified using a Waters PoraPak Rxn CX 20 cc 2 g cartridge to give the title compound as a white solid (1.51 g, 94%). $^1$H NMR (400 MHz, CDCl$_3$) δ ppm 7.45 (d, J=8.5 Hz, 2H), 6.22 (d, J=8.5 Hz, 2H), 3.94 (s, 4H), 3.80 (s, 4H), 1.66 (br. s., 1H); MS ESI 301.0 [M+H]+, calcd for [C$_{11}$H$_{13}$IN$_2$+H]+ 301.0.

2-(4-iodophenyl)-6-(oxetan-3-yl)-2,6-diazaspiro[3.3]heptane

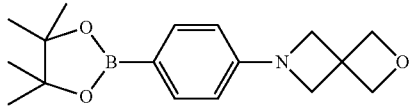 [SMILES: CC1(C)OB(c2ccc(N3CC4(COC4)C3)cc2)OC1(C)C]

2-(4-Iodophenyl)-2,6-diazaspiro[3.3]heptane (1.01 g, 3.4 mmol), and 3-oxetanone (0.29 g, 4.0 mmol) was dissolved in DCE (15 mL) and heated to 50° C. for 10 min. Acetic acid (5 drops) and NaBH(OAc)$_3$ (1.07 g, 5.1 mmol) was added and the reaction was stirred for 16 h at 50° C. The mixture was concentrated under reduced pressure and suspended in NaHCO$_3$ (50 mL) and extracted with EtOAc (2×40 mL) and washed with brine. The EtOAc layer was dried (MgSO$_4$), and concentrated to dryness to give the title compound as a white solid (1.15 g, 96%). MS ESI 357.0 [M+H]+, calcd for [C$_{14}$H$_{17}$IN$_2$O+H]+357.0.

6-(4-(4,4,5,5-tetramethyl-1,3,2-dioxaborolan-2-yl)phenyl)-2-oxa-6-azaspiro[3.3]heptane The title compound was synthesized according to method E, utilizing 6-(4-Iodophenyl)-2-oxa-6-azaspiro[3.3]heptane (720 mg, 2.4 mmol), bis(pinacolato)diboron (910 mg, 3.6 mmol), PdCl$_2$(dppf) (98 mg, 0.12 mmol), KOAc (710 mg, 7.2 mmol) and DMSO (12 mL). The reaction was quenched with sat. NaHCO$_3$ solution, extracted with EtOAc, dried (MgSO$_4$), filtered, and concentrated to dryness. Purification by flash chromatography (Biotage Isolera, 50 g HP-SIL, 10-40% EtOAc in hexanes) gave the title compound as a white solid (440 mg, 60%). $^1$H NMR (400 MHz, CDCl$_3$) δ ppm 7.68 (d, J=8.5 Hz, 2H), 6.43 (d, J=8.5 Hz, 2H), 4.85 (s, 4H), 4.07 (s, 4H), 1.33 (s, 12H); MS ESI 302.2 [M+H]+, calcd for [C$_{17}$H$_{24}$BNO$_3$+H]+ 302.1.

The following intermediates were synthesized according to the synthesis of 6-(4-(4,4,5,5-tetramethyl-1,3,2-dioxaborolan-2-yl)phenyl)-2-oxa-6-azaspiro[3.3]heptane using General Method E:

| IUPAC name | Structure | MS calculated | MS ESI [M + H]+ | Yield; Appearance; Salt form |
|---|---|---|---|---|
| 7-(4-(4,4,5,5-Tetramethyl-1,3,2-dioxaborolan-2-yl)phenyl)-2-oxa-7-azaspiro[3.5]nonane | 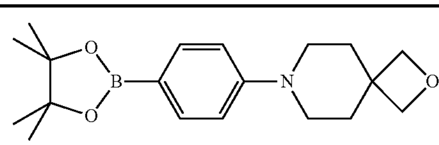 | [C$_{19}$H$_{28}$BNO$_3$ + H]+ 330.2 | 330.2 | 300 mg (51%); white solid; free base |

Starting materials: 7-(4-Iodophenyl)-2-oxa-7-aza-spiro[3.5]nonane (0.58 g, 1.8 mmol)
$^1$H NMR (400 MHz, CDCl$_3$) δ ppm 7.70 (d, J = 8.8 Hz, 2H), 6.90 (d, J = 8.8 Hz, 2H), 4.48 (s, 4 H), 3.17-3.23 (m, 4H), 1.96-2.01 (m, 4H), 1.33 (s, 12H)

| Structure | MS calculated | MS ESI [M + H]⁺ | Yield; Appearance; Salt form |
|---|---|---|---|
| 6-(4-(4,4,5,5-Tetramethyl-1,3,2-dioxaborolan-2-yl)phenyl)-2-oxa-6-azaspiro[3.4]octane | $[C_{18}H_{26}BNO_3 + H]^+$ 316.2 | 316.1 | 222 mg (43%); white solid; free base |

Starting materials: 6-(4-Iodophenyl)-2-oxa-6-aza-spiro[3.4]octane (0.51 g, 1.6 mmol)
¹H NMR (400 MHz, CDCl₃) δ ppm 7.70 (d, J = 8.8 Hz, 2H), 6.54 (d, J = 8.5 Hz, 2H), 4.72 (d, J = 6.0 Hz, 2H), 4.65 (d, J = 5.8 Hz, 2H), 3.59 (s, 2H), 3.38 (t, J = 6.8 Hz, 2H), 2.32 (t, J = 6.9 Hz, 2H), 1.33 (s, 12H)

| Structure | MS calculated | MS ESI [M + H]⁺ | Yield; Appearance; Salt form |
|---|---|---|---|
| 2-(4-(4,4,5,5-Tetramethyl-1,3,2-dioxaborolan-2-yl)phenyl)-7-oxa-2-azaspiro[3.5]nonane | $[C_{19}H_{28}BNO_3 + H]^+$ 330.2 | 330.2 | 303 mg (52%); yellow solid; free base |

Starting materials: 2-(4-Iodophenyl)-7-oxa-2-aza-spiro[3.5]nonane (0.75 g, 1.8 mmol)
¹H NMR (400 MHz, CDCl₃) δ ppm 7.68 (d, J = 8.3 Hz, 2H), 6.43 (d, J = 8.3 Hz, 2H), 3.61-3.74 (m, 8H), 1.84 (t, J = 5.0 Hz, 4H), 1.33 (s, 12H)

| Structure | MS calculated | MS ESI [M + H]⁺ | Yield; Appearance; Salt form |
|---|---|---|---|
| 6-(4-(4,4,5,5-Tetramethyl-1,3,2-dioxaborolan-2-yl)phenyl)-1-oxa-6-azaspiro[3.3]heptane | $[C_{17}H_{24}BNO_3 + H]^+$ 302.2 | 302.2 | 443 mg (62%); colourless oil; free base |

Starting materials: 6-(4-Iodophenyl)-1-oxa-6-aza-spiro[3.3]heptane (0.64 g, 2.1 mmol)
¹H NMR (400 MHz, CDCl₃) δ ppm 7.67 (d, J = 8.4 Hz, 2H), 6.43 (d, J = 8.3 Hz, 2H), 4.58 (t, J = 7.4 Hz, 2H), 4.13 (d, J = 9.0 Hz, 2H), 4.04 (d, J = 9.1 Hz, 2H), 2.93 (t, J = 7.4 Hz, 2H), 1.33 (s, 12H)

| Structure | MS calculated | MS ESI [M + H]⁺ | Yield; Appearance; Salt form |
|---|---|---|---|
| 2-methyl-6-(4-(4,4,5,5-tetramethyl-1,3,2-dioxaborolan-2-yl)phenyl)-2,6-diazaspiro[3.3]heptane | $[C_{18}H_{27}BN_2O_2 + H]^+$ 315.2 | 315.3 | 120 mg (75%); beige solid; free base |

Starting materials: 2-(4-iodophenyl)-6-methyl-2,6-diazaspro[3.3]heptanes (0.16, 0.51 mmol)
¹H NMR (400 MHz, CD₃OD) δ ppm 7.55 (d, J = 8.3 Hz, 2H), 6.42 (d, J = 8.0 Hz, 2H), 3.94 (s, 4H), 3.47 (s, 4H), 2.35 (s, 3H), 1.31 (s, 12H)

| Structure | MS calculated | MS ESI [M + H]⁺ | Yield; Appearance; Salt form |
|---|---|---|---|
| 2-(oxetan-3-yl)-6-(4-(4,4,5,5-tetramethyl-1,3,2-dioxaborolan-2-yl)phenyl)-2,6-diazaspiro[3.3]heptane | $[C_{20}H_{29}BN_2O_3 + H]^+$ 357.2 | 357.1 | 680 mg (59%); white solid; free base |

Starting materials: 2-(4-iodophenyl)-6-(oxetan-3-yl)-2,6-diazaspiro[3.3]heptanes (1.15 g, 3.2 mmol)
¹H NMR (400 MHz, CDCl₃) δ ppm 7.67 (d, J = 8.3 Hz, 2H), 6.42 (d, J = 8.0 Hz, 2H), 4.70 (t, J = 6.3 Hz, 2H), 4.50 (t, J = 6.0 Hz, 4H), 4.00 (s, 4H), 3.70-3.77 (m, 1H), 3.46 (s, 4H), 1.32 (s, 12H)

| Structure | MS calculated | MS ESI [M + H]⁺ | Yield; Appearance; Salt form |
|---|---|---|---|
| 2-(4-(4,4,5,5-tetramethyl-1,3,2-dioxaborolan-2yl)phenyl)-2-azaspiro[3.3]heptan-6-ol | $[C_{18}H_{26}BNO_3 + H]^+$ 316.2 | 316.1 | 840 mg (84%); colourless oil; free base |

Starting materials: 2-(4-iodophenyl)-2-azaspiro[3.3]heptan-6-ol (1 g, 3.2 mmol)
¹H NMR (400 MHz, CDCl₃) δ ppm 7.65 (d, J = 7.8 Hz, 2H), 6.39 (d, J = 8.0 Hz, 2H), 4.21-4.30 (m, 1H), 3.87 (d, J = 6.3 Hz, 4H), 2.56-2.64 (m, 2H), 2.10-2.18 (m, 2H), 1.72-1.81 (m, 1H), 1.32 (s, 12H)

| Structure | | MS calculated | MS ESI [M + H]+ | Yield; Appearance; Salt form |
|---|---|---|---|---|
| 1-(4-(4,4,5,5-Tetramethyl-1,3,2-dioxaborolan-2-yl)phenyl)-6-oxa-1-azaspiro[3.3]heptane | | $[C_{17}H_{24}BNO_3 + H]^+$ 302.2 | 302.2 | 913 mg (71%); white solid; free base |

Starting materials: 1-(4-Iodophenyl)-6-oxa-1-azaspiro[3.3]heptane (1.2 g, 3.8 mmol)
$^1$H NMR (400 MHz, CDCl$_3$) δ ppm 7.73 (d, J = 8.5 Hz, 2H), 6.76 (d, J = 8.8 Hz, 2H), 5.33 (d, J = 7.8 Hz, 2H), 4.76 (d, J = 7.8 Hz, 2H), 3.74 (t, J = 6.9 Hz, 2H), 2.56 (t, J = 6.9 Hz, 2H), 1.34 (s, 12H)

1-(2-chlorophenyl)-2-methylpropan-1-ol

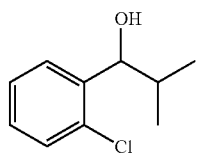

A solution of 2-chlorobenzaldehyde (2.75 g) in Et$_2$O (30 mL) was slowly added to a solution of i-PrMgBr (obtained from 0.98 g of Mg and 4.85 g 2-bromopropane in 70 mL anhydrous Et$_2$O and the mixture was stirred for 30 min at rt) at 0° C. The reaction mixture was stirred for 1 h at 0° C., and then quenched with aq. 25% NH$_4$Cl (100 mL). The organic layer was separated and the aq. layer was extracted with EtOAc (50 mL). The combined organic layer was washed with H$_2$O and brine, dried (Na$_2$SO$_4$) and concentrated under vacuum. Purification by flash chromatography (SiO$_2$, 0-25% EtOAc in hexanes) gave the title compound as a clear colorless oil (1.5 g, 41%). $^1$H NMR (400 MHz, DMSO-d$_6$) δ ppm 7.52 (d, J=7.2 Hz, 1H). 7.37-7.31 (m, 2H), 7.25-7.21 (m, 1H), 5.27 (d, J=4.4 Hz, 1H), 4.68 (dd, J=5.2 Hz, 1H). 1.88-1.80 (m, 1H), 0.86 (dd, J=17.2 Hz, J=6.8 Hz, 6H).

1-(2-chlorophenyl)-2-methyl-propan-1-one

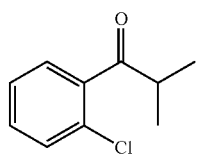

A solution of 1-(2-chlorophenyl)-2-methylpropan-1-ol (1.5 g in 15 mL DCM) was added is to a suspension of PCC (2.62 g in 30 mL DCM) at 25° C., monitoring the reaction by TLC. After 2 h, Et$_2$O (120 mL) was added and the reaction mixture was stirred for 15 min. The supernatant was decanted, dried (Na$_2$SO$_4$) and concentrated under vacuum. Purification by flash chromatography (SiO$_2$, 0-10% EtOAc in hexanes) gave the title compound as a clear colorless oil (1.24 g, 82%). $^1$H NMR (400 MHz, CDCl$_3$) δ ppm 7.41-7.27 (m, 4H), 3.37-3.30 (m, 1H), 1.19 (d, J=6.8 Hz, 6H).

Cyclopropyl(o-tolyl)methanamine

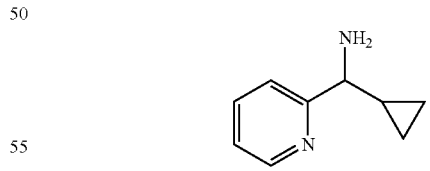

The title compound was synthesized according to method G, utilizing Mg powder (240 mg, 10 mmol), bromocyclopropane (1.21 g, 10 mmol), 2-methylbenzonitrile (468 mg, 4 mmol), and NaBH$_4$ (380 mg, 10 mmol). The reaction mixture was concentrated and purified by Biotage SiO$_2$ column (gradient: MeOH/DCM 0-20%) to give cyclopropyl(o-tolyl)methanamine as a yellow oil (0.70 g, 87%) which solidified upon standing. $^1$H NMR (400 MHz, CD$_3$OD) δ ppm 8.49 (d, J=7.6 Hz, 1H), 7.27-7.22 (m, 1H), 7.20-7.17 (m, 2H), 3.75 (d, J=8.4 Hz, 1H), 2.35 (s, 3H), 1.37-1.27 (m, 1H), 0.71-0.63 (m, 1H), 0.53-0.46 (m, 1H), 0.38-0.31 (m, 1H), 0.29-0.33 (m, 1H); MS ESI 145.0 [M+H]$^+$, calcd for [C$_{11}$H$_{15}$N—NH$_2$+H]$^+$ 145.1.

Cyclopropyl(pyridin-2-yl)methanamine

The title compound was synthesized according to method G, utilizing Mg powder (240 mg, 10 mmol), bromocyclopropane (1.21 g, 10 mmol), picolinonitrile (520 mg, 5 mmol) and NaBH$_4$ (380 mg, 10 mmol). The reaction mixture was quenched with H$_2$O, extracted with DCM and purified by Biotage SiO$_2$ column (gradient: MeOH/DCM 0-30%) to give cyclopropyl(pyridin-2-yl)methanamine as a light brown oil (590 mg). $^1$H NMR (400 MHz, CDCl$_3$) δ ppm 8.52 (d, J=4.0 Hz, 1H), 7.82 (dt, J=7.6 Hz, 1.6 Hz, 1H), 7.50 (d, J=8.0 Hz, 1H), 7.34-7.39 (m, 1H), 3.25 (d, J=8.8 Hz, 1H), 1.18-1.10 (m, 1H), 0.70-0.62 (m, 1H), 0.54-0.42 (m, 2H), 0.40-0.34 (m, 1H); MS ESI 132.0 [M+H]⁺, calcd for [C₉H₁₂N₂—NH₃+H]⁺ 132.1.

Cyclopropyhthiazol-2-yl)methanol

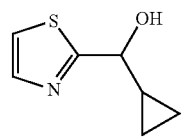

A solution of PrMgBr (0.5M in THF, 5.3 mL, 2.7 mmol) was added dropwise to a cooled solution of thiazole-2-carbaldehyde (0.2 mL, 2.2 mmol) in dry THF under nitrogen. After the addition was complete, the resulting mixture was stirred at rt for 1 hour. The reaction mixture was quenched by addition of H₂O, extracted with EtOAc, dried over MgSO₄, filtered, and concentrated to dryness. Purification by flash chromatography (Biotage Isolera, 25 g HP-SIL, 5-40% EtOAc in hexanes) gave the title compound as a colourless oil (327 mg, 95%). ¹H NMR (400 MHz, CDCl₃) δ ppm 7.62 (d, J=3.3 Hz, 1H), 7.23 (d, J=3.3 Hz, 1H), 4.35 (d, J=7.8 Hz, 1H), 1.13-1.31 (m, 1H), 0.36-0.64 (m, 4H); MS ESI 138.0 [M-OH]⁺, calcd for [C₇H₉NOS—OH]⁺ 138.0.

Cyclopropyl(thiazol-2-yl)methanone

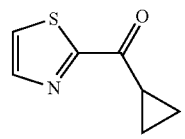

A mixture of cyclopropyl(thiazol-2-yl)methanol (327 mg, 2.1 mmol) and MnO₂ (1.0 g, 11 mmol) in DCM (10 mL) was stirred at rt for 2 days. The mixture was diluted with DCM, filtered through a cake of Celite and the filtrate was concentrated to give the title compound as a colourless oil (278 mg, 86%). The product used without further purification. ¹H NMR (400 MHz, CDCl₃) δ ppm 7.93 (d, J=3.0 Hz, 1H), 7.61 (d, J=3.0 Hz, 1H), 3.05-3.22 (m, 1H), 1.16-1.30 (m, 2H), 0.98-1.11 (m, 2H); MS ESI 154.0 [M+M]⁺, calcd for [C₇H₇NOS+H]⁺ 154.0.

Cyclopropyl(thiazol-2-yl)methanamine

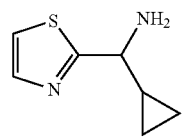

The title compound was synthesized according to General Method F, utilizing cyclopropyl(thiazol-2-yl)methanone (0.28 g, 1.8 mmol), NH₄OAc (1.7 g, 22 mmol), NaCNBH₃ (0.46 g, 7.3 mmol), and MeOH (30 mL). Aq. NaOH (2 M, 15 mL) was added and the product was extracted into EtOAc (3×40 mL). The combined EtOAc layer was dried (MgSO₄), filtered, concentrated to dryness. Purification by flash chromatography (Biotage Isolera, 25 g HP-SIL, 60-100% EtOAc in hexanes) gave the title compound as a yellow oil (0.15 g, 55% yield). ¹H NMR (400 MHz, CDCl₃) δ ppm 7.63 (d, J=2.8 Hz, 1H), 7.18 (d, J=2.8 Hz, 1H), 3.50 (d, J=8.5 Hz, 1H), 2.35 (br. s., 2H), 1.03-1.16 (m, 1H), 0.48-0.63 (m, 2H), 0.26-0.47 (m, 2H); MS ESI 138.0 [M-NH₂]⁺, calcd for [C₇H₁₀N₂S—NH₂]⁺ 138.0.

The following intermediates were synthesized according to the synthesis of cyclopropyl(thiazol-2-yl)methanamine using General Method F:

| | Structure | MS calculated | MS ESI [M + H]⁺ | Yield; Appearance; Salt form |
|---|---|---|---|---|
| Cyclopentyl(pyridin-2-yl)methanamine | 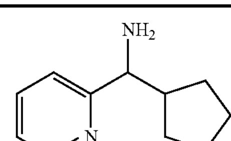 | [C₁₁H₁₆N₂ + H]⁺ 177.1 | 177.1 | 931 mg (93%); clear oil; free base |

Starting material: cyclopentyl-2-pyridyl ketone (1 g, 5.7 mmol)
¹H NMR (400 MHz, CD₃OD) δ ppm 8.50 (d, J = 4.0 Hz, 1H), 7.80 (t, J = 7.9 Hz, 1H), 7.41 (d, J = 8.0 Hz, 1H), 7.31 (t, J = 5.0 Hz, 1H), 3.76 (d, J = 8.8 Hz, 1H), 2.14-2.27 (m, 1H), 1.88-1.99 (m, 1H), 1.36-1.75 (m, 5H), 1.25-1.35 (m, 1H), 1.12-1.24 (m, 1H)

| | Structure | MS calculated | MS ESI [M + H]⁺ | Yield; Appearance; Salt form |
|---|---|---|---|---|
| 1-(2-Chlorophenyl)-2-methylpropan-1-amine | | [C₁₀H₁₄ClN + H]⁺ 184.1 | 184.1 | 348 mg (23%): colourless oil; free base |

Starting material: 1-(2-chlorophenyl)-2-methyl-propan-1-one (1.5 g, 8.2 mmol)
¹H NMR (400 MHz, DMSO-d₆) δ ppm 7.38-7.21 (m, 4H), 4.87 (br.s, 2H), 4.16 (d, J = 8.0 Hz, 1H), 2.12-2.04 (m, 1H), 1.02 (d, J J = 6.4 Hz, 3H), 0.82 (d, J = 6.8 Hz, 3H)

| Structure | MS calculated | MS ESI [M + H]+ | Yield; Appearance; Salt form |
|---|---|---|---|
| Cyclopentyl(thiophen-3-yl)methanamine ![structure] | [C₁₀H₁₅NS + H]⁺ 182.1 | 182.1 | 3.3 g (93%); Colourless oil; free base |

Starting material: cyclopentyl-3-thienyl ketone (3.5 g, 19 mmol)
¹H NMR (400 MHz, DMSO-d₆) δ ppm 7.44-7.42 (m, 1H), 7.27 (t, J = 2 Hz, 1H), 7.412-7.10 (m, 1H), 3.74 (t, J = 8.4 Hz, 1H), 2.09-1.99 (m, 1H), 1.76-1.68 (m, 1H), 1.58-1.29 (m, 6H), 1.16-1.14 (m, 1H)

2-(Pyrrolidin-1-yl)-2-(thiophen-3-yl)acetic acid

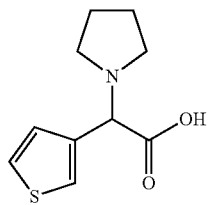 [SMILES: O=C(O)C(c1ccsc1)N1CCCC1]

A mixture of glyoxylic acid monohydrate (10.79 g, 0.11 mol) and pyrrolidine (9.69 mL, 0.11 mol) in DCM (375 mL) was sonicated for 15 minutes. Thiophene-3-boronic acid (15 g, 0.11 mol) was added and the mixture was stirred at rt for 24 h. The solid was filtered and washed with little DCM to gave 38 g crude product as crop-1. The mother liquor concentrated under reduced pressure to give an additional 4 g as crop-2. The combined crude product purified by Biotgae SNAP 100 g silica column (gradient 0-50% MeOH in DCM) gave the title compound as a cream solid (21.7 g, 70%). ¹H NMR (400 MHz, CD₃OD) δ ppm 7.66 (dd, J=2.8 Hz, J=1.2 Hz, 1H), 7.53 (dd, J=5.2 Hz, J=2.8 Hz, 1H), 7.28 (dd, J=5.2 Hz, J=1.2 Hz, 1H), 4.65 (s, 1H), 3.06 (br. s, 2H), 2.04-1.95 (br. s, 4H), 2H merged with solvent peak; MS ESI 212 [M+H]⁺, calcd for [C₁₀H₁₃NO₂S+H]⁺ 212.07.

N-(Cyclopropyl(thiazol-2-yl)methyl)-3-iodo-1H-indazole-5-carboxamide

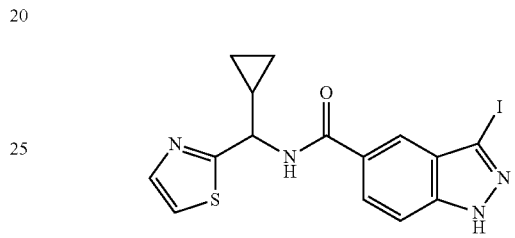

The title compound was synthesized according to General Method A utilizing 3-iodo-1H-indazole-5-carboxylic acid (255 mg, 0.88 mmol), cyclopropyl(thiazol-2-yl)methanamine (150 mg, 0.97 mmol), TBTU (310 mg, 0.97 mmol), DIPEA (0.31 mL, 1.8 mmol), and DMF (8 mL). The reaction was stirred at 0° C. for 1 h. The crude reaction was subsequently diluted with H₂O. A filtration and washing (H₂O) of the precipitate provided the desired product as a beige solid (195 mg, 52%). The product used without further purification. ¹H NMR (400 MHz, CD₃OD) δ ppm 8.16 (br. s., 1H), 7.99 (m., 1H), 7.77 (br. s., 1H), 7.46-7.67 (m, 2H), 1.45-1.68 (m, 1H), 0.46-0.90 (m, 4H); MS ESI 425.0 [M+H]⁺, calcd for [C₁₅H₁₃IN₄OS+H]⁺ 425.0.

The following intermediates were synthesized according to the synthesis of N-(cyclopropyl(thiazol-2-yl)methyl)-3-iodo-1H-indazole-5-carboxamide using General Method A:

| | Structure | MS calculated | MS ESI [M + H]+ | Yield; Appearance; Salt form |
|---|---|---|---|---|
| N-(3-iodo-1H-indazol-5-yl)-2-(pyrrolidin-1-yl)-2-(thiophen-3-yl)acetamide | 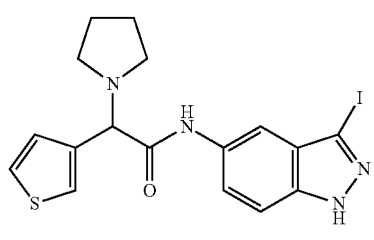 [SMILES: O=C(Nc1ccc2[nH]nc(I)c2c1)C(c1ccsc1)N1CCCC1] | [C17H17IN4OS + H]+ 453.0 | 453.0 | 1.61 g (44%); yellow solid; free base |

Starting materials: 3-iodo-1H-indazol-5-amine (2.5 g, 9.8 mmol) and 2-(pyrrolidin-1-yl)-2-(thiophen-3-yl)acetic acid (1.7 g, 8.0 mmol)
¹H NMR (400 MHz, CD₃OD) δ ppm 7.83 (s, 1H), 7.49-7.56 (m, 2H), 7.44-7.48 (m, 1H), 7.39-7.44 (m, 1H), 7.33 (d, J = 5.0 Hz, 1H), 4.11 (s, 1H), 2.67 (d, J = 6.0 Hz, 2H), 2.51 (d, J = 5.8 Hz, 2H), 1.81-1.87 (m, 5H)

| Structure | MS calculated | MS ESI [M + H]+ | Yield; Appearance; Salt form |
|---|---|---|---|
| N-(Cyclo-propyl(pyridin-2-yl)methyl)-3-iodo-1H-indazole-5-carboxamide | [C₁₇H₁₅IN₄O + H]⁺ 419.0 | 419.0 | 1.29 g (78%); off white solid; free base |

Starting materials: 3-iodo-1H-indazole-5-carboxylic acid (1.1 g, 3.94 mmol), cyclopropyl(pyridin-2-yl)methanamine (575 mg, 3.9 mmol
¹H NMR (400 MHz, CD₃OD) δ ppm 8.51-8.55 (m, 1H), 8.13-8.16 (m, 1H), 7.95-8.00 (m, 1H), 7.81-7.86 (m, 1H), 7.53-7.61 (m, 2H), 7.30-7.36 (m, 1H), 4.49-4.53 (m, 1H), 1.38-1.48 (m, 1H), 0.68-0.75 (m, 1H), 0.51-0.64 (m, 3H)

| Structure | MS calculated | MS ESI [M + H]+ | Yield; Appearance; Salt form |
|---|---|---|---|
| (S)-N-(yclopropyl(pyridin-2-yl)methyl)-3-iodo-1H-indazole-5-carboxamide | [C₁₇H₁₅IN₄O + H]⁺ 419.0 | 419.0 | 874 mg (77%); yellow solid; free base |

Starting materials: 3-iodo-1H-indazole-5-carboxylic acid (782 mg, 2.7 mmol), (S)-cyclopropyl(pyridin-2-yl)methanamine (402 mg, 2.7 mmol)
¹H NMR: Spectral data was identical for that obtained in N-(Cyclopropyl(pyridin-2-yl)methyl)-3-iodo-1H-indazole-5-carboxamide

| Structure | MS calculated | MS ESI [M + H]+ | Yield; Appearance; Salt form |
|---|---|---|---|
| (R)-N-(cyclopropyl(pyridin-2-yl)methyl)-3-iodo-1H-indazole-5-carboxamide | [C₁₇H₁₅IN₄O + H]⁺ 419.0 | 419.0 | 334 mg (80%); light yellow solid; free base |

Starting materials: 3-iodo-1H-indazole-5-carboxylic acid (288 mg, 1.0 mmol), (R)-cyclopropyl(pyridin-2-yl)methanamine (148 mg, 1.0 mmol)
¹H NMR: Spectral data was identical for that obtained in N-(Cyclopropyl(pyridin-2-yl)methyl)-3-iodo-1H-indazole-5-carboxamide

| Structure | MS calculated | MS ESI [M + H]+ | Yield; Appearance; Salt form |
|---|---|---|---|
| N-(cyclopentyl(pyridin-2-yl)methyl)-3-iodo-1H-indazole-5-carboxamide | [C₁₉H₁₉IN₄O + H]⁺ 447.1 | 447.1 | 1.8 g (75%); Pale yellow solid; free base |

Starting materials: 3-iodo-1H-indazole-5-carboxylic acid (1.5 g, 5.3 mmol), cyclopentyl(pyridin-2-yl)methanamine (930 mg, 5.3 mmol)
¹H NMR (400 MHz, CD₃OD) δ ppm 8.50-8.57 (m, 1H), 8.07 (s, 1H), 7.93 (d, J = 9.3 Hz, 1H), 7.82 (t, J = 7.4 Hz, 1H), 7.57 (d, J = 8.8 Hz, 1H), 7.51 (d, J = 7.5 Hz, 1H), 7.32 dd, J = 6.6, 5.4 Hz, 1H), 5.01 (d, J = 9.8 Hz, 1H), 2.48-2.62 (m, 1H), 1.94-2.05 (m, 1H), 1.48-1.78 (m, 5H), 1.23-1.42 (m, 2H)

| Structure | MS calculated | MS ESI [M + H]+ | Yield; Appearance; Salt form |
|---|---|---|---|
| N-(1-(2-chlorophenyl)-2-methylpropyl)-3-iodo-1H-indazole-5-carboxamide | [C₁₈H₁₇ClIN₃O + H]⁺ 454.0 | 454.0 | 1.3 g (95%); cream color solid; free base |

Starting materials: 3-iodo-1H-indazole-5-carboxylic acid (863 mg, 3.0 mmol), 1-(2-chlorophenyl)-2-methylpropan-1-amine (0.55 g, 3.0 mmol)
¹H NMR (400 MHz, DMSO-d₆) δ 13.76 (s, 1H), 8.91 (d, J = 8.8 Hz, 1H), 7.91 (d, J = 9.2 Hz, 1H), 7.74-7.66 (m, 1H), 7.59 (d, J = 8.8 Hz, 1H), 7.46-7.22 (m, 4H), 5.27 (t, J = 9.2 Hz, 1H), 2.20-2.15 (m, 1H), 1.08 (d, J = 6.0 Hz, 3H), 0.79 (d, J = 6.8 Hz, 3H)

| Structure | MS calculated | MS ESI [M + H]⁺ | Yield; Appearance; Salt form |
|---|---|---|---|
| (S)-N-(cyclopropyl(phenyl)methyl)-3-iodo-1H-indazole-5-carboxamide 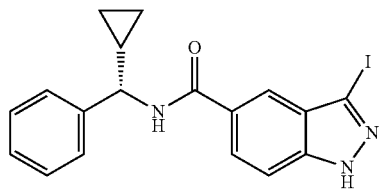 [SMILES: O=C(N[C@H](c1ccccc1)C1CC1)c1ccc2[nH]nc(I)c2c1] | $[C_{18}H_{16}IN_3O + H]^+$ 418.0 | 418.1 | 110 mg (98%); orange solid; free base |

Starting materials: 3-iodo-1H-indazole-5-carboxylic acid (79 mg, 0.79 mmol), (s)-cyploroylphenyl-methylamine•HCl (50 mg, 0.27 mmol)

¹H NMR 400 MHz, CD₃OD) δ ppm 8.09 (s, 1H), 7.95 (dd, J = 8.9, 1.6 Hz, 1H), 7.56 (d, J = 8.8 Hz, 1H), 7.43-7.50 (m, 2H), 7.33 (t, J = 7.6 Hz, 2H), 7.24 (t, J = 7.3 Hz, 1H), 4.46 (d, J = 9.5 Hz, 1H), 1.34-1.46 (m, 1H), 0.66 (d, J = 8.0 Hz, 2H), 0.48 (m, 2H)

| | | | |
|---|---|---|---|
| N-(cyclopropyl(o-tolyl)methyl)-3-iodo-1H-indazole-5-carboxamide 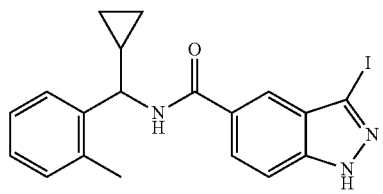 [SMILES: Cc1ccccc1C(NC(=O)c1ccc2[nH]nc(I)c2c1)C1CC1] | $[C_{19}H_{18}IN_3O + H]^+$ 432.0 | 432.1 | 7.5 g (99%); beige solid; free base |

Starting materials: 3-iodo-1H-indazole-5-carboxylic acid (5.0 g, 18 mmol), cyclopropyl(o-tolyl)methanamine (2.8 g, 18 mmol), ¹H NMR: Not available

| | | | |
|---|---|---|---|
| N-(cyclopentyl(thiophen-3-yl)methyl)-3-iodo-1H-indazole-5-carboxamide 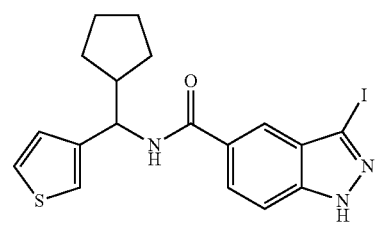 [SMILES: O=C(NC(c1ccsc1)C1CCCC1)c1ccc2[nH]nc(I)c2c1] | $[C_{18}H_{18}IN_3OS + H]^+$ 452.0 | 452.0 | 8.0 g (98%); beige solid; free base |

Starting materials: 3-iodo-1H-indazol-5-carboxylic acid (5.2 g, 18 mmol), cyclopentyl(thiophen-3-yl)methanamine (3.3 g, 18 mmol)

¹H NMR (400 MHz, DMSO-d₆) δ ppm 13.72 (br.s, 1H), 8.86 (t, J = 8.8 H_z, 1H), 7.92-7.9 (m, 1H), 7.58 (t, J = 8.8 H_z, 1H), 7.46-7.44 (m, 1H), 7.39-7.38 (m, 1H), 7.22 (d, J = 4.8 H_z, 1H), 4.98 (t, J = 9.6 H_z, 1H), 1.81-1.78 (m, 1H), 1.61-1.32 (m, 7H), 1.2-1.17 (m, 1H)

| | | | |
|---|---|---|---|
| N-(cyclopentyl(pyrimidin-2-yl)methyl)-3-iodo-1H-indazole-5-carboxamide 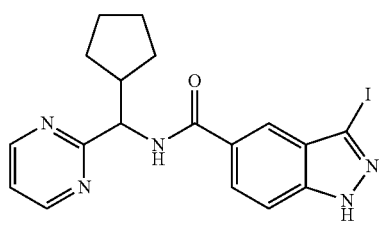 | $[C_{18}H_{18}IN_5O + H]^+$ 448.1 | 448.1 | 1.06 g (84%); pale yellow solid; free base |

Starting materials: 3-iodo-1H-indazole-5-carboxylic acid (0.83 g, 2.9 mmol), cyclopentyl(pyrimidin-2-yl)methanamine (0.51 g, 2.9 mmol), ¹H NMR (400 MHz, DMSO-d₆) δ ppm 13.67 (br. S., 1H), 8.95 (d, J = 8.28 Hz, 1H), 8.78 (d, J = 5.02 Hz, 2H), 8.11 (d, J = 0.75 Hz, 1H), 7.94 (dd, J = 8.78, 1.76 Hz, 1H), 7.57 (dd, J = 8.80, 0.75 Hz, 1H), 7.38 (t, J = 4.77 Hz, 1H), 5.02 (dd, J = 9.79, 8.28 Hz, 1H), 2.50-2.62 (m, 1H), 1.82-1.93 (m, 1H), 1.39-1.69 (m, 6H), 1.25-1.34 (m, 2H)

| Structure | MS calculated | MS ESI [M + H]+ | Yield; Appearance; Salt form |
|---|---|---|---|
| (S)-3-iodo-N-(3-methyl-1-(pyridin-2-yl)butyl)-1H-indazole-5-carboxamide | [C18H19IN4O + H]+ 435.1 | 435.1 | 1.21 g (65%); pale yellow solid; free base |

Starting materials: 3-iodo-1H-indazole-5-carboxylic acid (1.2 g, 4.3 mmol), (S)-3-Methyl-1-(pyridin-2-yl)butan-1-amine (705 mg, 4.3 mmol)
$^1$H NMR (400 MHz, DMSO-$d_6$) δ ppm 13.69 (br. s., 1H), 8.94 (d, J = 8.3 Hz, 1H), 8.48-8.55 (m, 1H), 8.13 (s, 1H), 7.90-8.01 (m, 1H), 7.75 (td, J = 7.7, 1.9 Hz, 1H), 7.59 (dd, J = 8.8, 0.8 Hz, 1H), 7.43 (d, J = 8.0 Hz, 1H), 7.24 (ddd, J = 7.5, 4.8, 1.0 Hz, 1H), 5.23 (d, J = 3.3 Hz, 1H), 1.81-1.92 (m, 1H), 1.63-1.76 (m, 2H), 0.94 (dd, J = 7.4, 6.4 Hz, 6H)

(S)-3-Methyl-1-(pyridin-2-yl)butan-1-amine

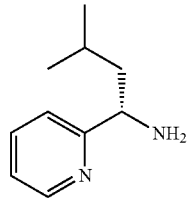

To a hot solution of (L)-DBTA (7.2 g, 20 mmol) in MeOH (75 mL) with stirring was added a solution of racemic 3-methyl-1-(pyridin-2-yl)butan-1-amine (3.3 g, 20 mmol) in MeOH (30 mL) dropwise. After addition, the resulting suspension was stirred for 5 min under reflux and cooled in air for about 5 min. The resulting precipitate was collected by vacuum filtration, washed with cold MeOH, air-dried and recrystallized from MeOH (200 mL) to give (L)-DBTA salt of (S)-3-methyl-1-(pyridin-2-yl)butan-1-amine as white solid (1.95 g, 95.6% ee). The ee of the compound was determined by acetylating small samples with acetyl chloride and analyzing the products by chiral HPLC: Daicel Chiralpak AD-H, 90:10 v/v hexanes-IPA (+0.5% Et$_3$N), 1.0 ml min$^{-1}$, λ=254 nm, R$_t$=5.8 mins (R), R$_t$=7.5 min (S).

To a suspension of the above salt (1.9 g) in MeOH (5 mL) was added 4 M NaOH (3 mL). A clear solution was formed. After diluting with H$_2$O (50 mL), the aq layer was extracted with DCM (30 mL×2), and the combined organic layers were dried (Na$_2$SO$_4$) and solvent was removed to give the desired amine as a colorless oil (705 mg, 21%).

The following enantiomerically pure intermediates were prepared by separating racemic compounds using preparative, chiral supercritical fluid chromatography (SFC):

| Structure | MS calculated | MS ESI [M + H]+ | Yield; Appearance; Salt form |
|---|---|---|---|
| (S)-N-(cyclopentyl(pyridin-2-yl)methyl)-3-iodo-1H-indazole-5-carboxamide | [C19H19IN4O + H]+ 447.1 | 447.1 | 3.6 g (46%); yellow solid; free base |

Starting materials: N-(cyclopentyl(pyridin-2-yl)methyl)-3-iodo-1H-indazole-5-carboxamide (7.9 g, 18 mmol)
Preparative HPLC method: AD-H (2 × 15 cm); 25% ethanol (0.1% DEA)/CO$_2$, 100 bar; 65 mL/min, 220 nm
Analytic HPLC method: AD-H (15 × 0.46 cm); 40% ethanol (DEA)/CO$_2$, 100 bar; 3 mL/min, 220, 254, and 280 nm; R$_t$ 2.14 min, >99% ee

| (R)-N-(cyclopentyl(pyridin-2-yl)methyl)-3-iodo-1H-indazole-5-carboxamide | [C19H19IN4O + H]+ 447.1 | 447.1 | 3.5 g (44%); yellow solid; free base |

|  |  |  | MS ESI | Yield; Appearance; |
|---|---|---|---|---|
|  | Structure | MS calculated | [M + H]⁺ | Salt form |

Starting materials: N-(cyclopentyl(pyridin-2-yl)methyl)-3-iodo-1H-indazole-5-carboxamide (7.9 g, 18 mmol)
Preparative HPLC method: AD-H (2 × 15 cm); 25% ethanol (0.1% DEA)/CO₂, 100 bar; 65 mL/min, 220 nm
Analytic HPLC method: AD-H (15 × 0.46 cm); 40% ethanol (DEA)/CO₂, 100 bar; 3 mL/min, 220, 254, and 280 nm; R$_t$ 1.36 min, >99% ee (S)-N-(1-(2-chlorophenyl)-2-methylpropyl)-3-iodo-1H-indazole-5-carboxamide

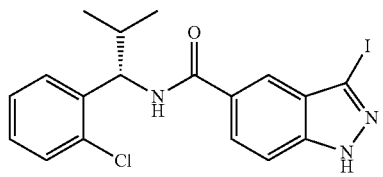 [SMILES: CC(C)[C@H](NC(=O)c1ccc2[nH]nc(I)c2c1)c1ccccc1Cl]

[C₁₈H₁₇ClIN₃O + H]⁺ 454.0
454.0

454 mg (46%); yellow solid; free base

Starting materials: N-(1-(2-chlorophenyl)-2-methylpropyl)-3-iodo-1H-indazole-5-carboxamide (1.0 g, 2.2 mmol)
Preparative HPLC method: IC (2 × 15 cm); 30% isopropanol/CO₂, 100 bar; 65 mL/min, 220 nm
Analytic HPLC method: IC (15 × 0.46 cm); 30% isopropanol (DEA)/CO₂, 100 bar; 3 mL/min, 220, 254, and 280 nm; R$_t$ 4.57 min, >99% ee (R)-N-(1-(2-chlorophenyl)-2-methylpropyl)-3-iodo-1H-indazole-5-carboxamide

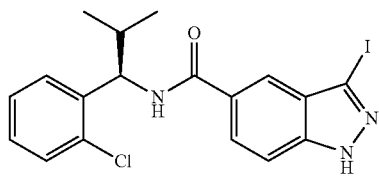 [SMILES: CC(C)[C@@H](NC(=O)c1ccc2[nH]nc(I)c2c1)c1ccccc1Cl]

[C₁₈H₁₇ClIN₃O + H]⁺ 454.0
454.0

454 mg (46%); yellow solid; free base

Starting materials: N-(1-(2-chlorophenyl)-2-methylpropyl)-3-iodo-1H-indazole-5-carboxamide (1.0 g, 2.2 mmol)
Preparative HPLC method: IC (2 × 15 cm); 30% isopropanol/CO₂, 100 bar; 65 mL/min, 220 nm
Analytic HPLC method: IC (15 × 0.46 cm); 30% isopropanol (DEA)/CO₂, 100 bar; 3 mL/min, 220, 254, and 280 nm; R$_t$ 6.32 min, >99% ee (S)-N-(cyclopentyl(thiophen-3-yl)methyl)-3-iodo-1H-indazole-5-carboxamide

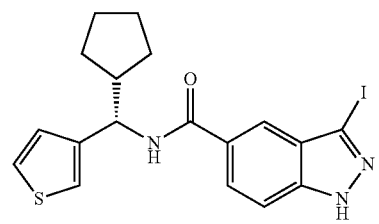

[C₁₈H₁₈IN₃OS + H]⁺ 452.0
452.0

1.1 g (42%); yellow solid; free base

Starting materials: N-(cyclopentyl(thiophen-3-yl)methyl)-3-iodo-1H-indazole-5-carboxamide (2.6 g, 5.8 mmol)
Preparative HPLC method: OJ-H (3 × 15 cm); 35 methanol (0.1% DEA)/CO₂, 100 bar; 70 mL/min, 220 nm
Analytic HPLC method: OJ-H (10 × 0.46 cm); 30% methanol (DEA)/CO₂, 100 bar; 3 mL/min, 220, 254, and 280 nm; R$_t$ 2.83 min, >99% ee (R)-N-(cyclopentyl(thiophen-3-yl)methyl)-3-iodo-1H-indazole-5-carboxamide

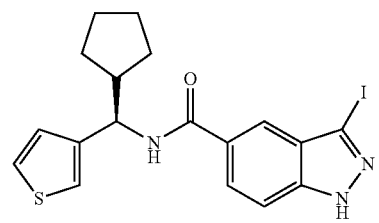 [SMILES: O=C(N[C@@H](c1ccsc1)C1CCCC1)c1ccc2[nH]nc(I)c2c1]

[C₁₈H₁₈IN₃OS + H]⁺ 452.0
452.0

1.2 g (46%); yellow solid; free base

Starting materials: N-(cyclopentyl(thiophen-3-yl)methyl)-3-iodo-1H-indazole-5-carboxamide (2.6 g, 5.8 mmol)
Preparative HPLC method: OJ-H (3 × 15 cm); 35 methanol (0.1% DEA)/CO₂, 100 bar; 70 mL/min, 220 nm
Analytic HPLC method: OJ-H (10 × 0.46 cm); 30% methanol (DEA)/CO₂, 100 bar; 3 mL/min, 220, 254, and 280 nm; R$_t$ 1.45 min, >99% ee

| Structure | MS calculated | MS ESI [M + H]⁺ | Yield; Appearance; Salt form |
|---|---|---|---|
| (S)-N-(cyclo-pentyl(pyrimidin-2-yl)methyl)-3-iodo-1H-indazole-5-carboxamide | $[C_{18}H_{18}IN_5O + H]^+$ 448.1 | 448.1 | 468 mg (44%); yellow solid; free base |

Starting materials: N-(cyclopentyl(pyrimidin-2-yl)methyl)-3-iodo-1H-indazole-5-carboxamide (1.1 g, 2.4 mmol)
Preparative HPLC method: AD-H (2 × 25 cm); 30% ethanol (0.1% DEA)/CO2, 100 bar; 65 mL/min, 220 nm
Analytic HPLC method: AD-H (25 × 0.46 cm) 40% ethanol (DEA)/CO2, 100 bar; 3 mL/min, 220 and 254 nm;
Rt 2.95 min, >99% ee

| Structure | MS calculated | MS ESI [M + H]⁺ | Yield; Appearance; Salt form |
|---|---|---|---|
| (R)-N-(cyclo-pentyl(pyrimidin-2-yl)methyl)-3-iodo-1H-indazole-5-carboxamide | $[[C_{18}H_{18}IN_5O + H]^+$ 448.1 | 448.4 | 475 mg (45%); yellow solid; free base |

Starting materials: N-(cyclopentyl(pyrimidin-2-yl)methyl)-3-iodo-1H-indazole-5-carboxamide (1.1 g, 2.4 mmol)
Preparative HPLC method: AD-H (2 × 25 cm); 30% ethanol (0.1%DEA)/CO2, 100 bar; 65 mL/min, 220 nm
Analytic HPLC method: AD-H (25 × 0.46 cm); 40% ethanol (DEA)/CO2, 100 bar; 3 mL/min, 220 and 254 nm; $R_t$ 2.29 min, >99% ee

(R,E)-N-(Cyclopentylmethylene)-2-methylpropane-2-sulfinamide

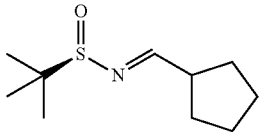

The title compound was synthesized according to General Method H utilizing cyclopentanecarboxaldehyde (15.0 g, 152.8 mmol, 1.0 eq.), (R)-t-butylsulfinylamide (24.1 g, 198.7 mmol, 1.3 eq.), and flame-dried CuSO₄ (73.2 g, 458.5 mmol, 3.0 eq.). The resulting mixture was stirred at rt for 71 h. The reaction mixture was filtered through a pad of Celite and the pad was rinsed with $CH_2Cl_2$ (5×100 mL). The combined organic extracts were concentrated under reduced pressure yielding a clear yellow oil (37.2 g). Purification by flash chromatography ($SiO_2$, h=6 cm, Ø=10 cm) using 1:9 EtOAc-cyclohexane as eluent gave the product (23.8 g, 78% isolated yield) as a clear pale yellow oil. ¹H NMR (300 MHz, CDCl₃) δ ppm 7.99 (d, J=5.5 Hz, 1H), 3.02-2.87 (m, 1H), 1.97-1.78 (m, 2H), 1.78-1.55 (m, 6H), 1.18 (s, 9H).

The following sulfinamides were synthesized according to the synthesis of (R,E)-N-(Cyclopentylmethylene)-2-methylpropane-2-sulfinamide using General Method H:

| Structure | MS calculated | MS ESI [M + H]⁺ | Yield; Appearance; Salt form |
|---|---|---|---|
| (S,E)-N-(2-Chlorobenzylidene)-2-methylpropane-2-sulfinamide | $[C_{11}H_{14}ClNOS + H]^+$ 244.1 | N/A | 26.9 g (89%); pale yellow oil; Free base |

Starting materials: 2-Chlorobenzaldehyde (20.9 g, 149 mmol), (S)-t-butylsulfinylamide (15.0 g, 124 mmol)
¹H NMR (300 MHz, CDCl₃) δ 9.05 (s, 1H), 8.06 (d, J = 7.5 Hz, 1H), 7.48-7.39 (m, 2H), 7.38-7.31 (m, 1H), 1.28 (s, 9H)

-continued

| Structure | | MS calculated | MS ESI [M + H]+ | Yield; Appearance; Salt form |
|---|---|---|---|---|
| (S,E)-2-Methyl-N-(thiophen-3-ylmethylene)propane-2-sulfinamide | 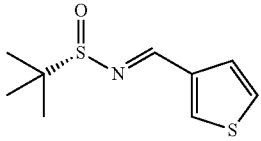 | [C$_9$H$_{13}$NOS$_2$ + H]+ 216.0 | N/A | 20.2 g (76%); white solid; free base |

Starting materials: 3-Thienylcarboxaldehyde (16.7 g, 149 mmol), (S)-t-butylsulfinylamide (15.0 g, 124 mmol)
$^1$H NMR (300 MHz, CDCl$_3$) δ 8.75 (s, 1H), 7.88-7.84 (m, 1H), 7.57 (d, J = 5.0 Hz, 1H), 7.40-7.34 (m, 1H), 1.25 (s, 9H)

Large scale asymmetric synthesis of (S)-1-(Cyclopentyl)-1-(2-pyridinyl)methylamine HCl salt A. (R$_S$)—N—((S)-Cyclopentyl(pyridin-2-yl)methyl)-2-methylpropane-2-sulfinamide

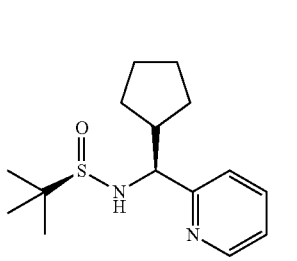 [SMILES: CC(C)(C)[S@@](=O)N[C@H](c1ccccn1)C1CCCC1]

A solution of 2-bromopyridine (11.8 mL, 19.5 g, 123.5 mmol in dry THF (50 mL) was added carefully to i-PrMgCl·LiCl (1.3 M in THF, 95.0 mL, 123.5 mmol). The resulting solution was stirred at rt for 3 h after which it was added dropwise, over 45 min, to a −48° C. solution of (R,E)-N-(cyclopentylmethylene)-2-methylpropane-2-sulfinamide (19.1 g, 95.0 mmol) in dry CH$_2$Cl$_2$ (250 mL). The resulting mixture was stirred at −48° C. for 1 h before being allowed to slowly warm up to rt over 16 h. The reaction was quenched by addition of saturated aq NH$_4$Cl (200 mL). H$_2$O (200 mL) was added and the mixture was extracted with CH$_2$Cl$_2$ (3×100 mL). The combined organic extracts were washed with brine (150 mL). The organic layer was dried (Na$_2$SO$_4$) and was concentrated under reduced pressure yielding the crude product (28.6 g, 5:1 d.r. (R$_S$,S)—(R$_S$,R)) as a clear red oil. The crude product was purified by repeated flash chromatography on silica gel using 1:19 MeOH-EtOAc as eluent in combination with trituration of the obtained solids with cyclohexane which eventually gave the pure product (8.80 g, 33%) as a white solid; $^1$H NMR (400 MHz, CDCl$_3$) δ ppm 8.56 (d, J=4.5 Hz, 1H), 7.63 (dt, J=1.0, 7.5 Hz, 1H), 7.22 (d, J=7.5 Hz, 1H), 7.16 (dd, J=4.5, 7.5 Hz, 1H), 4.26 (dd, J=5.0, 8.5 Hz, 1H), 3.95 (d, J=5.0 Hz, 1H), 2.44-2.31 (m, 1H), 1.94-1.83 (m, 1H), 1.68-1.44 (m, 5H), 1.44-1.32 (m, 1H), 1.30-1.17 (m, 1H), 1.13 (s, 9H).

B. (S)-1-(Cyclopentyl)-1-(2-pyridinyl)methylamine HCl salt

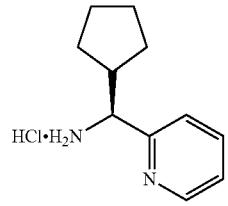

The title compound was synthesized according to General Method I utilizing HCl (2.0 M in Et$_2$O, 31.4 mL, 62.8 mmol) and a solution of (R$_S$)—N-((S)-cyclopentyl(pyridin-2-yl)methyl)-2-methylpropane-2-sulfinamide (8.8 g, 31.4 mmol) in MeOH (100 mL). After the addition was complete the cooling bath was removed and the mixture was stirred at rt for 1 h. The reaction mixture was concentrated under reduced pressure and the residue was suspended in Et$_2$O (125 mL). The precipitation was filtered off and washed with Et$_2$O (2×125 mL) and dried under reduced pressure yielding the crude product (7.7 g, 95.0% ee (S)) as a white solid. The crude product was recrystallised from t-BuOMe (150 mL), EtOH (200 mL) and MeOH (170 mL) at 80° C. The crystals formed after the solution cooled down were collected by filtration (3.3 g, 99.0% ee (S)) and the filtrate was concentrated under reduced pressure and was recrystallised again from t-BuOMe (100 mL) and MeOH (150 mL). The second crop of crystals were collected by filtration (1.3 g, 98.0% ee (S)) resulting in a combined yield of 4.6 g, 69% isolated yield). $^1$H NMR (400 MHz, D$_2$O+NaOH) δ ppm 8.81 (d, J=5.5 Hz, 1H), 8.55 (t, J=8.0 Hz, 1H), 8.06 (d, J=8.0 Hz, 1H), 7.99 (t, J=6.5 Hz, 1H), 4.53 (d, J=10.5 Hz, 1H), 2.63-2.50 (m, 1H), 2.11-2.01 (m, 1H), 1.84-1.40 (m, 6H), 1.24-1.12 (m, 1H). The ee of the compound was determined by acetylating small samples with AcCl (see example below for the synthesis) and analysing the products, (S)— and (R)—N-(Cyclopentyl(pyridin-2-yl)methyl)acetamides, by chiral HPLC: Daicel Chiralpak AD-H, C. (rac)-N-(Cyclopentyl(pyridin-2-yl)methyl)acetamide

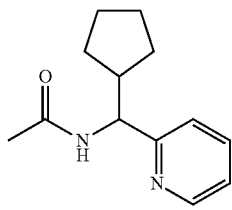 [SMILES: CC(=O)NC(c1ccccn1)C1CCCC1]

AcCl (0.10 g, 1.25 mmol) was added to a stirred suspension of Et₃N (0.35 mL, 0.25 g, 2.5 mmol, 2.2 eq.) and (rac)-1-cyclopentyl-1-(2-pyridinyl)methylamine HCl salt (0.25 g, 1.14 mmol) in CH₂Cl₂ (5 mL). The resulting mixture was stirred at rt for 2 h. The reaction mixture was washed with H₂O (10%, 3×3 mL) and was dried over Na₂SO₄ and was concentrated under reduced pressure yielding the crude product (0.20 g) as a clear yellow oil which quickly crystallized. $^1$H NMR (300 MHz, CDCl₃) δ ppm 8.53 (d, J=5.0 Hz, 1H), 7.62 (dt, J=1.5, 7.5 Hz, 1H), 7.28 (t, J=7.5 Hz, 1H), 7.16 (d, J=5.0 Hz, 1H), 6.72 (br d, J=7.0 Hz, 1H), 4.93 (t, J=9.0 Hz, 1H), 2.37-2.20 (m, 1H), 2.00 (s, 3H), 1.80-1.10 (m, 8H); HPLC: Daicel Chiralpak AD-H, 80:20 v/v heptane-EtOH (+0.2% Et₂NH), 1.0 mL min$^{-1}$, 210 nm, $R_t$=9.5 min, $R_t$=19.2 min.

Large scale asymmetric synthesis of (S)-1-(2-Chlorophenyl)-1-isopropylmethylamine HCl salt A. ($S_S$)—N—((S)-1-(2-Chlorophenyl)-2-methylpropyl)-2-methylpropane-2-sulfinamide

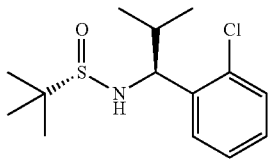 [SMILES: CC(C)[C@H](N[S@@](=O)C(C)(C)C)c1ccccc1Cl]

i-PrMgCl (2.0 M in THF, 46.2 mL, 92.3 mmol) was added carefully to stirred Me₂Zn (1.2 M in PhMe, 82 mL, 98.4 mmol) at rt. The resulting solution was stirred at rt for 30 min before being added dropwise, over 30 min, to a stirred −78° C. solution of (S,E)-N-(2-chlorobenzylidene)-2-methylpropane-2-sulfinamide (15.0 g, 61.5 mmol) in dry THF (350 mL). After the addition was complete the reaction mixture was stirred at −78° C. for 3 h before being quenched by careful addition of satd aq NH₄Cl (200 mL). The mixture was extracted with Et₂O (3×100 mL). The combined organic extracts were washed with brine (100 mL) and were dried (Na₂SO₄). The organic layer was concentrated under reduced pressure yielding the crude product (17.9 g, quantitative yield, 16:1 d.r. ($S_S$,S)—($S_S$,R) as a white solid which was used without any further purification. $^1$H NMR (300 MHz, CDCl₃) δ ppm 7.38-7.15 (m, 4H), 4.46 (t, J=8.0 Hz, 1H), 3.75 (br d, J=8.0 Hz, 1H), 2.28-2.15 (m, 1H), 1.22 (s, 9H), 1.01 (d, J=6.5 Hz, 3H), 0.85 (d, J=6.5 Hz, 3H).

B. (S)-1-(2-Chlorophenyl)-1-isopropylmethylamine HCl salt

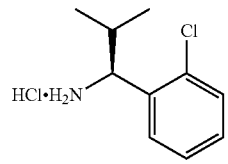

The title compound was synthesized according to General Method I utilizing HCl (2.0 M in Et₂O, 61.0 mL, 122.0 mmol) and a solution of ($S_S$)—N—((S)-1-(2-chlorophenyl)-2-methylpropyl)-2-methylpropane-2-sulfinamide (17.8 g, 61.0 mmol) in MeOH (175 mL). After the addition was complete the cooling bath was removed and the mixture was stirred at rt for 1 h. The reaction mixture was concentrated under reduced pressure and Et₂O (250 mL) was added and a white precipitation formed. The precipitation was filtered off and washed with Et₂O (2×200 mL) and dried under reduced pressure yielding the crude product (11.8 g, 88.7% ee (S)) as a white solid. The crude product was recrystallised from t-BuOMe (300 mL) and MeOH (48 mL) at 80° C. After having cooled down over night only a small amount of crystals had been formed which were removed by filtration. The filtrate was concentrated under reduced pressure and after roughly half the volume had been removed a second crop of solids appeared which was also removed by filtration. The two crops of crystals were found to be racemic by chiral HPLC. The filtrate was concentrated to dryness and recrystallised again from t-BuOMe (300 mL) and MeOH (33 mL) at 80° C. Again only a small amount of crystals were formed as the solution cooled down which were removed by filtration, as was a second crop of solids formed when the solution was concentrated under reduced pressure. The remaining filtrate was concentrated to dryness and was suspended in t-BuOMe (200 mL) and filtered off. The resulting white solid was washed with Et₂O (3×150 mL) and was dried under reduced pressure yielding the purified product (9.0 g, 67% isolated yield, 97% ee (S)) as a white solid. $^1$H NMR (400 MHz, D₂O+NaOH) δ ppm 7.59-7.41 (m, 4H), 4.60 (d, J=9.5 Hz, 1H), 2.44-2.30 (m, 1H), 1.18 (d, J=6.5 Hz, 3H), 0.85 (d, J=6.5 Hz, 3H; HPLC: Daicel Chiralpak AD-H, 97:3 v/v heptane-EtOH (+0.1% Et₃N), 1.0 mL/min, λ=280 nm, $R_t$=6.0 min (S), $R_t$=7.3 min (R).

Large scale asymmetric synthesis of (S)-1-(Cyclopentyl)-1-(3-thienyl)methylamine HCl salt A. ($S_S$)—N-((S)-Cyclopentyl(thiophen-3-yl)methyl)-2-methylpropane-2-sulfinamide

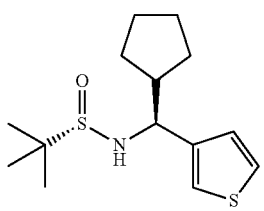 [SMILES: CC(C)(C)[S@](=O)N[C@H](c1ccsc1)C1CCCC1]

Cyclopentylmagnesium bromide (2.0 M in Et2O, 55.4 mL, 110.8 mmol) was added carefully to stirred dimethyl zinc (1.2 M in PhMe, 100 mL, 120 mmol) at rt. Dry THF (50 mL) was added and the mixture was stirred at rt for 30 min before being added slowly, dropwise over 30 min to a stirred −78° C. solution of (S,E)-N-(3-thienyl)-2-methylpropane-2-sulfinamide (19.9 g, 92.3 mmol) in dry THF (350 mL). Once the addition was complete the mixture was rapidly warmed up to −48° C. and was stirred at this temperature for 3 h. The reaction was quenched by addition of satd aq NH$_4$Cl (200 mL). H$_2$O (200 mL) was added and the mixture was extracted with Et$_2$O (3×100 mL). The combined organic extracts were washed with brine (100 mL), dried (Na$_2$SO$_4$) and concentrated under educed pressure yielding the crude product (31.4 g, 3:2 mixture of product and Me-added product, (S)-2-methyl-N-(1-(thiophen-3-yl)ethyl)propane-2-sulfinamide) as a clear yellow oil. The crude product was dissolved in 1:1 EtOAc-cyclohexane and was repeatedly columned through SiO$_2$ using 1:1 EtOAccyclohexane as eluent to yield the purified product (13.6 g, 52% isolated yield, >25:1 d.r. (S$_S$,S)—(S$_S$,R)) as a white solid. $^1$H NMR (400 MHz, CDCl$_3$) δ ppm 7.28 (dd, J=2.5, 5.0 Hz, 1H), 7.19 (d, J=2.5 Hz, 1H), 7.10 (d, J=5.0 Hz, 1H), 4.28 (t, J=7.5 Hz, 1H), 3.35 (d, J=6.5 Hz, 1H), 2.47-2.35 (m, 1H), 1.92-1.82 (m, 1H), 1.65-1.46 (m, 5H), 1.40-1.30 (m, 1H), 1.28-1.16 (m, 1H), 1.2 (s, 9H).

B. (S)-1-(Cyclopentyl)-1-(3-thienyl)methylamine HCl salt

The title compound was synthesized according to General Method I utilizing HCl (2.0 M in Et$_2$O, 47.3 mL, 94.6 mmol) and a solution of (S$_S$)—N-((S)-cyclopentyl(thiophen-3-yl)methyl)-2-methylpropane-2-sulfinamide (13.5 g, 47.3 mmol) in MeOH (135 mL). After the addition was complete the cooling bath was removed and the mixture was stirred at rt for 1 h. The reaction mixture was concentrated under reduced pressure and the residue was suspended in Et$_2$O (200 mL). The precipitation was filtered off and washed with Et$_2$O (2×200 mL) and dried under reduced pressure yielding the crude product (9.0 g, 92.9% ee (S)) as a white solid. The compound was suspended in t-BuOMe (150 mL), filtered and washed with Et$_2$O (2×100 mL) and dried under reduced pressure yielding the product (8.4 g, 82% isolated yield, 94.5% ee (S)) as a white solid. $^1$H NMR (400 MHz, D$_2$O+NaOH) δ ppm 7.57-7.52 (m, 2H), 7.23 (d, J=5.0 Hz, 1H), 4.31 (d, J=10.5 Hz, 1H), 2.56-2.43 (m, 1H), 2.04-1.94 (m, 1H), 1.80-1.48 (m, 5H), 1.46-1.34 (m, 1H), 1.24-1.09 (m, 1H); HPLC: Daicel Chiralcel OJ-H, 97:3 v/v heptane-EtOH (+0.2% Et$_3$N), 1.0 mL/min, X=230 nm, R$_f$=7.6 min (R), R$_f$=8.3 min (S).

Preparation of Exemplary Compounds of the Invention

Example A1

N-(3-(4-(2-oxa-6-azaspiro[3.3]heptan-6-yl)phenyl)-1H-indazol-5-yl)-2-(pyrrolidin-1-yl)-2-(thiophen-3-yl)acetamide

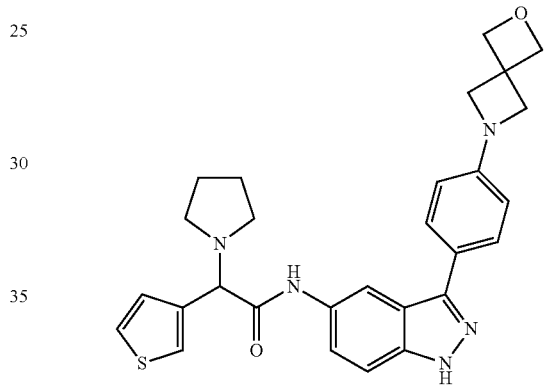

The title compound was synthesized according to General Method C1 by utilizing N-(3-iodo-1H-indazol-5-yl)-2-(pyrrolidin-1-yl)-2-(thiophen-3-yl)acetamide (200 mg, 0.45 mmol), 6-(4-(4,4,5,5-tetramethyl-1,3,2-dioxaborolan-2-yl)phenyl)-2-oxa-6-azaspiro[3.3]heptane (160 mg, 0.53 mmol), PdCl$_2$dppf.DCM (36 mg, 0.044 mmol) and 2 M aq Na$_2$CO$_3$ (0.5 mL) in PhMe/EtOH (12 mL, 2:1 mixture). The reaction mixture was heated under microwave irradiation at 130° C. for 3 h. The reaction mixture was diluted with EtOAc (10 mL) and washed with H$_2$O (5 mL), dried (MgSO$_4$) and concentrated under vacuum to give a crude product. Purification by flash chromatography (Biotage Isolera, 50 g HP-SIL, 100% EtOAc then 0-10% DCM in MeOH) followed by trituration with MeOH gave the title compound as a light brown solid (46 mg, 18%). $^1$H NMR (400 MHz, CDCl$_3$) δ ppm 9.21 (br. s., 1H), 8.38 (s, 1H), 7.83 (d, J=8.0 Hz, 2H), 7.48 (d, J=9.0 Hz, 1H), 7.42 (d, J=8.8 Hz, 1H), 7.29-7.36 (m, 2H), 7.15 (d, J=4.8 Hz, 1H), 6.58 (d, J=8.3 Hz, 2H), 4.87 (s, 4H), 4.15 (s, 1H), 4.09 (s, 4H), 2.61-2.75 (m, 2H), 2.47-2.60 (m, 2H), 1.76-1.92 (m, 4H); MS ESI 500.3 [M+H]$^+$, calcd for [C$_{28}$H$_{29}$N$_5$O$_2$S+H]$^+$ 500.2.

Example A2

(S)-3-(4-(2-oxa-6-azaspiro[3.3]heptan-6-yl)phenyl)-N-(cyclopentyl(pyridin-2-yl)methyl)-1H-indazole-5-carboxamide

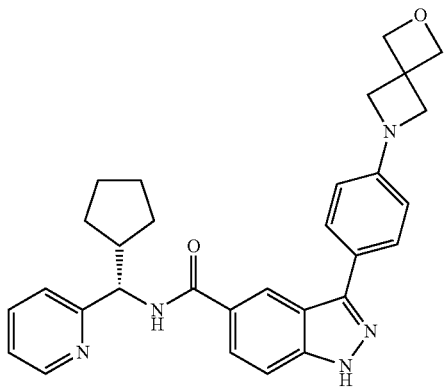 [SMILES: O=C(N[C@H](c1ccccn1)C1CCCC1)c1ccc2[nH]nc(-c3ccc(N4CC5(COC5)C4)cc3)c2c1]

A. Preparation of free base:

The title compound was synthesized according to General Method C2 by utilizing (S)—N-(cyclopentyl(pyridin-2-yl)methyl)-3-iodo-1H-indazole-5-carboxamide (135 mg, 0.30 mmol), 6-(4-(4,4,5,5-tetramethyl-1,3,2-dioxaborolan-2-yl)phenyl)-2-oxa-6-azaspiro[3.3]heptane (100 mg, 0.33 mmol), Pd(PPh$_3$)$_4$ (36 mg, 0.044 mmol) and 2 M aq Na$_2$CO$_3$ (0.3 mL) in PhMe/EtOH (14 mL, 1:1 mixture). The reaction mixture was heated under microwave irradiation at 130° C. for 3 h. The reaction mixture was diluted with EtOAc (20 mL) and washed with H$_2$O (20 mL), dried (MgSO$_4$) and concentrated under vacuum to give a crude product. Purification by flash chromatography (Biotage Isolera, 50 g HP-SIL, 60-100% EtOAc in hexanes then 0-20% DCM in MeOH) gave the product as a yellow solid. Further purification using reverse phase chromatography (Biotage Isolera, 50 g C18, 10-90% MeCN in H$_2$O) followed by trituration with MeOH gave the title compound as a pale yellow solid (34 mg, 23%). $^1$H NMR (400 MHz, DMSO-d$_6$) δ ppm 13.18 (s, 1H), 8.88 (d, J=8.3 Hz, 1H), 8.34-8.63 (m, 2H), 7.80-7.93 (m, 3H), 7.75 (t, J=6.9 Hz, 1H), 7.54 (d, J=8.5 Hz, 1H), 7.47 (d, J=8.0 Hz, 1H), 7.24 (t, J=5.3 Hz, 1H), 6.60 (d, J=8.5 Hz, 2H), 4.92 (t, J=9.0 Hz, 1H), 4.74 (s, 4H), 4.05 (s, 4H), 2.53-2.62 (m, 1H), 1.87 (s, 1H), 1.35-1.70 (m, 5H), 1.15-1.35 (m, 2H); MS ESI 494.4 [M+H]$^+$, calcd for [C$_{30}$H$_{31}$N$_5$O$_2$+H]$^+$ 494.3.

B. Preparation of p-toluenesulfonate salt

To a hot slurry of (S)-3-(4-(2-oxa-6-azaspiro[3.3]heptan-6-yl)phenyl)-N-(cyclopentyl(pyridin-2-yl)methyl)-1H-indazole-5-carboxamide (3.4 g, 6.9 mmol) in a mixture of acetone and MeOH (2:1, 200 mL) was added a solution of p-toluenesulfonic acid (1.3 g, 7.0 mmol) in acetone (10 mL). A clear yellow solution was obtained after the addition. Solvent was removed and the resulting salt was triturated with Et$_2$O (3×). Filtration under vacuum yielded the title compound as the p-toluenesulfonate salt (orange solid, 4.3 g, 94%). $^1$H NMR (400 MHz, CDCl$_3$) δ ppm 9.30 (br. s., 1H), 8.76 (d, J=5.8 Hz, 1H), 8.65 (s, 1H), 8.31 (t, J=7.5 Hz, 1H), 7.90-8.05 (m, 2H), 7.84 (d, J=8.5 Hz, 2H), 7.62-7.77 (m, 3H), 7.32 (d, J=8.5 Hz, 1H), 7.01 (d, J=8.0 Hz, 2H), 6.51 (d, J=8.3 Hz, 2H), 5.07 (dd, J=11.4, 7.4 Hz, 1H), 4.85 (s, 4H), 4.03 (s, 4H), 2.84-3.08 (m, 1H), 2.28 (s, 4H), 1.46-1.79 (m, 5H), 1.31-1.43 (m, 1H), 1.00-1.20 (m, 1H); MS ESI 494.4 [M+H]$^+$, calcd for [C$_{30}$H$_{31}$N$_5$O$_2$+H]$^+$ 494.3.

C. Preparation of benzenesulfonate salt

To a hot solution of (S)-3-(4-(2-oxa-6-azaspiro[3.3]heptan-6-yl)phenyl)-N-(cyclopentyl(pyridin-2-yl)methyl)-1H-indazole-5-carboxamide (20 mg, 0.041 mmol) in a mixture of MeOH and EtOAc (5:1, 2.4 mL) was added a solution of PhSO$_3$H (0.2 mL, 0.21 M) in EtOAc. A clear yellow solution was obtained after the addition. Solvent was removed and the resulting salt was triturated with EtOAc. Filtration under vacuum yielded the title compound as the PhSO$_3$H salt (yellow solid, 20 mg, 74%). $^1$H NMR (400 MHz, CDCl$_3$) δ ppm 9.37 (br. s., 1H), 8.76 (d, J=4.8 Hz, 1H), 8.72 (s, 1H), 8.37 (t, J=7.8 Hz, 1H), 8.03 (d, J=8.3 Hz, 2H), 7.89 (d, J=8.5 Hz, 2H), 7.74-7.84 (m, 3H), 7.29-7.38 (m, 2H), 7.19-7.26 (m, 2H), 6.56 (d, J=8.5 Hz, 2H), 5.08 (dd, J=10.7, 6.9 Hz, 1H), 4.86 (s, 4H), 4.06 (s, 4H), 2.92-3.05 (m, 1H), 2.20-2.33 (m, 1H), 1.47-1.80 (m, 5H), 1.32-1.44 (m, 1H), 1.06-1.21 (m, 1H); MS ESI 494.4 [M+H]$^+$, calcd for [C$_{30}$H$_{31}$N$_5$O$_2$+H]$^+$ 494.3.

The following final compounds were synthesized according to the synthesis of Example A1:

| Example/ IUPAC name | Structure | MS calculated | MS ESI [M + H]$^+$ | Yield; Appearance; Salt form |
|---|---|---|---|---|
| A3: 3-(4-(2-Oxa-6-azaspiro[3.3]heptan-6-yl)phenyl)-N-(cyclopropyl(o-tolyl)methyl)-1H-indazole-5-carboxamide | | [C$_{30}$H$_{30}$N$_4$O$_2$ + H]$^+$ 479.2 | 479.3 | 53 mg; light grey solid; free base |

| Example/ IUPAC name | Structure | MS calculated | MS ESI [M + H]⁺ | Yield; Appearance; Salt form |
|---|---|---|---|---|
| | Starting materials: N-(cyclopropyl(o-tolyl)methyl)-3-iodo-1H-indazole-5-carboxamide (260 mg, 0.61 mmol), 6-(4-(4,4,5,5-tetramethyl-1,3,2-dioxaborolan-2-yl)phenyl)-2-oxa-6-azaspiro[3.3]heptane (152 mg, 0.51 mmol) ¹H NMR (400 MHz, DMSO-d₆) δ ppm 13.17 (s, 1H), 8.91 (d, J = 7.8 Hz, 1H), 8.48 (s, 1H), 7.89 (d, J = 8.8 Hz, 1H), 7.82 (d, J = 8.3 Hz, 2H), 7.66 (d, J = 7.5 Hz, 1H), 7.54 (d, J = 8.5 Hz, 1H), 7.17-7.26 (m, 1H), 7.13 (d, J = 4.0 Hz, 2H), 6.59 (d, J = 8.5 Hz, 2H), 4.76-4.82 (m, 1H), 4.74 (s, 4H), 4.04 (s, 4H), 2.35 (s, 3H), 1.41 (s, 1H), 0.37-0.64 (m, 3H), 0.27 (d, J = 4.8 Hz, 1H) | | | |
| A24: 3-(4-(2-oxa-6-aza-spiro[3.3]heptan-6-yl)phenyl)-N-(cyclo-pentyl(pyrimidin-2-yl)methyl)-1H-indazole-5-carboxamide | 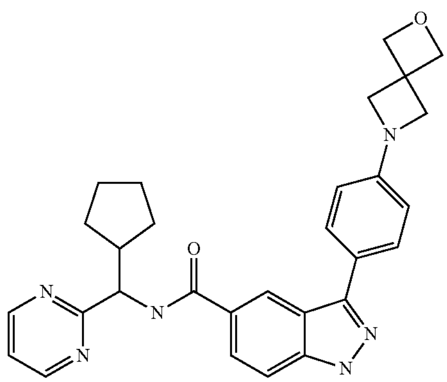 [SMILES: O=C(NC(c1ncccn1)C1CCCC1)c1ccc2[nH]nc(-c3ccc(N4CC5(COC5)C4)cc3)c2c1] | [C₂₉H₃₀N₆O₂ + H]⁺ 495.2 | 495.3 | 50 mg (44%); White powder; free base |
| | Starting materials: N-(cyclopentyl(pyrimidin-2-yl)methyl)-3-iodo-1H-indazole-5-carboxamide (0.10 g, 0.22 mmol), 6-(4-(4,4,5,5-tetramethyl-1,3,2-dioxaborolan-2-yl)phenyl)-2-oxa-6-azaspiro[3.3]heptanes (0.10 g, 0.33 mmol) ¹H NMR (400 MHz, DMSO-d₆) δ ppm 13.16 (s, 1H), 8.88 (d, J = 8.53 Hz, 1H), 8.78 (d, J = 5.02 Hz, 2H), 8.53 (s, 1H), 7.86 (d, J = 8.78 Hz, 2H), 7.54 (d, J = 8.53 Hz, 1H), 7.38 (t, J = 4.77 Hz, 1H), 6.60 (d, J = 8.53 Hz, 1H), 5.02 (t, J = 9.29 Hz, 1H), 2.47-2.61 (m, 1H), 1.80-1.93 (m, 1H), 1.23-1.67 (m, 6H) | | | |
| A25: (S)-3-(4-(2-oxa-6-aza-spiro[3.3]heptan-6-yl)phenyl)-N-(cyclo-pentyl(pyrimidin-2-yl)methyl)-1H-indazole-5-carboxamide | 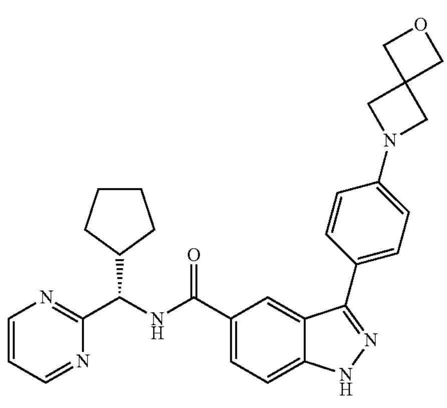 [SMILES: O=C(N[C@H](c1ncccn1)C1CCCC1)c1ccc2[nH]nc(-c3ccc(N4CC5(COC5)C4)cc3)c2c1] | [C₂₉H₃₀N₆O₂ + H]⁺ 495.2 | 495.4 | 104 mg (79%); pale yellow powder; free base |
| | Starting materials: (S)-N-(cyclopentyl(pyrimidin-2-yl)methyl)-3-iodo-1H-indazole-5-carboxamide (0.13 g, 0.29 mmol), 6-(4-(4,4,5,5-tetramethyl-1,3,2-dioxaborolan-2-yl)phenyl)-2-oxa-6-azaspiro[3.3]heptanes (0.105 g, 0.35 mmol) ¹H NMR (400 MHz, CD₃OD) δ ppm 8.79 (d, J = 5.02 Hz, 2H), 8.74 (d, J = 8.28 Hz, 1H), 8.58 (dd, J = 1.51, 0.75 Hz, 1H), 7.91 (dd, J = 8.78, 1.51 Hz, 1H), 7.84 (d, J = 8.80 Hz, 2H), 7.58 (d, J = 8.78 Hz, 1H), 7.38 (t, J = 5.02 Hz, 1H), 6.66 (d, J = 8.80 Hz, 2H), 5.18 (dd, J = 9.41, 8.16 Hz, 1H), 4.88 (s, 4H), 4.10 (s, 4H), 2.42-2.68 (m, 1H), 1.80-2.02 (m, 1H), 1.52-1.77 (m, 4H), 1.38-1.49 (m, 2H) | | | |

-continued

| Example/ IUPAC name | Structure | MS calculated | MS ESI [M + H]+ | Yield; Appearance; Salt form |
|---|---|---|---|---|
| A26: (R)-3-(4-(2-oxa-6-aza-spiro[3.3]heptan-6-yl)phenyl)-N-(cyclopentyl(pyrimidin-2-yl)methyl)-1H-indazole-5-carboxamide | | [C$_{29}$H$_{30}$N$_6$O$_2$ + H]$^+$ 495.2 | 495.4 | 92.8 mg (65%); white powder; free base |

Starting materials: (R)-N-(cyclopentyl(pyrimidin-2-yl)methyl)-3-iodo-1H-indazole-5-carboxamide (0.13 g, 0.29 mmol), 6-(4-(4,4,5,5-tetramethyl-1,3,2-dioxaborolan-2-yl)phenyl)-2-oxa-6-azaspiro[3.3]heptanes (0.105 g, 0.35 mmol)
$^1$H NMR (400 MHz, CD$_3$OD) δ ppm 8.79 (d, J = 5.02 Hz, 2H), 8.58 (s, 1H), 7.91 (m, J = 9.29 Hz, 1H), 7.84 (d, J = 8.53 Hz, 2H), 7.58 (d, J = 9.03 Hz, 1H), 7.39 (t, J = 4.89 Hz, 1H), 6.67 (d, J = 8.53 Hz, 2H), 5.18 (d, J = 9.54 Hz, 1H), 4.88 (s, 4H), 4.10 (s, 4H), 2.52-2.68 (m, 1H), 1.88-2.01 (m, 1H), 1.51-1.76 (m, 4H), 1.38-1.47 (m, 2H)

The following final compounds were synthesized according to the synthesis of Example A2:

| Example/ IUPAC name | Structure | MS calculated | MS ESI [M + H]+ | Yield; Appearance; Salt form |
|---|---|---|---|---|
| A4: 3-(4-(2-Oxa-6-aza-spiro[3.3]heptan-6-yl)phenyl)-N-(cyclopropyl(pyridin-2-yl)methyl)-1H-indazole-5-carboxamide | | [C$_{28}$H$_{27}$N$_5$O$_2$ + H]$^+$ 466.2 | 466.3 | 21 mg (17%); yellow solid; free base |

Starting materials: N-(Cyclopropyl(pyridin-2-yl)methyl)-3-iodo-1H-indazole-5-carboxamide (120 mg, 0.29 mmol), 6-(4-(4,4,5,5-tetramethyl-1,3,2-dioxaborolan-2-yl)phenyl)-2-oxa-6-azaspiro[3.3]heptane (120 mg, 0.40 mmol)
$^1$H NMR (400 MHz, CDCl$_3$) δ ppm 8.61 (d, J = 4.5 Hz, 1H), 8.58 (s, 1H), 7.92 (d, J = 8.3 Hz, 1H), 7.77-7.86 (m, 3H), 7.71 (td, J = 7.8, 1.8 Hz, 1H), 7.37 (t, J = 8.7 Hz, 2H), 7.22-7.27 (m, 1H), 6.51 (d, J = 8.5 Hz, 2H), 4.86 (s, 4H), 4.80 (t, J = 8.2 Hz, 1H), 4.07 (s, 4H), 1.33-1.44 (m, 1H), 0.43-0.73 (m, 4H)

-continued

| Example/ IUPAC name | Structure | MS calculated | MS ESI [M + H]⁺ | Yield; Appearance; Salt form |
|---|---|---|---|---|
| A5: (S)-3-(4-(2-Oxa-6-aza-spiro[3.3]heptan-6-yl)phenyl)-N-(cyclopropyl(pyridin-2-yl)methyl)-1H-indazole-5-carboxamide | | $[C_{28}H_{27}N_5O_2 + H]^+$ 466.2 | 466.3 | 81 mg (48%); yellow solid; free base |

Starting materials: (S)-N-(yclopropyl(pyridin-2-yl)methyl)-3-iodo-1H-indazole-5-carboxamide (150 mg, 0.36 mmol), 6-(4-(4,4,5,5-tetramethyl-1,3,2-dioxaborolan-2-yl)phenyl)-2-oxa-6-azaspiro[3.3]heptane (119 mg, 0.39 mmol)
¹H NMR: Spectral data was identical for that obtained in Example A4

| A6: (R)-3-(4-(2-oxa-6-aza-spiro[3.3]heptan-6-yl)phenyl)-N-(cyclopropyl(pyridin-2-yl)methyl)-1H-indazole-5-carboxamide | | $[C_{28}H_{27}N_5O_2 + H]^+$ 466.2 | 466.3 | 30 mg (27%); white solid; free base |

Starting materials: (R)-N-(cyclopropyl(pyridin-2-yl)methyl)-3-iodo-1H-indazole-5-carboxamide (100 mg, 0.24 mmol), 6-(4-(4,4,5,5-tetramethyl-1,3,2-dioxaborolan-2-yl)phenyl)-2-oxa-6-azaspiro[3.3]heptane (79 mg, 0.26 mmol)
¹H NMR (400 MHz, DMSO-$d_6$) δ ppm 13.19 (s, 1H), 9.09 (d, J = 7.8 Hz, 1H), 8.56 (s, 1H), 8.52 (d, J = 3.8 Hz, 1H), 7.91 (d, J = 9.3 Hz, 1H), 7.85 (d, J = 8.5 Hz, 2H), 7.77 (td, J = 7.8, 1.8 Hz, 1H), 7.55 (d, J = 8.8 Hz, 1H), 7.50 (d, J = 7.5 Hz, 1H), 7.23-7.29 (m, 1H), 6.60 (d, J = 8.3 Hz, 2H), 4.74 (s, 4H), 4.48 (t, J = 8.5 Hz, 1H), 4.05 (s, 4H), 1.43 (br. s., 1H), 0.41-0.60 (m, 4H)

| A7: 3-(4-(2-Oxa-6-aza-spiro[3.3]heptan-6-yl)phenyl)-N-(cyclopentyl(pyridin-2-yl)methyl)-1H-indazole-5-carboxamide | | $[C_{30}H_{31}N_5O_2 + H]^+$ 494.3 | 494.3 | 43 mg (25%); pale yellow solid; free base |

| Example/ IUPAC name | Structure | MS calculated | MS ESI [M + H]⁺ | Yield; Appearance; Salt form |
|---|---|---|---|---|

Starting materials: N-(cyclopentyl(pyridin-2-yl)methyl)-3-iodo-1H-indazole-5-carboxamide (153 mg, 0.34 mmol), 6-(4-(4,4,5,5-tetramethyl-1,3,2-dioxaborolan-2-yl)phenyl)-2-oxa-6-azaspiro[3.3]heptane (124 mg, 0.41 mmol)

$^1$H NMR (400 MHz, CDCl$_3$) δ ppm 10.81 (br. s., 1H), 8.42-8.70 (m, 2H), 7.76-7.91 (m, 3H), 7.62-7.74 (m, 2H), 7.32-7.47 (m, 2H), 7.28 (d, J = 5.5 Hz, 1H), 6.52 (t, J = 7.8 Hz, 2H), 5.16-5.28 (m, 1H), 4.88 (d, J = 5.5 Hz, 4H), 4.09 (d, J = 5.5 Hz, 4H), 2.42-2.60 (m, 1H), 1.23-1.92 (m, 8H)

| A8: (R)-3-(4-(2-Oxa-6-aza-spiro[3.3]heptan-6-yl)phenyl)-N-(cyclopentyl(pyridin-2-yl)methyl)-1H-indazole-5-carboxamide | 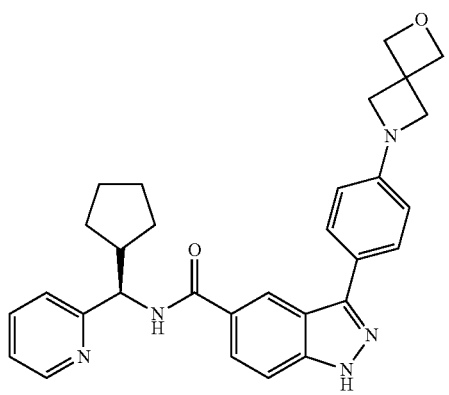 [SMILES: O=C(N[C@@H](c1ncccn1)C1CCCC1)c1ccc2[nH]nc(-c3ccc(N4CC5(COC5)C4)cc3)c2c1] | [C$_{30}$H$_{31}$N$_5$O$_2$ + H]⁺ 494.3 | 494.3 | 32 mg (22%); pale yellow solid; free base |

Starting materials: (R)-N-(cyclopentyl(pyridin-2-yl)methyl)-3-iodo-1H-indazole-5-carboxamide (135 mg, 0.30 mmol), 6-(4-(4,4,5,5-tetramethyl-1,3,2-dioxaborolan-2-yl)phenyl)-2-oxa-6-azaspiro[3.3]heptane (100 mg, 0.33 mmol)

$^1$H NMR: Spectral data was identical for that obtained in Example A2

| A9: 3-(4-(2-Oxa-6-aza-spiro[3.3]heptan-6-yl)phenyl)-N-((R)-cyclopentyl(thiophen-3-yl)methyl)-1H-indazole-5-carboxamide | 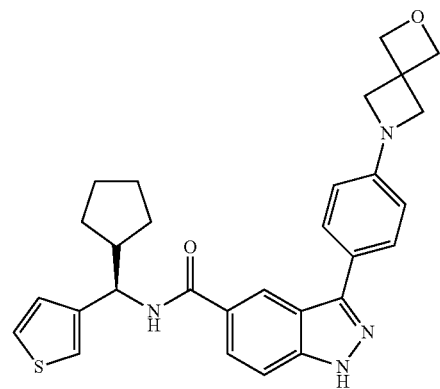 [SMILES: O=C(N[C@@H](c1ccsc1)C1CCCC1)c1ccc2[nH]nc(-c3ccc(N4CC5(COC5)C4)cc3)c2c1] | [C$_{29}$H$_{30}$N$_4$O$_2$S + H]⁺ 499.2 | 499.3 | 13 mg (8%); light tan solid; free base |

Starting materials: (R)-N-(cyclopentyl(thiophen-3-yl)methyl)-3-iodo-1H-indazole-5-carboxamide (150 mg, 0.33 mmol), 6-(4-(4,4,5,5-tetramethyl-1,3,2-dioxaborolan-2-yl)phenyl)-2-oxa-6-azaspiro[3.3]heptane (120 mg, 0.40 mmol)

$^1$H NMR (400 MHz, DMSO-d$_6$) δ ppm 13.18 (s, 1H), 8.76 (d, J = 8.5 Hz, 1H), 8.45 (s, 1H), 7.70-7.99 (m, 3H), 7.55 (d, J = 8.8 Hz, 1H), 7.42-7.49 (m, 1H), 7.39 (br. s., 1H), 7.21 (d, J = 4.8 Hz, 1H), 6.60 (d, J = 8.5 Hz, 2H), 4.99 (t, J = 9.5 Hz, 1H), 4.74 (s, 4H), 4.05 (s, 4H), 1.74-1.88 (m, 1H), 1.32-1.68 (m, 6H), 1.11-1.27 (m, 1H)

| Example/ IUPAC name | Structure | MS calculated | MS ESI [M + H]⁺ | Yield; Appearance; Salt form |
|---|---|---|---|---|
| A10: 3-(4-(2-Oxa-6-aza-spiro[3.3]heptan-6-yl)phenyl)-N-((S)-cyclopropyl(phenyl)methyl)-1H-indazole-5-carboxamide | | $[C_{29}H_{28}N_4O_2 + H]^+$ 465.2 | 465.3 | 15 mg (13%); pale yellow solid; free base |

Starting materials: (S)-N-(cyclopropyl(phenyl)methyl)-3-iodo-1H-indazole-5-carboxamide (101 mg, 0.24 mmol), 6-(4-(4,4,5,5-tetramethyl-1,3,2-dioxaborolan-2-yl)phenyl)-2-oxa-6-azaspiro[3.3]heptane (80 mg, 0.27 mmol)

$^1$H NMR (400 MHz, DMSO-d$_6$) δ ppm 13.18 (s, 1H), 9.07 (d, J = 7.5 Hz, 1H), 8.53 (s, 1H), 7.92 (d, J = 8.5 Hz, 1H), 7.84 (d, J = 8.3 Hz, 2H), 7.56 (d, J = 9.0 Hz, 1H), 7.48 (d, J = 7.5 Hz, 2H), 7.34 (t, J = 7.8 Hz, 2H), 7.24 (m, J = 7.8 Hz, 1H), 6.60 (d, J = 8.5 Hz, 2H), 4.74 (s, 4H), 4.43 (t, J = 8.7 Hz, 1H), 4.04 (s, 4H), 1.30-1.43 (m, 1H), 0.57 (d, J = 8.0 Hz, 2H), 0.34-0.47 (m, 2H)

| Example/ IUPAC name | Structure | MS calculated | MS ESI [M + H]⁺ | Yield; Appearance; Salt form |
|---|---|---|---|---|
| A11: 3-(4-(2-Oxa-6-aza-spiro[3.3]heptan-6-yl)phenyl)-N-(1-(2-chlorophenyl)-2-methylpropyl)-1H-indazole-5-carboxamide | 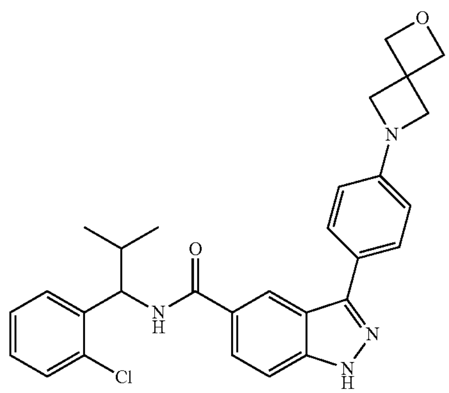 | $[C_{29}H_{29}ClN_4O_2 + H]^+$ 501.2 | 501.5 | 49 mg (30%); light orange solid; free base |

Starting materials: N-(1-(2-chlorophenyl)-2-methylpropyl)-3-iodo-1H-indazole-5-carboxamide (147 mg, 0.32 mmol), 6-(4-(4,4,5,5-tetramethyl-1,3,2-dioxaborolan-2-yl)phenyl)-2-oxa-6-azaspiro[3.3]heptane (118 mg, 0.39 mmol)

$^1$H NMR (400 MHz, DMSO-d$_6$) δ ppm 13.18 (s, 1H), 8.80 (d, J = 8.5 Hz, 1H), 8.46 (s, 1H), 7.74-7.92 (m, 3H), 7.66 (d, J = 6.3 Hz, 1H), 7.56 (d, J = 8.8 Hz, 1H), 7.41 (d, J = 7.8 Hz, 1H), 7.35 (t, J = 7.2 Hz, 1H), 7.21-7.28 (m, 1H), 6.60 (d, J = 8.5 Hz, 2H), 5.27 (t, J = 8.8 Hz, 1H), 4.74 (s, 4H), 4.05 (s, 4H), 2.10-2.24 (m, 1H), 1.08 (d, J = 6.5 Hz, 3H), 0.79 (d, J = 6.8 Hz, 3H)

| Example/ IUPAC name | Structure | MS calculated | MS ESI [M + H]⁺ | Yield; Appearance; Salt form |
|---|---|---|---|---|
| A12: 3-(4-(2-Oxa-6-aza-spiro[3.3]heptan-6-yl)phenyl)-N-((S)-1-(2-chlorophenyl)-2-methylpropyl)-1H-indazole-5-carboxamide | 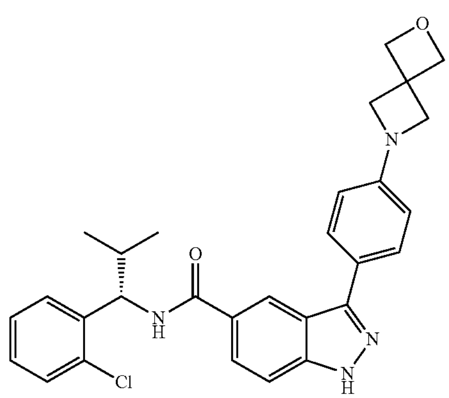 [SMILES: CC(C)[C@H](NC(=O)c1ccc2[nH]nc(-c3ccc(N4CC5(COC5)C4)cc3)c2c1)c1ccccc1Cl] | $[C_{29}H_{29}ClN_4O_2 + H]^+$ 501.2 | 501.5 | 22 mg (15%); pale yellow solid; free base |

| Example/ IUPAC name | Structure | MS calculated | MS ESI [M + H]+ | Yield; Appearance; Salt form |
|---|---|---|---|---|
| | Starting materials: (S)-N-(1-(2-chlorophenyl)-2-methylpropyl)-3-iodo-1H-indazole-5-carboxamide (137 mg, 0.30 mmol), 6-(4-(4,4,5,5-tetramethyl-1,3,2-dioxaborolan-2-yl)phenyl)-2-oxa-6-azaspiro[3.3]heptane (100 mg, 0.33 mmol) ¹H NMR: Spectral data was identical for that obtained in Example A11 | | | |
| A13: 3-(4-(2-Oxa-6-aza-spiro[3.3]heptan-6-yl)phenyl)-N-((R)-1-(2-chlorophenyl)-2-methylpropyl)-1H-indazole-5-carboxamide | | [C₂₉H₂₉ClN₄O₂ + H]⁺ 501.2 | 501.5 | 43 mg (29%); pale yellow solid; free base |
| | Starting materials: (R)-N-(1-(2-chlorophenyl)-2-methylpropyl)-3-iodo-1H-indazole-5-carboxamide (137 mg, 0.30 mmol), 6-(4-(4,4,5,5-tetramethyl-1,3,2-dioxaborolan-2-yl)phenyl)-2-oxa-6-azaspiro[3.3]heptane (100 mg, 0.33 mmol) ¹H NMR: Spectral data was identical for that obtained in Example A11 | | | |
| A14: 3-(4-(2-Oxa-6-aza-spiro[3.3]heptan-6-yl)phenyl)-N-(cyclopropyl(thiazol-2-yl)methyl)-1H-indazole-5-carboxamide | | [C₂₆H₂₅N₅O₂S + H]⁺ 472.2 | 472.2 | 30 mg (24%); yellow solid; free base |
| | Starting materials: N-(Cyclopropyl(thiazol-2-yl)methyl)-3-iodo-1H-indazole-5-carboxamide (124 mg, 0.29 mmol), 6-(4-(4,4,5,5-tetramethyl-1,3,2-dioxaborolan-2-yl)phenyl)-2-oxa-6-azaspiro[3.3]heptane (80 mg, 0.27 mmol) ¹H NMR (400 MHz, DMSO-d₆) δ ppm 13.19 (s, 1H), 9.32 (d, J = 8.0 Hz, 1H), 8.58 (s, 1H), 7.93 (d, J = 8.8 Hz, 1H), 7.85 (d, J = 8.3 Hz, 2H), 7.75 (d, J = 2.5 Hz, 1H), 7.63 (d, J = 2.8 Hz, 1H), 7.58 (d, J = 8.8 Hz, 1H), 6.60 (d, J = 8.3 Hz, 2H), 4.74 (s, 5H), 4.05 (s, 4H), 1.48-1.62 (m, 1H), 0.42-0.74 (m, 4H) | | | |
| A15: 3-(4-(2-Oxa-7-aza-spiro[3.5]nonan-7-yl)phenyl)-N-(cyclopropyl(pyridin-2-yl)methyl)-1H-indazole-5-carboxamide | | [C₃₀H₃₁N₅O₂ + H]⁺ 494.3 | 494.3 | 50 mg (25%); yellow solid; free base |

| Example/ IUPAC name | Structure | MS calculated | MS ESI [M + H]+ | Yield; Appearance; Salt form |
|---|---|---|---|---|
| | Starting materials: N-(Cyclopropyl(pyridin-2-yl)methyl)-3-iodo-1H-indazole-5-carboxamide (170 mg, 0.41 mmol), 7-(4-(4,4,5,5-Tetramethyl-1,3,2-dioxaborolan-2-yl)phenyl)-2-oxa-7-azaspiro[3.5]nonane (200 mg, 0.49 mmol) | | | |
| | $^1$H NMR (400 MHz, CDCl$_3$) δ ppm 12.32 (br. s., 1H), 8.62 (d, J = 4.0 Hz, 1H), 8.59 (s, 1H), 8.18 (d, J = 7.5 Hz, 1H), 7.74-7.83 (m, 3H), 7.70 (td, J = 7.7, 1.8 Hz, 1H), 7.36 (d, J = 7.8 Hz, 1H), 7.20-7.29 (m, 2H), 6.86 (d, J = 8.8 Hz, 2H), 4.78 (t, J = 8.3 Hz, 1H), 4.45 (s, 4H), 3.03-3.13 (m, 4H), 1.90-1.99 (m, 4H), 1.35-1.47 (m, 1H), 0.42-0.72 (m, 4H) | | | |
| A16: 3-(4-(2-Oxa-6-aza-spiro[3.4]octan-6-yl)phenyl)-N-(cyclo-propyl(pyridin-2-yl)methyl)-1H-indazole-5-carboxamide | 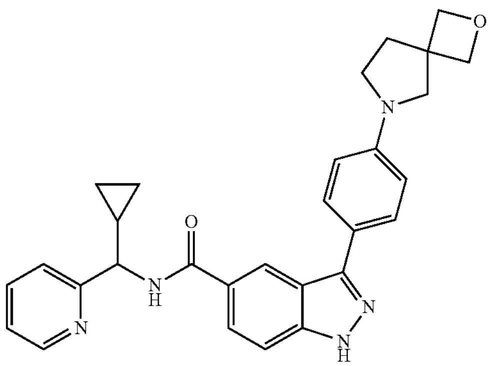 [SMILES: O=C(NC(c1ccccn1)C1CC1)c1ccc2[nH]nc(-c3ccc(N4CCC5(COC5)C4)cc3)c2c1] | [C$_{29}$H$_{29}$N$_5$O$_2$ + H]+ 480.2 | 480.3 | 74 mg (41%); yellow solid; free base |
| | Starting materials: N-(Cyclopropyl(pyridin-2-yl)methyl)-3-iodo-1H-indazole-5-carboxamide (157 mg, 0.38 mmol), 6-(4-(4,4,5,5-Tetramethyl-1,3,2-dioxaborolan-2-yl)phenyl)-2-oxa-6-azaspiro[3.4]octane (120 mg, 0.38 mmol) | | | |
| | $^1$H NMR (400 MHz, CDCl$_3$) δ ppm 12.23 (br. s., 1H), 8.45-8.76 (m, 2H), 8.17 (d, J = 7.3 Hz, 1H), 7.73-7.84 (m, 3H), 7.70 (td, J = 7.7, 1.5 Hz, 1H), 7.36 (d, J = 7.8 Hz, 1H), 7.19-7.30 (m, 2H), 6.50 (d, J = 8.5 Hz, 2H), 4.78 (t, J = 8.2 Hz, 1H), 4.70 (d, J = 6.0 Hz, 2H), 4.62 (d, J = 6.0 Hz, 2H), 3.50 (s, 2H), 3.29 (t, J = 6.8 Hz, 2H), 2.27 (t, J = 6.9 Hz, 2H), 1.35-1.47 (m, 1H), 0.40-0.73 (m, 4H) | | | |
| A17: (S)-3-(4-(7-Oxa-2-aza-spiro[3.5]nonan-2-yl)phenyl)-N-(cyclo-propyl(phenyl)meth-yl)-1H-indazole-5-carboxamide | 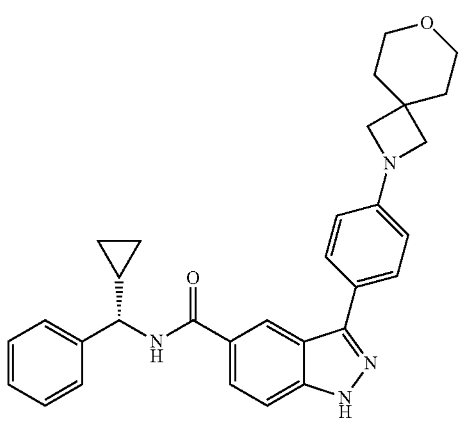 [SMILES: O=C(N[C@H](c1ccccc1)C1CC1)c1ccc2[nH]nc(-c3ccc(N4CC5(CCOCC5)C4)cc3)c2c1] | [C$_{31}$H$_{32}$N$_4$O$_2$ + H]+ 493.3 | 493.4 | 25 mg (17%); white solid; free base |
| | Starting materials: (S)-N-(cyclopropyl(phenyl)methyl)-3-iodo-1H-indazole-5-carboxamide (125 mg, 0.30 mmol), 2-(4-(4,4,5,5-Tetramethyl-1,3,2-dioxaborolan-2-yl)phenyl)-7-oxa-2-azaspiro[3.5]nonane (126 mg, 0.30 mmol) | | | |
| | $^1$H NMR (400 MHz, CDCl$_3$) δ ppm 10.10 (br. s., 1H), 8.53 (s, 1H), 7.85 (d, J = 8.3 Hz, 3H), 7.43-7.57 (m, 3H), 7.38 (t, J = 7.5 Hz, 2H), 7.29-7.33 (m, 1H), 6.53-6.65 (m, 3H), 4.70 (t, J = 8.0 Hz, 1H), 3.75 (s, 4H), 3.68-3.73 (m, 4H), 1.88 (t, J = 4.9 Hz, 4H), 1.25-1.37 (m, 1H), 0.45-0.76 (m, 4H) | | | |

| Example/ IUPAC name | Structure | MS calculated | MS ESI [M + H]+ | Yield; Appearance; Salt form |
|---|---|---|---|---|
| A18: (S)-3-(4-(7-Oxa-2-aza-spiro[3.5]nonan-2-yl)phenyl)-N-(cyclopropyl(pyridin-2-yl)methyl)-1H-indazole-5-carboxamide | | [C₃₀H₃₁N₅O₂ + H]⁺ 494.3 | 494.4 | 29 mg (21%); pale yellow solid; free base |
| | Starting materials: (S)-N-(yclopropyl(pyridin-2-yl)methyl)-3-iodo-1H-indazole-5-carboxamide (117 mg, 0.28 mmol), 2-(4-(4,4,5,5-Tetramethyl-1,3,2-dioxaborolan-2-yl)phenyl)-7-oxa-2-azaspiro[3.5]nonane (130 mg, 0.31 mmol) ¹H NMR (400 MHz, CD₃OD) δ ppm 8.64 (s, 1H), 8.53 (d, J = 4.3 Hz, 1H), 7.95 (d, J = 9.0 Hz, 1H), 7.79-7.90 (m, 3H), 7.57 (dd, J = 12.9, 8.4 Hz, 2H), 7.28-7.39 (m, 1H), 6.66 (d, J = 8.3 Hz, 2H), 4.51 (d, J = 9.5 Hz, 1H), 3.74 (s, 4H), 3.71 (t, J = 5.3 Hz, 4H), 1.88 (t, J = 5.3 Hz, 4H), 1.37-1.47 (m, 1H), 0.67-0.75 (m, 1H), 0.52-0.63 (m, 3H) | | | |
| A19: (S)-3-(4-(7-Oxa-2-aza-spiro[3.5]nonan-2-yl)phenyl)-N-(cyclopentyl(pyridin-2-yl)methyl)-1H-indazole-5-carboxamide | | [C₃₂H₃₅N₅O₂ + H]⁺ 522.3 | 522.4 | 22 mg (14%); white solid; free base |
| | Starting materials: (S)-N-(cyclopentyl(pyridin-2-yl)methyl)-3-iodo-1H-indazole-5-carboxamide (133 mg, 0.30 mmol), 2-(4-(4,4,5,5-Tetramethyl-1,3,2-dioxaborolan-2-yl)phenyl)-7-oxa-2-azaspiro[3.5]nonane (126 mg, 0.30 mmol) ¹H NMR (400 MHz, DMSO-d₆) δ ppm 13.15 (br. s, 1H), 8.87 (d, J = 8.3 Hz, 1H), 8.42-8.58 (m, 2H), 7.79-7.94 (m, 3H), 7.70-7.78 (m, 1H), 7.54 (d, J = 9.0 Hz, 1H), 7.47 (d, J = 7.8 Hz, 1H), 7.18-7.30 (m, 1H), 6.59 (d, J = 8.5 Hz, 2H), 4.93 (t, J = 9.5 Hz, 1H), 3.67 (s, 4H), 3.50-3.62 (m, 4H), 2.54-2.64 (m, 1H), 1.69-1.94 (m, 4H), 1.37-1.67 (m, 4H), 1.14-1.36 (m, 2H) | | | |
| A20: (S)-3-(4-(1-oxa-6-aza-spiro[3.3]heptan-6-yl)phenyl)-N-(cyclopentyl(pyridin-2-yl)methyl)-1H-indazole-5-carboxamide | | [C₃₀H₃₁N₅O₂ + H]⁺ 494.3 | 494.4 | 67 mg (34%); yellow solid; TFA salt |

| Example/ IUPAC name | Structure | MS calculated | MS ESI [M + H]+ | Yield; Appearance; Salt form |
|---|---|---|---|---|
| | Starting materials: (S)-N-(cyclopentyl(pyridin-2-yl)methyl)-3-iodo-1H-indazole-5-carboxamide (148 mg, 0.33 mmol), 6-(4-(4,4,5,5-Tetramethyl-1,3,2-dioxaborolan-2-yl)phenyl)-1-oxa-6-azaspiro[3.3]heptane (100 mg, 0.33 mmol) <br> ¹H NMR (400 MHz, CDCl₃) δ ppm 9.92 (d, J = 7.0 Hz, 1H), 8.76 (d, J = 5.3 Hz, 1H), 8.70 (s, 1H), 8.30 (t, J = 7.5 Hz, 1H), 8.06 (d, J = 8.8 Hz, 1H), 8.00 (d, J = 7.8 Hz, 1H), 7.85 (d, J = 8.3 Hz, 2H), 7.72 (t, J = 6.5 Hz, 1H), 7.50 (d, J = 8.8 Hz, 1H), 6.64 (d, J = 8.0 Hz, 2H), 5.12 (dd, J = 10.9, 7.7 Hz, 1H), 4.61 (t, J = 7.4 Hz, 2H), 4.26 (d, J = 9.0 Hz, 2H), 4.13 (d, J = 9.3 Hz, 2H), 2.97 (t, J = 7.4 Hz, 2H), 2.70-2.87 (m, 1H), 2.20-2.19 (m 1H), 1.47-1.80 (m, 5H), 1.39-1.37 (m, 1H), 1.03-1.20 (m, 1H) | | | |
| A21: (S)-3-(4-(1-Oxa-6-aza-spiro[3.3]heptan-6-yl)phenyl)-N-(cyclopropyl(pyridin-2-yl)methyl)-1H-indazole-5-carboxamide | | [C₂₈H₂₇N₅O₂ + H]+ 466.2 | 466.3 | 46 mg (30%); Pale yellow solid; free base |
| | Starting materials: (S)-N-(yclopropyl(pyridin-2-yl)methyl)-3-iodo-1H-indazole-5-carboxamide (139 mg, 0.33 mmol), 6-(4-(4,4,5,5-Tetramethyl-1,3,2-dioxaborolan-2-yl)phenyl)-1-oxa-6-azaspiro[3.3]heptane (100 mg, 0.33 mmol) <br> ¹H NMR (400 MHz, DMSO-d₆) δ ppm 13.15 (s, 1H), 9.02 (d, J = 7.5 Hz, 1H), 8.56 (s, 1H), 8.52 (d, J = 4.5 Hz, 1H), 7.91 (d, J = 10.3 Hz, 1H), 7.85 (d, J = 8.5 Hz, 2H), 7.72-7.79 (m, 1H), 7.55 (d, J = 8.8 Hz, 1H), 7.51 (d, J = 7.5 Hz, 1H), 7.20-7.30 (m, 1H), 6.61 (d, J = 8.3 Hz, 2H), 4.46 (t, J = 7.5 Hz, 3H), 4.16 (d, J = 8.5 Hz, 2H), 3.93 (d, J = 9.5 Hz, 2H), 2.90 (t, J = 7.5 Hz, 2H), 1.36-1.49 (m, 1H), 0.37-0.63 (m, 4H) | | | |
| A22: (R)-3-(4-(1-Oxa-6-aza-spiro[3.3]heptan-6-yl)phenyl)-N-(cyclopropyl(pyridin-2-yl)methyl)-1H-indazole-5-carboxamide | | [C₂₈H₂₇N₅O₂ + H]+ 466.2 | 466.3 | 98 mg (47%); yellow solid; p-toluene sulfonate salt |
| | Starting materials: (R)-N-(yclopropyl(pyridin-2-yl)methyl)-3-iodo-1H-indazole-5-carboxamide (139 mg, 0.33 mmol), 6-(4-(4,4,5,5-Tetramethyl-1,3,2-dioxaborolan-2-yl)phenyl)-1-oxa-6-azaspiro[3.3]heptane (100 mg, 0.33 mmol) <br> ¹H NMR (400 MHz, CD₃OD) δ ppm 8.75 (dd, J = 5.8, 0.8 Hz, 1H), 8.67 (s, 1H), 8.54 (td, J = 8.0, 1.6 Hz, 1H), 8.18 (d, J = 8.0 Hz, 1H), 7.96 (dd, J = 8.8, 1.5 Hz, 1H), 7.89-7.94 (m, 1H), 7.85 (d, J = 8.5 Hz, 2H), 7.69 (d, J = 8.0 Hz, 2H), 7.60 (dd, J = 8.8, 0.8 Hz, 1H), 7.20 (d, J = 7.8 Hz, 2H), 6.67 (d, J = 8.8 Hz, 2H), 4.60 (t, J = 7.7 Hz, 2H), 4.48 (d, J = 10.0 Hz, 1H), 4.20 (d, J = 9.8 Hz, 2H), 4.01 (d, J = 10.0 Hz, 2H), 2.98 (t, J = 7.5 Hz, 2H), 2.36 (s, 3H), 1.47-1.57 (m, 1H), 0.86-0.94 (m, 1H), 0.56-0.81 (m, 3H) | | | |

| Example/ IUPAC name | Structure | MS calculated | MS ESI [M + H]+ | Yield; Appearance; Salt form |
| --- | --- | --- | --- | --- |
| A23: (S)-3-(4-(1-Oxa-6-aza-spiro[3.3]heptan-6-yl)phenyl)-N-(1-(2-chlorophenyl)-2-methylpropyl)-1H-indazole-5-carboxamide | 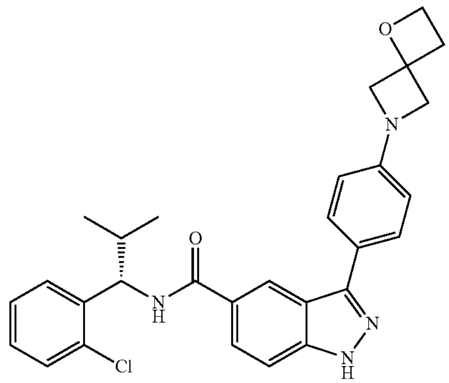 [SMILES: CC(C)[C@H](NC(=O)c1ccc2[nH]nc(-c3ccc(N4CC5(CCO5)C4)cc3)c2c1)c1ccccc1Cl] | [$C_{29}H_{29}ClN_4O_2$ + H]+ 501.2 | 501.5 | 27 mg (16%); yellow solid; free base |
| Starting materials: (S)-N-(1-(2-chlorophenyl)-2-methylpropyl)-3-iodo-1H-indazole-5-carboxamide (150 mg, 0.33 mmol), 6-(4-(4,4,5,5-Tetramethyl-1,3,2-dioxaborolan-2-yl)phenyl)-1-oxa-6-azaspiro[3.3]heptane (100 mg, 0.33 mmol) ¹H NMR (400 MHz, DMSO-d₆) δ ppm 13.16 (br. s., 1H), 8.76 (d, J = 8.5 Hz, 1H), 8.47 (s, 1H), 7.74-7.91 (m, 3H), 7.66 (d, J = 6.3 Hz, 1H), 7.56 (d, J = 8.5 Hz, 1H), 7.40 (d, J = 7.8 Hz, 1H), 7.31-7.37 (m, 1H), 7.21-7.27 (m, 1H), 6.62 (d, J = 8.8 Hz, 2H), 5.28 (t, J = 9.2 Hz, 1H), 4.46 (t, J = 7.5 Hz, 2H), 4.16 (d, J = 9.5 Hz, 2H), 3.93 (d, J = 9.0 Hz, 2H), 2.90 (t, J = 7.5 Hz, 2H), 2.12-2.24 (m, 1H), 1.08 (d, J = 6.5 Hz, 3H), 0.79 (d, J = 6.8 Hz, 3H) | | | |
| A27: (S)-3-(4-(2-oxa-6-aza-spiro[3.3]heptan-6-yl)phenyl)-N-(3-methyl-1-(pyridin-2-yl)butyl)-1H-indazole-5-carboxamide | 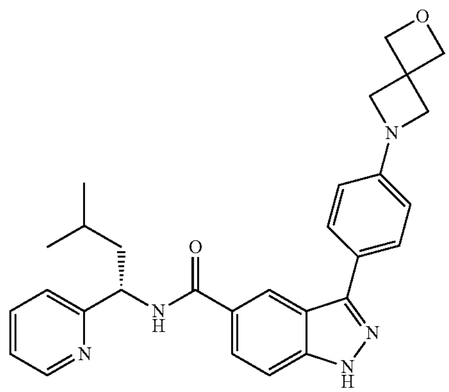 [SMILES: CC(C)C[C@H](NC(=O)c1ccc2[nH]nc(-c3ccc(N4CC5(COC5)C4)cc3)c2c1)c1ccccn1] | [$C_{29}H_{31}N_5O_2$ + H]+ 482.3 | 482.4 | 145 mg (45%); yellow solid; p-toluene sulfonate salt |
| Starting materials: (S)-3-iodo-N-(3-methyl-1-(pyridin-2-yl)butyl)-1H-indazole-5-carboxamide (220 mg, 0.50 mmol), 6-(4-(4,4,5,5-tetramethyl-1,3,2-dioxaborolan-2-yl)phenyl)-2-oxa-6-azaspiro[3.3]heptane (150 mg, 0.50 mmol) ¹H NMR (400 MHz, CDCl₃) δ ppm 9.17 (br d, J = 6.6 Hz, 1H), 8.74 (d, J = 5.8 Hz, 1H), 8.55 (s, 1H), 8.28 (t, J = 8.0 Hz, 1H), 7.97 (d, J = 8.0 Hz, 1H), 7.89 (d, J = 8.7 Hz, 1H), 7.76-7.72 (m, 4H), 7.68 (t, J = 6.9 Hz, 1H), 7.24 (d, J = 8.7 Hz, 1H), 7.06 (d, J = 7.9 Hz, 2H), 6.44 (d, J = 8.6 Hz, 2H), 5.51-5.45 (m, 1H), 4.83 (s, 4H), 3.40 (s, 4H), 2.46-2.39 (m, 1H), 1.88-1.76 (m, 2H), 1.00 (d, J = 6.3 Hz, 3H), 0.97 (d, J = 6.2 Hz, 3H) | | | |
| A28: (S)-N-(1-(2-Chlorophenyl)-2-methylpropyl)-3-(4-(6-methyl-2,6-diaza-spiro[3.3]heptan-2-yl)phenyl)-1H-indazole-5-carboxamide | 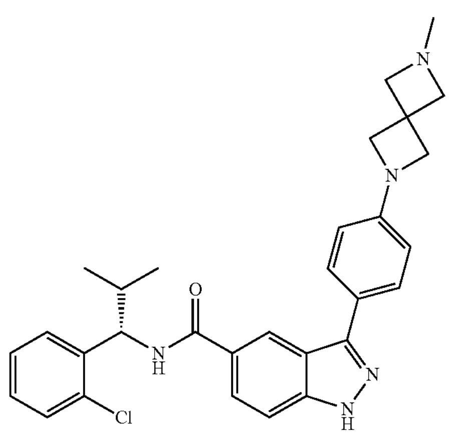 [SMILES: CC(C)[C@H](NC(=O)c1ccc2[nH]nc(-c3ccc(N4CC5(CN(C)C5)C4)cc3)c2c1)c1ccccc1Cl] | [$C_{30}H_{32}ClN_5O$ + H]+ 514.2 | 514.2 | 60 mg (60%); yellow solid; TFA salt |

| Example/ IUPAC name | Structure | MS calculated | MS ESI [M + H]⁺ | Yield; Appearance; Salt form |
|---|---|---|---|---|
| | Starting materials: (S)-N-(1-(2-chlorophenyl)-2-methylpropyl)-3-iodo-1H-indazole-5-carboxamide (72 mg, 0.16 mmol), 2-methyl-6-(4-(4,4,5,5-tetramethyl-1,3,2-dioxaborolan-2-yl)phenyl)-2,6-diazaspiro[3.3]heptanes (50 mg, 0.16 mmol) ¹H NMR (400 MHz, CD₃OD) δ ppm 8.49 (s, 1H), 7.87 (d, J = 8.5 Hz, 1H), 7.81 (d, J = 8.5 Hz, 2H), 7.55 (t, J = 7.3 Hz, 2H), 7.39 (d, J = 7.5 Hz, 1H), 7.29 (t, J = 7.0 Hz, 1H), 7.22 (t, J = 7.8 Hz, 1H), 6.63 (d, J = 8.5 Hz, 2H), 5.32-5.41 (m, 1H), 4.55 (d, J = 11.3 Hz, 2H), 4.26 (d, J = 11.3 Hz, 2H), 4.14 (s, 2H), 4.08 (s, 2H), 2.95 (s, 3H), 2.21-2.33 (m, 1H), 1.16 (d, J = 6.5 Hz, 3H) 0.87 (d, J = 6.8 Hz, 3H) | | | |
| A29: (S)-N-(Cyclopropyl(phenyl)methyl)-3-(4-(6-methyl-2,6-diazaspiro[3.3]heptan-2-yl)phenyl)-1H-indazole-5-carboxamide | 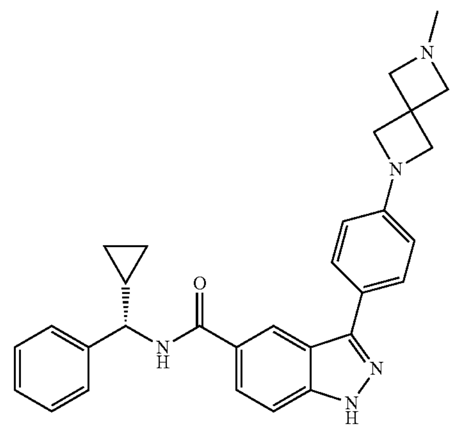 [SMILES: CN1CC2(C1)CN(c1ccc(-c3n[nH]c4ccc(C(=O)N[C@H](c5ccccc5)C5CC5)cc34)cc1)C2] | [C₃₀H₃₁N₅O + H]⁺ 478.2 | 478.2 | 52 mg (55%); yellow solid; TFA salt |
| | Starting materials: (S)-N-(cyclopropyl(phenyl)methyl)-3-iodo-1H-indazole-5-carboxamide (66 mg, 0.16 mmol), 2-methyl-6-(4-(4,4,5,5-tetramethyl-1,3,2-dioxaborolan-2-yl)phenyl)-2,6-diazaspiro[3.3]heptanes (50 mg, 0.16 mmol) ¹H NMR (400 MHz, CD₃OD) δ ppm 8.56 (s, 1H), 7.94 (d, J = 8.5 Hz, 1H), 7.85 (d, J = 8.5 Hz, 2H), 7.58 (d, J = 9.0 Hz, 1H), 7.49 (d, J = 7.3 Hz, 2H), 7.34 (t, J = 7.5 Hz, 2H), 7.24 (t, J = 7.5 Hz, 1H), 6.66 (d, J = 8.5 Hz, 2H), 4.55 (d, J = 11.8 Hz, 2H), 4.48 (d, J = 9.8 Hz, 1H), 4.28 (d, J = 12.0 Hz, 2H), 4.16 (s, 2H), 4.10 (s, 2H), 2.96 (s, 3H), 1.34-1.46 (m, 1H), 0.67 (d, J = 8.0 Hz, 2H), 0.42-0.54 (m, 2H) | | | |
| A30: (S)-N-(1-(2-Chlorophenyl)-2-methylpropyl)-3-(4-(6-(oxetan-3-yl)-2,6-diazaspiro[3.3]heptan-2-yl)phenyl)-1H-indazole-5-carboxamide | 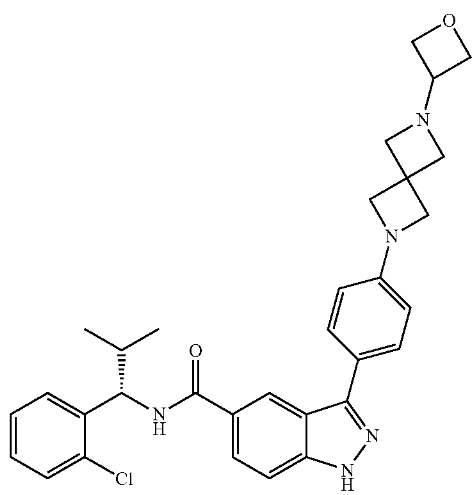 [SMILES: CC(C)[C@H](NC(=O)c1ccc2[nH]nc(-c3ccc(N4CC5(C4)CN(C4COC4)C5)cc3)c2c1)c1ccccc1Cl] | [C₃₂H₃₄ClN₅O₂ + H]⁺ 556.2 | 556.6 | 82 mg (56%); yellow solid; TFA salt |
| | Starting materials: (S)-N-(1-(2-chlorophenyl)-2-methylpropyl)-3-iodo-1H-indazole-5-carboxamide (100 mg, 0.22 mmol), 2-(oxetan-3-yl)-6-(4-(4,4,5,5-tetramethyl-1,3,2-dioxaborolan-2-yl)phenyl)-2,6-diazaspiro[3.3]heptanes (79 mg, 0.22 mmol) ¹H NMR (400 MHz, CD₃OD) δ ppm 8.48 (s, 1H), 7.85 (d, J = 8.8 Hz, 1H), 7.79 (d, J = 8.5 Hz, 2H), 7.54 (d, J = 8.8 Hz, 2H), 7.37 (d, J = 8.0 Hz, 1H), 7.27 (t, J = 7.5 Hz, 1H), 7.20 (t, J = 6.3 Hz, 1H), 6.59 (d, J = 8.5 Hz, 2H), 5.37 (d, J = 9.8 Hz, 1H), 4.88-4.96 (m, 2H), 4.51-4.60 (m, 3H), 4.46 (br. s., 4H), 4.09 (s, 4H), 2.21-2.33 (m, 1H), 1.15 (d, J = 6.5 Hz, 3H), 0.86 (d, J = 6.8 Hz, 3H) | | | |

| Example/ IUPAC name | Structure | MS calculated | MS ESI [M + H]+ | Yield; Appearance; Salt form |
|---|---|---|---|---|
| A31: (S)-N-(Cyclopentyl(pyridin-2-yl)methyl)-3-(4-(6-(oxetan-3-yl)-2,6-diazaspiro[3.3]heptan-2-yl)phenyl)-1H-indazole-5-carboxamide | 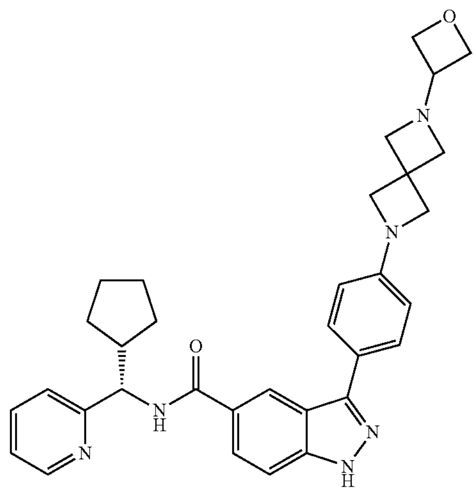 [SMILES: O=C(N[C@H](c1ccccn1)C1CCCC1)c1ccc2[nH]nc(-c3ccc(N4CC5(C4)CN(C4COC4)C5)cc3)c2c1] | $[C_{33}H_{36}N_6O_2 + H]^+$ 549.3 | 549.3 | 73 mg (43%); yellow solid; 2 TFA salt |

Starting materials: (S)-N-(cyclopentyl(pyridin-2-yl)methyl)-3-iodo-1H-indazole-5-carboxamide (100 mg, 0.22 mmol), 2-(oxetan-3-yl)-6-(4-(4,4,5,5-tetramethyl-1,3,2-dioxaborolan-2-yl)phenyl)-2,6-diazaspiro[3.3]heptanes (79 mg, 0.22 mmol)

$^1$H NMR (400 MHz, CD$_3$OD) δ ppm 8.78 (d, J = 5.5 Hz, 1H), 8.58 (s, 1H), 8.53 (t, J = 7.8 Hz, 1H), 8.10 (d, J = 8.0 Hz, 1H), 7.88-7.95 (m, 2H), 7.84 (d, J = 8.5 Hz, 2H), 7.58 (d, J = 8.8 Hz, 1H), 6.65 (d, J = 8.5 Hz, 2H), 5.03 (d, J = 10.8 Hz, 1H), 4.93 (s, 2H), 4.52-4.61 (m, 3H), 4.49 (br. s., 4H), 4.14 (s, 4H), 2.55-2.68 (m, 1H), 2.17 (br. s., 1H), 1.50-1.83 (m, 5H), 1.41 (br. s., 1H), 1.24 (br. s., 1H)

| Example/ IUPAC name | Structure | MS calculated | MS ESI [M + H]+ | Yield; Appearance; Salt form |
|---|---|---|---|---|
| A32: (S)-N-(1-(2-Chlorophenyl)-2-methylpropyl)-3-(4-(6-hydroxy-2-azaspiro[3.3]heptan-2-yl)phenyl)-1H-indazole-5-carboxamide | 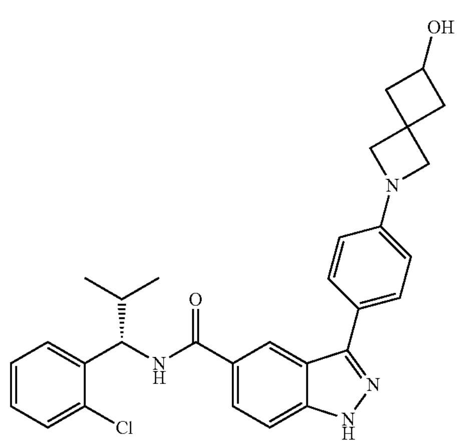 [SMILES: CC(C)[C@H](NC(=O)c1ccc2[nH]nc(-c3ccc(N4CC5(CC(O)C5)C4)cc3)c2c1)c1ccccc1Cl] | $[C_{30}H_{31}ClN_4O_2 + H]^+$ 515.2 | 515.5 | 30 mg (22%); yellow solid; TFA salt |

Starting materials: (S)-N-(1-(2-chlorophenyl)-2-methylpropyl)-3-iodo-1H-indazole-5-carboxamide (100 mg, 0.22 mmol), 2-(4-(4,4,5,5-tetramethyl-1,3,2-dioxaborolan-2-yl)phenyl)-2-azaspiro[3.3]heptan-6-ol (69 mh, 0.22 mmol)

$^1$H NMR (400 MHz, CD$_3$OD) δ ppm 8.52 (s, 1H), 7.85-7.89 (m, 1H), 7.83 (d, J = 8.5 Hz, 2H), 7.51-7.59 (m, 2H), 7.39 (d, J = 7.8 Hz, 1H), 7.31 (t, J = 8.5 Hz, 1H), 7.23 (t, J = 7.8 Hz, 1H), 6.69 (d, J = 8.8 Hz, 2H), 5.33-5.40 (m, 1H), 4.14-4.23 (m, 1H), 3.96 (s, 2H), 3.92 (s, 2H), 2.55-2.65 (m, 2H), 2.23-2.33 (m, 1H), 2.11-2.20 (m, 2H), 1.16 (d, J = 6.8 Hz, 3H), 0.87 (d, J = 6.8 Hz, 3H)

| Example/ IUPAC name | Structure | MS calculated | MS ESI [M + H]+ | Yield; Appearance; Salt form |
|---|---|---|---|---|
| A33: (S)-N-(Cyclopentyl(pyridin-2-yl)methyl)-3-(4-(6-hydroxy-2-aza-spiro[3.3]heptan-2-yl)phenyl)-1H-indazole-5-carboxamide | 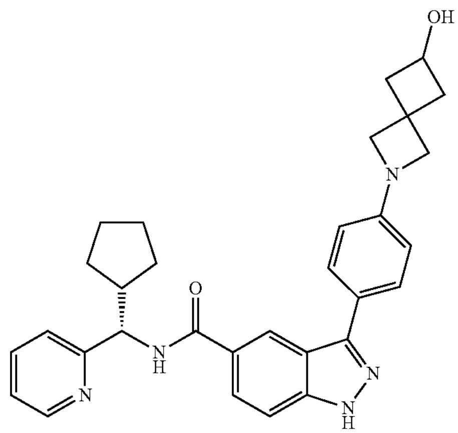 [SMILES: O=C(N[C@H](c1ccccn1)C1CCCC1)c1ccc2[nH]nc(-c3ccc(N4CC5(CC(O)C5)C4)cc3)c2c1] | [C₃₁H₃₃N₅O₂ + H]+ 508.3 | 508.3 | 40 mg (25%); yellow solid; 2 TFA salt |

Starting materials: (S)-N-(cyclopentyl(pyridin-2-yl)methyl)-3-iodo-1H-indazole-5-carboxamide (100 mg, 0.22 mmol), 2-(4-(4,4,5,5-tetramethyl-1,3,2-dioxaborolan-2-yl)phenyl)-2-azaspiro[3.3]heptan-6-ol (69 mh, 0.22 mmol)

$^1$H NMR (400 MHz, CD₃OD) δ ppm 8.77-8.84 (m, 1H), 8.58-8.65 (m, 2H), 8.15 (d, J = 8.3 Hz, 1H), 8.04 (d, J = 9.0 Hz, 2H), 7.97-8.02 (m, 1H), 7.93 (d, J = 8.8 Hz, 1H), 7.64 (d, J = 9.8 Hz, 1H), 7.22 (d, J = 8.8 Hz, 2H), 5.02 (d, J = 11.0 Hz, 1H), 4.35 (s, 2H), 4.32 (s, 2H), 4.17-4.27 (m, 1H), 2.65-2.73 (m, 2H), 2.56-2.65 (m, 1H), 2.16-2.28 (m, 3H), 1.68-1.85 (m, 3H), 1.53-1.69 (m, 2H), 1.40-1.50 (m, 1H), 1.18-1.30 (m, 1H)

| Example/ IUPAC name | Structure | MS calculated | MS ESI [M + H]+ | Yield; Appearance; Salt form |
|---|---|---|---|---|
| A34: (S)-3-(4-(6-Oxa-1-aza-spiro[3.3]heptan-1-yl)phenyl)-N-(cyclopentyl(pyridin-2-yl)methyl)-1H-indazole-5-carboxamide | | [C₃₀H₃₁N₅O₂ + H]+ 494.3 | 494.3 | 68 mg (26%); yellow solid; p-toluene sulfonate salt |

Starting materials: (S)-N-(cyclopentyl(pyridin-2-yl)methyl)-3-iodo-1H-indazole-5-carboxamide (173 mg, 0.39 mmol), 1-(4-(4,4,5,5-Tetramethyl-1,3,2-dioxaborolan-2-yl)phenyl)-6-oxa-1-azaspiro[3.3]heptane (130 mg, 0.39 mmol)

$^1$H NMR (400 MHz, CDCl₃) δ ppm 9.34 (d, J = 6.8 Hz, 1H), 8.79 (d, J = 5.0 Hz, 1H), 8.58 (s, 1H), 8.31 (dt, J = 7.8, 1.0 Hz, 1H), 8.00 (d, J = 7.8 Hz, 1H), 7.90 (dd, J = 9.0, 1.0 Hz, 1H), 7.80 (d, J = 8.5 Hz, 2H), 7.74-7.70 (m, 3H), 7.27 (s, 1H), 7.03 (d, J = 8.3 Hz, 2H), 6.77 (d, J = 8.5 Hz, 2H), 5.28 (dd, J = 7.8, 2.3 Hz, 2H), 5.05 (dd, J = 11.4, 6.9 Hz, 1H), 4.74 (d, J = 8.0 Hz, 2H), 3.68 (t, J = 7.0 Hz, 2H), 2.87-3.04 (m, 1H), 2.54 (t, J = 6.9 Hz, 2H), 2.27-2.25 (m, 4H), 1.45-1.79 (m, 5H), 1.29-1.42 (m, 1H), 1.03-1.17 (m, 1H)

| Example/ IUPAC name | Structure | MS calculated | MS ESI [M + H]+ | Yield; Appearance; Salt form |
|---|---|---|---|---|
| A35: (S)-3-(4-(6-Oxa-1-aza-spiro[3.3]heptan-1-yl)phenyl)-N-(3-methyl-1-(pyridin-2-yl)butyl)-1H-indazole-5-carboxamide | 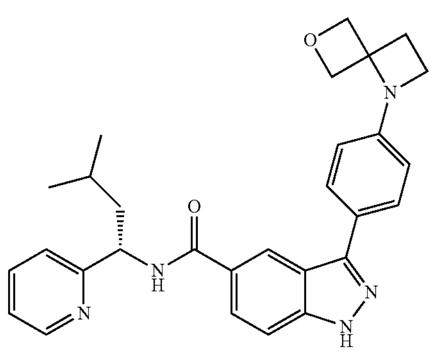 [SMILES: CC(C)C[C@H](NC(=O)c1ccc2[nH]nc(-c3ccc(N4CCC45COC5)cc3)c2c1)c1ccccn1] | [C₂₉H₃₁N₅O₂ + H]+ 482.3 | 482.4 | 89 mg (39%); yellow solid; p-toluene sulfonate salt |

Starting materials: (S)-3-iodo-N-(3-methyl-1-(pyridin-2-yl)butyl)-1H-indazole-5-carboxamide (153 mg, 0.35 mmol), 1-(4-(4,4,5,5-Tetramethyl-1,3,2-dioxaborolan-2-yl)phenyl)-6-oxa-1-azaspiro[3.3]heptane (130 mg, 0.39 mmol)

| Example/ IUPAC name | Structure | MS calculated | MS ESI [M + H]+ | Yield; Appearance; Salt form |
|---|---|---|---|---|
| | <sup>1</sup>H NMR (400 MHz, CDCl<sub>3</sub>) δ ppm 9.16 (d, J = 6.5 Hz, 1H), 8.76 (d, J = 5.8 Hz, 1H), 8.43 (s, 1H), 8.28 (t, J = 7.4 Hz, 1H), 7.97 (d, J = 8.0 Hz, 1H), 7.85 (d, J = 7.8 Hz, 1H), 7.78 (d, J = 8.0 Hz, 2H), 7.61-7.72 (m, 3H), 7.17 (d, J = 9.0 Hz, 1H), 7.09 (d, J = 8.0 Hz, 2H), 6.71 (d, J = 8.5 Hz, 2H), 5.41-5.57 (m, 1H), 5.16-5.34 (m, 2H), 4.73 (d, J = 7.8 Hz, 2H), 3.65 (t, J = 6.5 Hz, 2H), 2.52 (t, J = 6.8 Hz, 2H), 2.42-2.49 (m, 1H), 2.30 (s, 3H), 1.72-1.92 (m, 2H), 0.99 (dd, J = 17.9, 5.9 Hz, 6H) | | | |
| A36: (R)-3-(4-(1-Oxa-6-aza-spiro[3.3]heptan-6-yl)phenyl)-N-(cyclo-propyl(pyridin-2-yl)methyl)-1H-indazole-5-carboxamide | 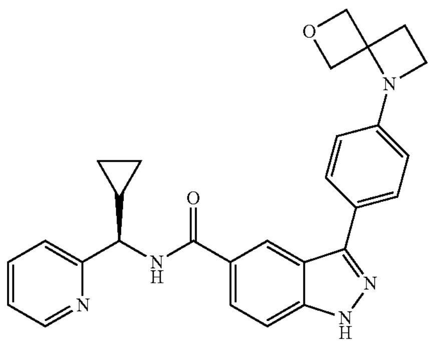 [SMILES: O=C(N[C@@H](c1ccccn1)C1CC1)c1ccc2[nH]nc(-c3ccc(N4CCC45COC5)cc3)c2c1] | [C$_{28}$H$_{27}$N$_5$O$_2$ + H]$^+$ 466.2 | 466.3 | 38 mg (50%); yellow solid; p-toluene sulfonate salt |
| | Starting materials: (R)-N-(cyclopropyl(pyridin-2-yl)methyl)-3-iodo-1H-indazole-5-carboxamide (148 mg, 0.35 mmol), 1-(4-(4,4,5,5-Tetramethyl-1,3,2-dioxaborolan-2-yl)phenyl)-6-oxa-1-azaspiro[3.3]heptane (130 mg, 0.39 mmol)<br><sup>1</sup>H NMR (400 MHz, CDCl<sub>3</sub>) δ ppm 9.48 (d, J = 6.8 Hz, 1H), 8.81 (d, J = 5.5 Hz, 1H), 8.53 (s, 1H), 8.39 (t, J = 7.8 Hz, 1H), 8.11 (d, J = 7.8 Hz, 1H), 7.95 (d, J = 9.0 Hz, 1H), 7.67-7.83 (m, 5H), 7.22 (d, J = 9.0 Hz, 1H), 7.10 (d, J = 8.0 Hz, 2H), 6.76 (d, J = 8.5 Hz, 2H), 5.28 (dd, J = 7.7, 3.1 Hz, 2H), 4.75 (d, J = 7.8 Hz, 2H), 4.60 (dd, J = 10.3, 7.0 Hz, 1H), 3.70 (t, J = 6.9 Hz, 2H), 2.56 (t, J = 6.9 Hz, 2H), 2.32 (s, 3H), 1.94-2.08 (m, 1H), 0.87-0.97 (m, 1H), 0.75-0.84 (m, 1H), 0.64-0.73 (m, 1H), 0.45-0.55 (m, 1H) | | | |
| A37: (R)-3-(4-(6-oxa-1-aza-spiro[3.3]heptan-1-yl)phenyl)-N-(cyclo-pentyl(pyrimidin-2-yl)methyl)-1H-indazole-5-carboxamide | 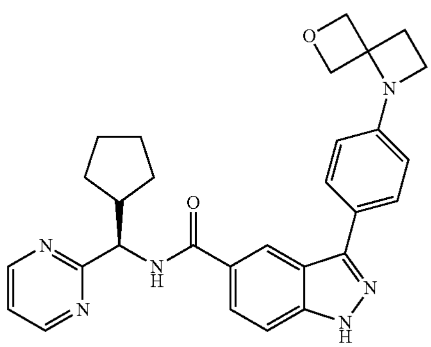 [SMILES: O=C(N[C@@H](c1ncccn1)C1CCCC1)c1ccc2[nH]nc(-c3ccc(N4CCC45COC5)cc3)c2c1] | [C$_{29}$H$_{30}$N$_6$O$_2$ + H]$^+$ 495.2 | 495.4 | 43 mg (54%); light yellow solid; free base |
| | Starting materials: (R)-N-(cyclopentyl(pyrimidin-2-yl)methyl)-3-iodo-1H-indazole-5-carboxamide (71 mg, 0.16 mmol), 1-(4-(4,4,5,5-Tetramethyl-1,3,2-dioxaborolan-2-yl)phenyl)-6-oxa-1-azaspiro[3.3]heptane (53 mg, 0.16 mmol)<br><sup>1</sup>H NMR (400 MHz, CDCl<sub>3</sub>) δ ppm 11.20 (br. s., 1H), 8.74 (d, J = 5.0 Hz, 2H), 8.58 (s, 1H), 7.90 (d, J = 8.5 Hz, 2H), 7.85 (dd, J = 8.7, 1.4 Hz, 1H), 7.50 (d, J = 8.5 Hz, 1H), 7.41 (d, J = 8.8 Hz, 1H), 7.21 (t, J = 4.9 Hz, 1H), 6.89 (d, J = 8.5 Hz, 2H), 5.49 (t, J = 8.0 Hz, 1H), 5.35 (d, J = 8.0 Hz, 2H), 4.81 (d, J = 8.0 Hz, 2H), 3.77 (t, J = 6.9 Hz, 2H), 2.48-2.63 (m, 3H), 1.46-1.75 (m, 8H) | | | |

Example B

TTK Inhibition Assay

Active TTK was purchased from Invitrogen as an amino terminal GST fusion of full length human TTK. Amino terminal 6 histidine, sumo tagged human TTK (residues 1-275) was expressed in *E. coli*, and purified to >95% homogeneity by Ni$^{2+}$ agarose, gel filtration, and ion exchange chromatography.

TTK activity was measured using an indirect ELISA detection system. GST-TTK (0.68 nM) was incubated in the presence of 16 μM ATP (Sigma cat#A7699), 50 mM Hepes pH 7.2, 1 mM EGTA, 10 mM MgCl$_2$, and 0.1% Pluronic in a 96 well microtitre plate pre-coated with amino terminal 6 histidine, sumo tagged TTK (amino acid residues 1-275). The reaction was allowed to proceed for 30 minutes, followed by 5 washes of the plate with Wash Buffer (phosphate buffered saline supplemented with 0.2% Tween 20), and incubation for 30 minutes with a 1:3000 dilution of primary antibody (Cell Signaling cat#9381). The plate was washed 5 times with Wash Buffer, incubated for 30 minutes in the presence of secondary antibody coupled to horse radish peroxidase (Bio-Rad cat#1721019, 1:3000 concentration), washed an additional 5 times with Wash Buffer, and incubated in the presence of TMB substrate (Sigma cat#T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 µM) or at a variable inhibitor concentration (typically 0.5 µM to 0.001 µM in a 10 point dose response titration). Compounds were pre-incubated in the presence of enzyme for 5 minutes prior to addition of ATP and the activity remaining quantified using the above described activity assay. The % Inhibition of a compound was determined using the following formula; % Inhibition=100×(1−(experimental value−background value)/(high activity control−background value)). The $IC_{50}$ value was determined using a non-linear 4 point logistic curve fit (XLfit4, IDBS) with the formula; (A+(B/(1+((x/C)^D)))), where A=background value, B=range, C=inflection point, D=curve fit parameter.

Compounds described herein are potent TTK inhibitors with an $IC_{50}$ less than 0.1 µM.

Example C

Cancer Cell Line Data on Exemplary Compounds of the Invention

Breast cancer cells (MDA-MB-231), colon cancer cells (HCT116) and ovarian cancer cells (PA-1) were seeded (1000 to 4000 in 80 µl per well depending on the cell growth rate) into 96 well plates 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 µM. Aliquots (20 µl) from each concentration were overlaid to 80 µl of the pre-seeded cells in the 96 well plates to make final concentrations of 10 nM to 50 µM. The cells were cultured for 5 days before the Sulforhodamine B assay (SRB) was performed to determine the compound's cell growth inhibition activity.

Sulforhodamine B (purchased from Sigma, Oakville, ON, Canada) is a water-soluble dye that binds to the basic amino acids of the cellular proteins. Thus, colorimetric measurement of the bound dye provides an estimate of the total protein mass that is related to the cell number. the cells are fixed in situ by gently aspirating off the culture media and adding 50 µl ice cold 10% Trichloroacetic Acid (TCA) per well and incubate at 4° C. for 30-60 min. The plates are washed with $H_2O$ five times and allowed to air dry for 5 min. Addition of 50 µl 0.4% (w/v) SRB solution in 1% (v/v) acetic acid to each well and incubatation for 30 min at RT completes the staining reaction. Following staining, plates are washed four times with 1% acetic acid to remove unbound dye and then allowed to air dry for 5 min. The stain is solubilized with 100 µl of 10 mM Tris pH 10.5 per well. Absorbance is read at 570 nm.

The percentage (%) of relative growth inhibition was calculated by comparing to DMSO treated only cells (100%). $GI_{50}$'s were determined for compounds with cytotoxic activity. The $GI_{50}$ was calculated using GraphPad PRISM software (GraphPad Software, Inc., San Diego, Calif., USA). $GI_{50}$ (growth inhibition) is the compound concentration that causes 50% inhibition of cell growth.

In Table 1 below, $GI_{50}$ value ranges for several compound examples against breast cancer cell lines (MDA-MB-231), colon cancer cell lines (HCT116) and ovarian cancer cell lines (PA-1) are given. The example compounds demonstrated varying growth inhibition/cell killing activity against cells of breast cancer, colon cancer, and ovarian cancer. The $GI_{50}$ ranges are indicated as "A," "B," and "C," for values less than or equal to 0.1 µM; those greater than 0.1 µM and less than or equal to 0.5 µM; and those greater than 0.5 µM, respectively.

TABLE 1

Cell Growth Inhibition Data

| Example # | Cancer Cell Line $GI_{50}$ Range (µM) | | |
|---|---|---|---|
| | MDA-MB-231 | HCT116 | PA-1 |
| Example A1 | A | A | A |
| Example A2 | A | A | A |
| Example A3 | B | A | A |
| Example A4 | A | A | A |
| Example A5 | A | A | A |
| Example A6 | B | A | A |
| Example A7 | A | A | A |
| Example A8 | A | A | A |
| Example A9 | C | B | B |
| Example A10 | B | A | A |
| Example A11 | A | A | A |
| Example A12 | A | A | A |
| Example A13 | B | A | A |
| Example A14 | A | A | A |
| Example A15 | B | A | A |
| Example A16 | B | B | B |
| Example A17 | B | B | B |
| Example A18 | A | A | A |
| Example A19 | A | A | A |
| Example A20 | A | A | A |
| Example A21 | A | A | A |
| Example A22 | A | A | A |
| Example A23 | A | A | A |
| Example A24 | A | A | A |
| Example A25 | A | A | A |
| Example A26 | A | A | A |
| Example A27 | A | A | A |
| Example A28 | A | A | A |
| Example A29 | A | A | A |
| Example A30 | A | A | A |
| Example A31 | A | A | A |
| Example A32 | A | A | A |
| Example A33 | A | A | A |
| Example A34 | B | B | B |
| Example A35 | B | B | B |
| Example A36 | C | B | B |
| Example A37 | A | A | A |

Example D

Colon and Ovarian Cancer Tumor-Initiating Cell Data of Exemplary Compounds

Materials and Methods:

Non-tissue or tissue cultured treated T-75 flask and 96-well plates were purchased from VWR. Vitamin B-27 supplement, MEM NEAA (minimum essential medium non essential amino acids), sodium pyruvate, L-glutamine, N2 supplement, penicillin-streptomycin and fungizone/amphotericin B were obtained from Invitrogen. Lipid mixture, heparin and EGF were purchased from Sigma; bFGF from BD Biosciences. Colon tumor initiating cells (TICs) were routinely maintained using non-tissue cultured treated T-75 flasks in DMEM:F12 medium containing 0.2XB-27 supplement, 4 ug/ml heparin, 1XMEM NEAA, 1Xsodium pyruvate, 1 mM glutamine, 10 pg/ul bFGF, 20 pg/ul EGF, 1×N2 supplement, lipid mixture, penicillin-streptomycin and fungizone/amphotericin B. Ovarian TICs were were routinely maintained using tissue cultured treated T-75 flasks in DMEM:F12 medium containing 1XB-27 supplement, 4 ug/ml heparin, 20 pg/ul bFGF, 20 pg/ul EGF and penicillin-streptomycin.

103

Assay Protocol:

Compounds described herein were dissolved in DMSO and further diluted in cell culture medium for GI50 determination. Colon TICs were trypsinized and seeded into non-tissue cultured treated 96-well plates with 4,000 cells/well. After 24 h, compound was added into the cell culture at different concentrations, and the final concentration of DMSO was adjusted to 0.1%. Cells were then cultured at 37° C. for 9 days. Ovarian TICs were trypsinized and seeded into tissue cultured treated 96-well plates with 1,000 cells/well. After 24 h, compound was added into the cell culture at different concentrations, and the final concentration of DMSO was adjusted to 0.1%. Cells were then cultured at 37° C. for 6 days. Cell viability was assessed by Alamar Blue assay: 10 ul of Alamar Blue was added into each well. After 4 hours incubation at 37° C., fluorescence was recorded at excitation 544 and emission 590. $GI_{50}$ (Growth inhibition) was calculated using GraphPad Prism 4.0 software. Cell growth inhibition data for compounds described herein is tabulated below (Table 2). The $GI_{50}$ ranges are indicated as "A," and "B," for values less than or equal to 0.1 µM: those greater than 0.1 µM and less than or equal to 0.5 µM, respectively.

TABLE 2

Colon and Ovarian Tumor-Initiating Cell Growth Inhibition Data

| Example # | Tumor Initiating Cell Line $GI_{50}$ Range (µM) | |
| --- | --- | --- |
| | colon 12 | ovarian 2393A |
| Example A1 | A | A |
| Example A2 | A | A |
| Example A3 | A | B |
| Example A4 | B | A |
| Example A5 | B | A |
| Example A6 | B | B |
| Example A7 | A | A |
| Example A8 | A | A |
| Example A10 | A | B |
| Example A11 | A | A |
| Example A12 | A | A |
| Example A15 | B | B |
| Example A18 | A | B |
| Example A19 | A | B |
| Example A20 | A | A |
| Example A23 | A | A |
| Example A24 | A | A |
| Example A32 | A | A |

While this invention has been particularly shown and described with references to example embodiments thereof, it will be understood by those skilled in the art that various changes in form and details may be made therein without departing from the scope of the invention encompassed by the appended claims.

104

What is claimed is:

1. A compound of formula (I):

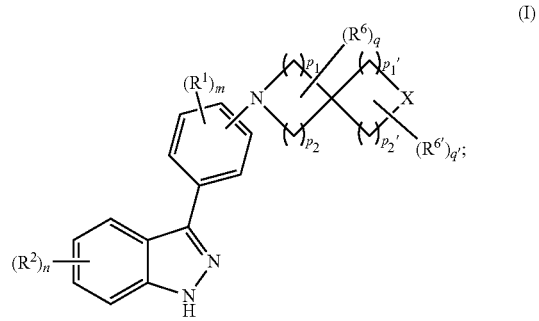

or a pharmaceutically acceptable salt thereof, wherein:

each $R^1$ is independently selected from —H, -halogen, —CN, —NO$_2$, OR$^c$, —NR$^a$R$^b$, —S(O)$_i$R$^c$, —NR$^d$S(O)$_i$R$^c$, —S(O)$_i$NR$^e$R$^f$, —C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, heterocycloalkyl, and alkyl, wherein the heterocycloalkyl or the alkyl is optionally substituted with 1 to 3 substituents independently selected from -halogen, —CN, —NO$_2$, —OR$^c$, —NR$^a$R$^b$, —S(O)$_i$R$^c$, —NR$^d$S(O)$_i$R$^c$, —S(O)$_i$NR$^e$R$^f$, —C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, and —C(=O)R$^c$;

each $R^2$ is independently selected from —(CH$_2$)$_{0-2}$C(=O)NR$^4$(CH$_2$)$_{0-2}$Z—R$^5$, —(CH$_2$)$_{0-2}$NR$^4$C(=O)(CH$_2$)$_{0-2}$Z—R$^5$, and —(CH$_2$)$_{0-2}$NR$^4$(C=O)NR$^4$(CH$_2$)$_{0-2}$Z—R$^5$;

X is —O—, —CR$^8$R$^9$—, —NR$^{11}$—, or —S(O)$_i$—;

$R^4$ is —H or an alkyl group optionally substituted with 1 to 3 substituents independently selected from halogen, hydroxy, and (C$_1$-C$_3$)alkoxy;

$R^5$ is alkyl, cycloalkyl, heterocycloalkyl, aryl, or heteroaryl, each of which is optionally substituted with 1 to 3 groups individually represented by $R^{15}$ or $R^{16}$;

Z is a bond or —CR$^{13}$R$^{14}$—;

$R^6$ and $R^{6'}$ are each independently selected from halogen, hydroxy, (C$_1$-C$_3$)alkyl, (C$_1$-C$_3$)alkoxy, (C$_1$-C$_3$)alkyl-OR$^c$, and —NR$_a$R$_b$; or two instances of R$^6$ or R$^{6'}$ on the same carbon are taken together form =O;

$R^8$ and $R^9$ are each independently selected from —H, —OR$^c$, and (C$_1$-C$_6$)alkyl, wherein the (C$_1$-C$_6$)alkyl group is optionally substituted with 1 to 3 substituents independently selected from halogen, hydroxy, and (C$_1$-C$_3$)alkoxy;

$R^{11}$ is —H, (C$_1$-C$_6$)alkyl, cycloalkyl, cycloalkyl(C$_1$-C$_6$)alkyl, heterocycloalkyl, heterocycloalkyl(C$_1$-C$_6$)alkyl, —C(=O)R$^c$, or —C(=O)OR$^c$, wherein each of the (C$_1$-C$_6$)alkyl, cycloalkyl, cycloalkyl(C$_1$-C$_6$)alkyl, heterocycloalkyl and heterocycloalkyl(C$_1$-C$_6$)alkyl groups is optionally substituted with 1 to 3 substituents independently selected from halogen, hydroxy, (C$_1$-C$_3$)alkoxy, and —C(=O)NR$^e$R$^f$;

R¹³ and R¹⁴ are each independently selected from —H, alkyl, —OR$^c$, —NR$^a$R$^b$, —(C$_1$-C$_3$)alkylene-NR$^a$R$^b$, —(C$_1$-C$_3$)alkylene-OR$^c$, —(C$_1$-C$_3$)alkylene-OH, cycloalkyl, —O-cycloalkyl, and heterocycloalkyl, wherein each of the cycloalkyl or heterocycloalkyl, groups is optionally substituted with 1 to 3 substituents independently selected from (C$_1$-C$_3$)alkyl and (C$_1$-C$_3$)alkoxy, provided that R¹³ and R¹⁴ are not both selected from —OR$^c$ and —NR$^a$R$^b$;

R¹⁵ and R¹⁶ are each independently selected from halogen, —CN, —NO$_2$, =O, —OR$^c$, —NR$^a$R$^b$, —S(O)$_i$R$^c$, —NR$^d$S(O)$_i$R$^c$, —S(O)$_i$NR$^e$R$^f$, C(=O)OR$^c$, —OC(=O)OR$^c$, —C(=S)OR$^c$, —O(C=S)R$^c$, —C(=O)NR$^e$R$^f$, —NR$^d$C(=O)R$^c$, —C(=S)NR$^e$R$^f$, —NR$^d$C(=S)R$^c$, —NR$^d$(C=O)OR$^c$, —O(C=O)NR$^e$R$^f$, —NR$^d$(C=S)OR$^c$, —O(C=S)NR$^e$R$^f$, —NR$^d$(C=O)NR$^e$R$^f$, —NR$^d$(C=S)NR$^e$R$^f$, —C(=S)R$^c$, —C(=O)R$^c$, (C$_1$-C$_6$)alkyl, aryl, aryl(C$_1$-C$_3$)alkyl, heterocycloalkyl and heteroaryl; wherein each (C$_1$-C$_6$)alkyl, aryl, aryl(C$_1$-C$_3$)alkyl, heterocycloalkyl and heteroaryl represented by R¹⁵ is optionally substituted with 1 to 3 substituents independently selected from -halogen, —CN, —OR$^c$, (C$_1$-C$_6$)alkyl, halo(C$_1$-C$_6$)alkyl, (C$_1$-C$_3$)alkoxy, halo(C$_1$-C$_3$)alkoxy, (C$_1$-C$_3$)alkoxy(C$_1$-C$_6$)alkyl, 3 to 8 membered heterocycloalkyl and 3 to 8 membered heteroaryl;

R$^a$ and R$^b$ are each independently selected from —H and (C$_1$-C$_6$)alkyl, optionally substituted with 1 to 3 substituents independently selected from halogen, hydroxy, —NR$^g$R$^h$, and (C$_1$-C$_3$)alkoxy;

R$^c$ is —H or (C$_1$-C$_6$)alkyl, optionally substituted with 1 to 3 substituents independently selected from halogen, —NR$^g$R$^h$, hydroxy, and (C$_1$-C$_3$)alkoxy;

R$^d$ is —H or (C$_1$-C$_6$)alkyl, optionally substituted with 1 to 3 substituents independently selected from halogen, —NR$^g$R$^h$, hydroxy, and (C$_1$-C$_3$)alkoxy;

R$^e$ and R$^f$ are each independently selected from —H and (C$_1$-C$_6$)alkyl optionally substituted with 1 to 3 substituents independently selected from halogen, —NR$^g$R$^h$, hydroxy, and (C$_1$-C$_3$)alkoxy; or R$^e$ and R$^f$, together with the nitrogen to which they are attached, form a 3-8 membered ring optionally substituted with 1 to 3 substituents independently selected from halogen, —NR$^g$R$^h$, —CN, (C$_1$-C$_6$)alkyl, halo(C$_1$-C$_6$)alkyl, (C$_1$-C$_3$)alkoxy, halo(C$_1$-C$_3$)alkoxy, and (C$_1$-C$_3$)alkoxy(C$_1$-C$_6$)alkyl;

R$^g$ and R$^h$ are each independently selected from —H, (C$_1$-C$_6$)alkyl, halo(C$_1$-C$_6$)alkyl, hydroxy(C$_1$-C$_6$)alkyl, and (C$_1$-C$_3$)alkoxy(C$_1$-C$_6$)alkyl;

i is 0, 1, or 2;

n is an integer from 1 to 4;

m is an integer from 1 to 4;

each of p$_1$, p$_2$, p$_1$', and p$_2$', independently, is 0, 1, 2, 3, or 4, provided that p$_1$+p$_2$ is greater than 1, and p$_1$'+p$_2$' is greater than 1;

q is 0, 1, or 2; and q' is 0, 1, or 2.

2. The compound of claim 1, wherein R⁵ is cycloalkyl, heterocycloalkyl, aryl, or heteroaryl, each of which is optionally substituted with 1 to 3 groups individually represented by R¹⁵ or R¹⁶.

3. The compound of claim 2, wherein the group represented by

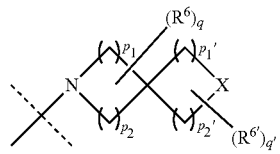

is meta or para to the indazole ring of formula (I).

4. The compound of claim 3, wherein the compound is represented by formula (I-A1):

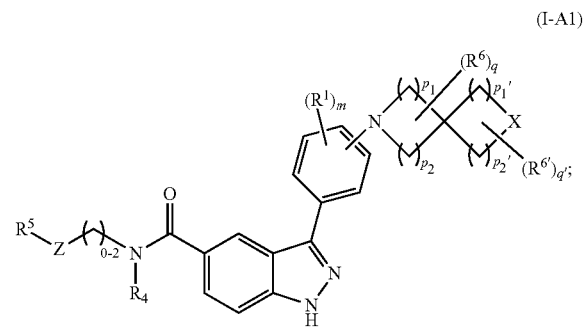

(I-A1)

or a pharmaceutically acceptable salt thereof.

5. The compound of claim 4, wherein the compound is represented by formula (I-B1):

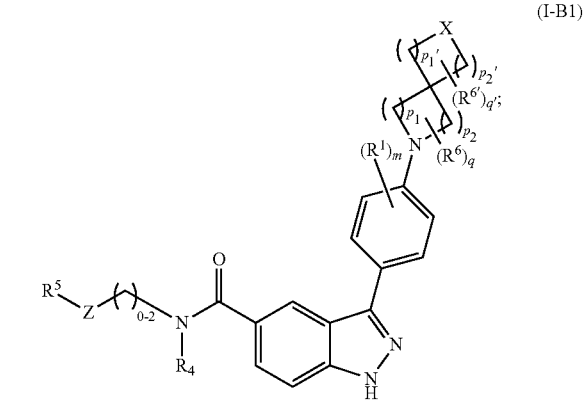

(I-B1)

or a pharmaceutically acceptable salt thereof.

6. The compound of claim 5, wherein the compound is represented by formula (I-C1):

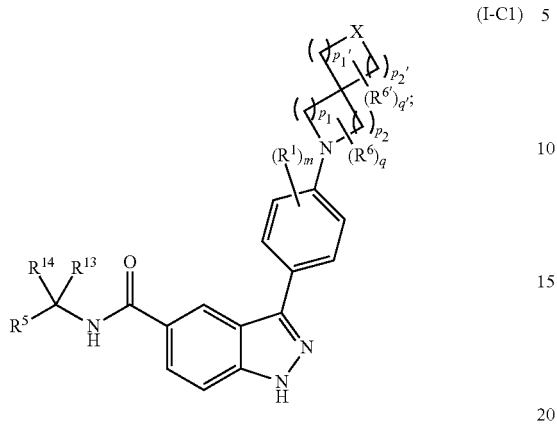

(I-C1)

or a pharmaceutically acceptable salt thereof.

7. The compound of claim 6, wherein the compound is represented by formula (I-D1):

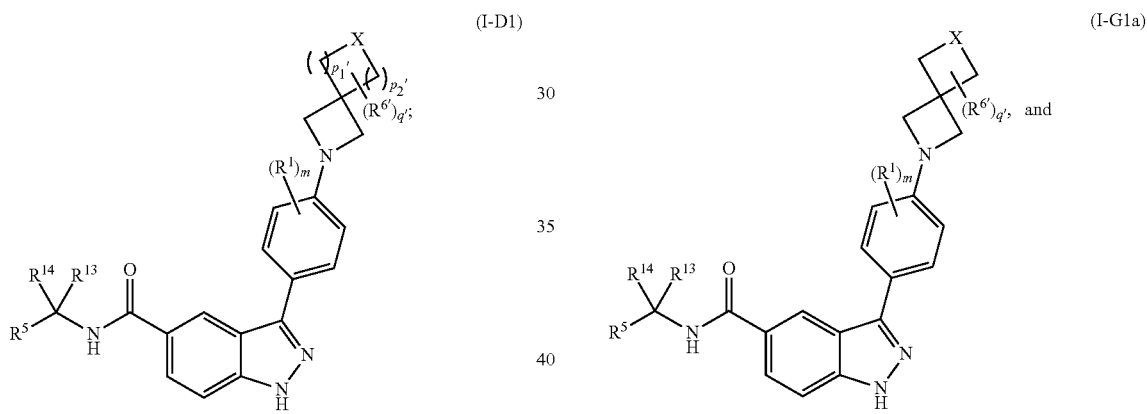

(I-D1)

or a pharmaceutically acceptable salt thereof.

8. The compound of claim 6, wherein the compound is represented by formula (I-E1):

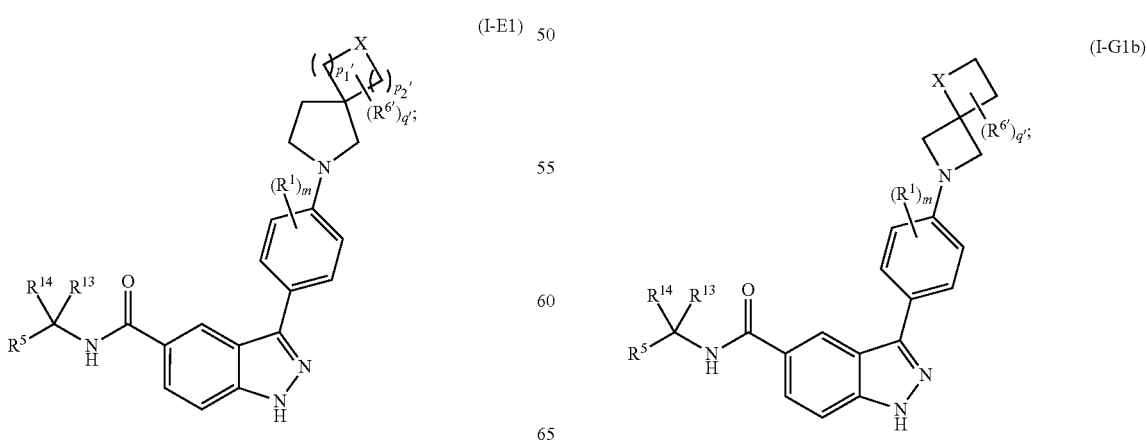

(I-E1)

or a pharmaceutically acceptable salt thereof.

9. The compound of claim 6, wherein the compound is represented by formula (I-F1):

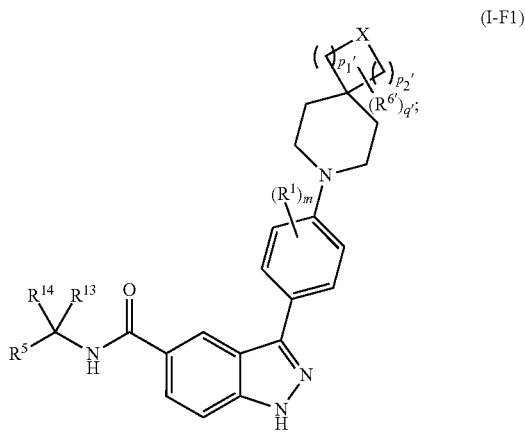

(I-F1)

or a pharmaceutically acceptable salt thereof.

10. The compound of claim 7, wherein the compound is represented by formula (I-G1a) or formula (I-G1b):

(I-G1a)

and (I-G1b)

or a pharmaceutically acceptable salt thereof.

11. The compound of claim 10, wherein the compound is represented by formula (I-H1a):

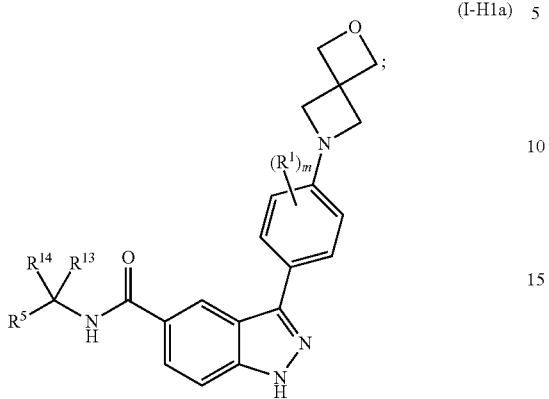

(I-H1a)

or a pharmaceutically acceptable salt thereof.

12. The compound of 7, wherein the compound is represented by formula (I-J1):

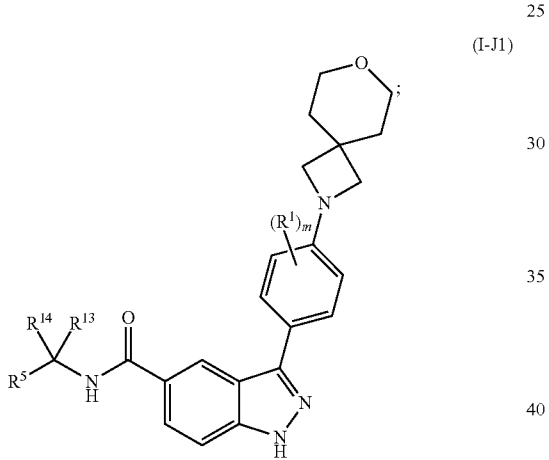

(I-J1)

or a pharmaceutically acceptable salt thereof.

13. The compound of claim 10, wherein
X is —O—, —CR$^8$R$^9$—, or —NR$^{11}$—;
R$^4$ is —H;
R$^6$ and R$^{6'}$ are each independently (C$_1$-C$_3$)alkyl;
R$^8$ and R$^9$ are each independently selected from —H, —OR$^c$, and (C$_1$-C$_6$)alkyl, wherein the (C$_1$-C$_6$)alkyl group is optionally substituted with a substituent selected from halogen, hydroxy and (C$_1$-C$_3$)alkoxy;
R$^{11}$ is —H, (C$_1$-C$_6$)alkyl, heterocycloalkyl, or —C(=O)R$^c$, wherein the (C$_1$-C$_6$)alkyl is optionally substituted with a substituent selected from halogen, hydroxy, (C$_1$-C$_3$)alkoxy and —C(=O)NR$^e$R$^f$;
R$^{13}$ and R$^{14}$ are each independently selected from —H, alkyl, —OR$^c$, —(C$_1$-C$_3$)alkylene-OR$^c$, —(C$_1$-C$_3$)alkylene-OH, (C$_3$-C$_8$)cycloalkyl, —O—(C$_3$-C$_8$)cycloalkyl and 3 to 8 membered heterocycloalkyl, provided that R$^{13}$ and R$^{14}$ are not both —OR$^c$, wherein each of the cycloalkyl or heterocycloalkyl groups is optionally substituted with a (C$_1$-C$_3$)alkyl;
n is an integer from 1 to 2;
m is an integer from 1 to 2; and
each of p$_1$, p$_2$, p$_1'$, and p$_2'$, independently, is 0, 1, or 2, provided that p$_1$+p$_2$ is greater than 1, and p$_1'$+p$_2'$ is greater than 1.

14. The compound of claim 13, wherein
each R$^1$ is independently selected from —H, -halogen, —CN, —NO$_2$, OR$^c$, —NR$^a$R$^b$, —S(O)$_i$R$^c$, —C(=O)OR$^c$, —OC(=O)OR$^c$, —C(=O)NR$^e$R$^f$, —NR$^d$C(=O)R$^c$, —C(=O)R$^c$ or alkyl, wherein the alkyl is optionally substituted with a substituent selected from -halogen, —OR$^c$, —NR$^a$R$^b$, and —S(O)$_i$R$^c$;
R$^5$ is (a) cyclopropyl, cyclobutyl, cyclopentyl, cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl or thienyl, each of which is optionally substituted with 1 to 3 groups represented by R$^{15}$ or (b) bicyclooctanyl, decahydronaphthyl, octahydroindenyl, dihydronaphthalenyl, tetrahydronaphthalenyl, dihydroindolyl, dihydroisoindolyl, dihydrobenzimidazolyl, dihydrobenzothienyl, dihydrobenzofuranyl, dihydroisobenzofuranyl, dihydrobenzotriazolyl, dihydrobenzothiazolyl, dihydrobenzoxazolyl, dihydrobenzisoxazolyl, dihydroquinolinyl, tetrahydroquinolinyl, dihydroisoquinolinyl, tetrahydroisoquinolinyl, dihydroindazolyl, dihydroacridinyl, tetrahydroacridinyl, chromanyl, isochromanyl, chromenyl, isochromenyl, naphthyl, anthracenyl, fluorenyl, indanyl, indenyl, carbazolyl, benzimidazolyl, benzothienyl, benzofuranyl, isobenzofuranyl, indolyl, isoindolyl, benzotriazolyl, benzothiazolyl, benzoxazolyl, benzisoxazolyl, quinolinyl, isoquinolinyl, indazolyl or acridinyl, each of which is optionally substituted with 1 to 3 groups represented by R$^{16}$;
R$^{13}$ is H and R$^{14}$ is —H, (C$_1$-C$_6$)alkyl, OR$^c$, —(C$_1$-C$_3$)alkylene-OR$^c$, —(C$_1$-C$_3$)alkylene-OH, a cycloalkyl selected from cyclopropyl, cyclobutyl, cyclopentyl and cyclohexyl, a —O-cycloalkyl selected from —O-cyclopropyl, —O-cyclobutyl, and —O-cyclopentyl, —O-cyclohexyl, or a heterocycloalkyl selected from morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl and tetrahydrothiopyranyl, provided that R$^{13}$ and R$^{14}$ are not both —OR$^c$, wherein each of the —O-cycloalkyl, cycloalkyl or heterocycloalkyl groups is optionally substituted with a (C$_1$-C$_3$)alkyl; and R$^c$ is —H, or (C$_1$-C$_6$) alkyl;
each R$^{15}$ is independently selected from halogen, —CN, —NO$_2$, =O, —OR$^c$, —NR$^a$R$^b$, —C(=O)OR$^c$, —OC(=O)OR$^c$, —C(=O)NR$^e$R$^f$, —NR$^d$C(=O)R$^c$, —NR$^d$(C=O)OR$^c$, —O(C=O)NR$^e$R$^f$, —NR$^d$(C=O)NR$^e$R$^f$, —C(=O)R$^c$, (C$_1$-C$_6$)alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, phenyl, benzyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; wherein the $(C_1$-$C_6)$alkyl represented by $R^{15}$ is optionally substituted with a substituent selected from -halogen, —$OR^c$, $(C_1$-$C_6)$alkyl, $(C_1$-$C_3)$alkoxy, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl; and each $R^{16}$ is independently selected from halogen, —$OR^c$, —$NR^aR^b$, —$C(=O)OR^c$, —$C(=O)NR^eR^f$, —$NR^dC(=O)R^c$, —$C(=O)R^c$, $(C_1$-$C_6)$alkyl, phenyl, phenyl $(C_1$-$C_3)$alkyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl, tetrahydrothiopyranyl, furanyl, imidazolyl, oxazolyl, isoxazolyl, oxadiazolyl, pyrazolyl, pyrrolyl, pyridyl, pyrimidinyl, pyridazinyl, thiazolyl, isothiazolyl, triazolyl, tetrazolyl, and thienyl.

15. The compound of claim 14, wherein:
$R^1$ is selected from —H, -halogen, —$OCH_3$, —$N(CH_3)_2$, —$S(O)_2CH_3$, or methyl.
$R^5$ is cyclopentyl, cyclohexyl, morpholinyl, pyrrolidinyl, piperidinyl, dihydropyridinyl, tetrahydropyridinyl, dihydropyrimidinyl, tetrahydropyrimidinyl, phenyl, furanyl, imidazolyl, pyrrolyl, pyridyl, pyrimidinyl, thiazoyl, or thienyl, each of which is optionally substituted with 1 to 3 groups represented by $R^{15}$ or (b) chromanyl, chromenyl, dihydroindolyl, dihydroisoindolyl, dihydrobenzothienyl, dihydrobenzofuranyl, dihydroisobenzofuranyl, dihydrobenzotriazolyl, dihydroquinolinyl, tetrahydroquinolinyl, dihydroisoquinolinyl, tetrahydroisoquinolinyl, dihydrobenzisoxazolyl, naphthyl, anthracenyl, fluorenyl, indanyl, indenyl, dihydronaphthalene, tetrahydronaphthalene, carbazolyl, benzimidazolyl, benzothienyl, benzofuranyl, isobenzofuranyl, indolyl, quinolinyl, isoquinolinyl or isoindolyl, each of which is optionally substituted with 1 to 3 groups represented by $R^{16}$;

$R^{13}$ is —H and $R^{14}$ is —H, $(C_1$-$C_6)$alkyl, cyclopropyl, cyclobutyl, cyclopentyl, cyclohexyl, —O-cyclopropyl, —O-cyclobutyl, —O-cyclopentyl, —O-cyclohexyl, morpholinyl, thiomorpholinyl, pyrrolidinonyl, pyrrolidinyl, piperidinyl, piperazinyl, hydantoinyl, valerolactamyl, oxiranyl, oxetanyl, azetidinyl, dihydroimidazole, dihydrofuranyl, dihydropyranyl, dihydropyridinyl, dihydropyrimidinyl, dihydrothienyl, dihydrothiophenyl, dihydrothiopyranyl, tetrahydroimidazole, tetrahydrofuranyl, tetrahydropyranyl, tetrahydrothienyl, tetrahydropyridinyl, tetrahydropyrimidinyl, tetrahydrothiophenyl or tetrahydrothiopyranyl;

$R^{15}$ is independently selected from halogen, —$OR^c$, —$NR^aR^b$, and $(C_1$-$C_6)$alkyl;
each $R^{16}$ is independently selected from $(C_1$-$C_6)$alkyl; and m is 1.

16. The compound of claim 15, wherein $R^5$ is cyclohexyl, phenyl, pyridyl, pyrimidinyl, thiazolyl, or thienyl, each of which is optionally substituted with 1 to 3 groups selected from methyl, ethyl, propyl, halogen, hydroxymethyl, hydroxyethyl, methoxy, ethoxy, and —$(CH_2)_{0-2}$-morpholinyl.

17. The compound of claim 16, wherein $R^5$ is cyclohexyl, phenyl, pyridyl, pyrimidinyl, thiazolyl, or thienyl, each of which is optionally substituted with 1 to 3 groups selected from methyl, ethyl, propyl, halogen, and —$(CH_2)_{0-2}$-morpholinyl.

18. The compound of claim 17, wherein $R^{14}$ is —H, methyl, ethyl, propyl, butyl, isopropyl, isobutyl, hydroxymethyl, hydroxyethyl, hydroxypropyl, methoxy, ethoxy, propoxy, methoxymethyl, methoxyethyl, methoxypropyl, cyclopropyl, cyclobutyl, cyclopentyl, cyclohexyl, —O-cyclopropyl, —O-cyclobutyl, —O-cyclopentyl, —O-cyclohexyl, morpholinyl, oxetanyl, tetrahydrofuryl, tetrahydropyranyl, azetidinyl, pyrrolidinyl, piperidyl, wherein the morpholinyl, tetrahydrofuryl, tetrahydropyranyl, pyrrolidinyl, or piperidyl are optionally substituted with methyl.

19. The compound of claim 18 wherein $R^{14}$ is —H, butyl, isopropyl, isobutyl, cyclopropyl, cyclopentyl, or pyrrolidinyl.

20. A pharmaceutical composition comprising a compound of claim 1 and a pharmaceutically acceptable carrier or diluent.

21. A method for treating cancer, the method comprising: administering to a subject in need thereof an effective amount of the compound of claim 1, wherein the cancer is breast cancer, colon cancer or ovarian cancer.

* * * * *